(12) United States Patent
Gerson et al.

(10) Patent No.: US 10,722,530 B2
(45) Date of Patent: Jul. 28, 2020

(54) METHODS OF DIAGNOSING AND TREATING CANCER

(71) Applicant: CASE WESTERN RESERVE UNIVERSITY, Cleveland, OH (US)

(72) Inventors: Stanton Gerson, Hunting Valley, OH (US); Yan Yan, Cleveland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 200 days.

(21) Appl. No.: 15/854,345

(22) Filed: Dec. 26, 2017

(65) Prior Publication Data

US 2018/0185403 A1 Jul. 5, 2018

Related U.S. Application Data

(60) Provisional application No. 62/438,640, filed on Dec. 23, 2016, provisional application No. 62/477,019, filed on Mar. 27, 2017.

(51) Int. Cl.
*A61K 31/7072* (2006.01)
*A61K 31/519* (2006.01)
*A61P 35/02* (2006.01)
*A61P 35/00* (2006.01)

(52) U.S. Cl.
CPC ........ *A61K 31/7072* (2013.01); *A61K 31/519* (2013.01); *A61P 35/00* (2018.01); *A61P 35/02* (2018.01)

(58) Field of Classification Search
None
See application file for complete search history.

(56) References Cited

U.S. PATENT DOCUMENTS

| 2005/0095226 A1* | 5/2005 | Gjerset | A61K 31/166 424/93.2 |
|---|---|---|---|
| 2014/0066464 A1* | 3/2014 | Gerson | A61K 45/06 514/265.1 |
| 2016/0038444 A1* | 2/2016 | Alli | A61K 31/64 514/604 |

OTHER PUBLICATIONS

Yan et al., Mol Cancer Res vol. 16(2):212-221, Nov. 8, 2017.*

* cited by examiner

*Primary Examiner* — Sean McGarry
(74) *Attorney, Agent, or Firm* — Tarolli, Sundheim, Covell & Tummino LLP

(57) ABSTRACT

A method of treating cancer in a subject includes determining the p53 status and the level of UDG in cancer cells of the subject and administering an antimetabolite agent in combination with an AP endonuclease inhibitor or UDG inhibitor if the determined level of UDG in the cancer cells is increased relative to the control level and the cancer cells are p53 mutant or deficient cancer cells.

26 Claims, 32 Drawing Sheets

Specification includes a Sequence Listing.

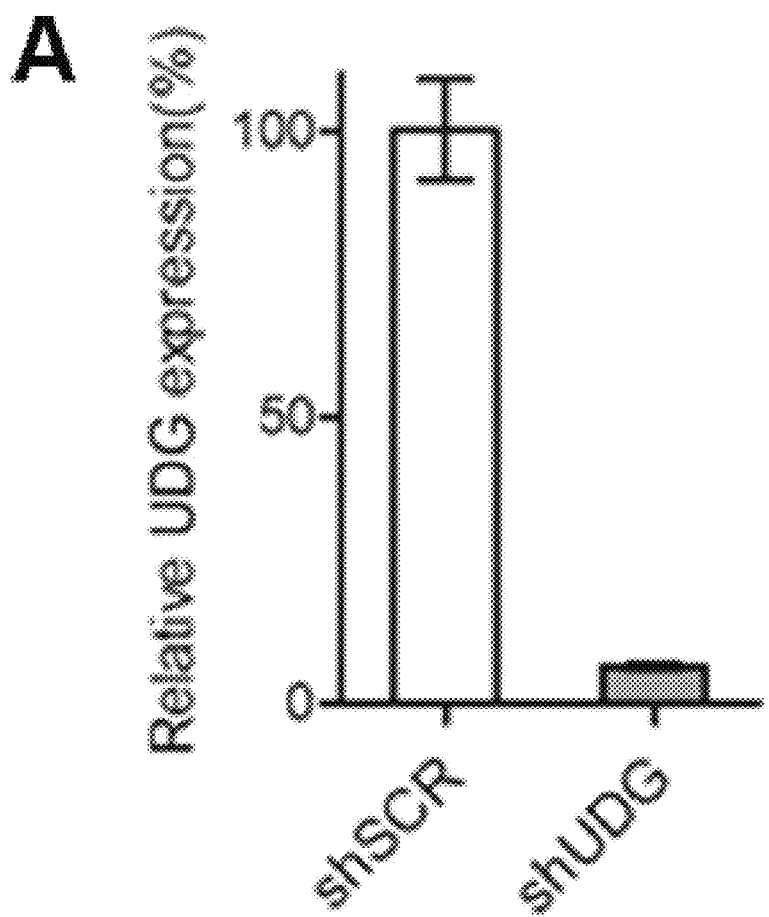
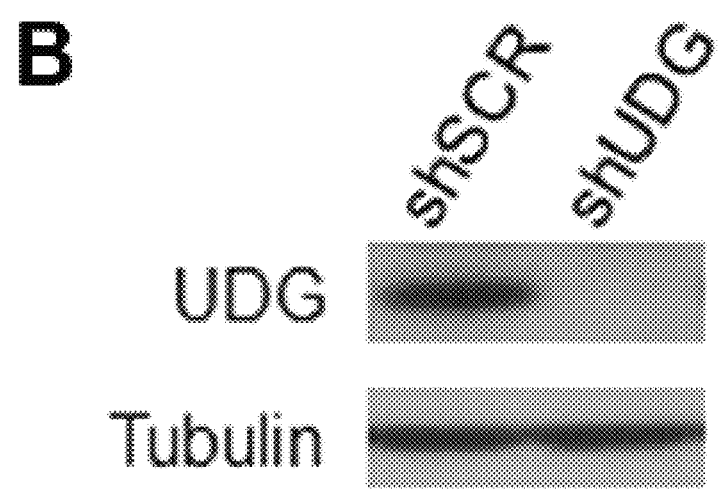
Figs. 1A-B

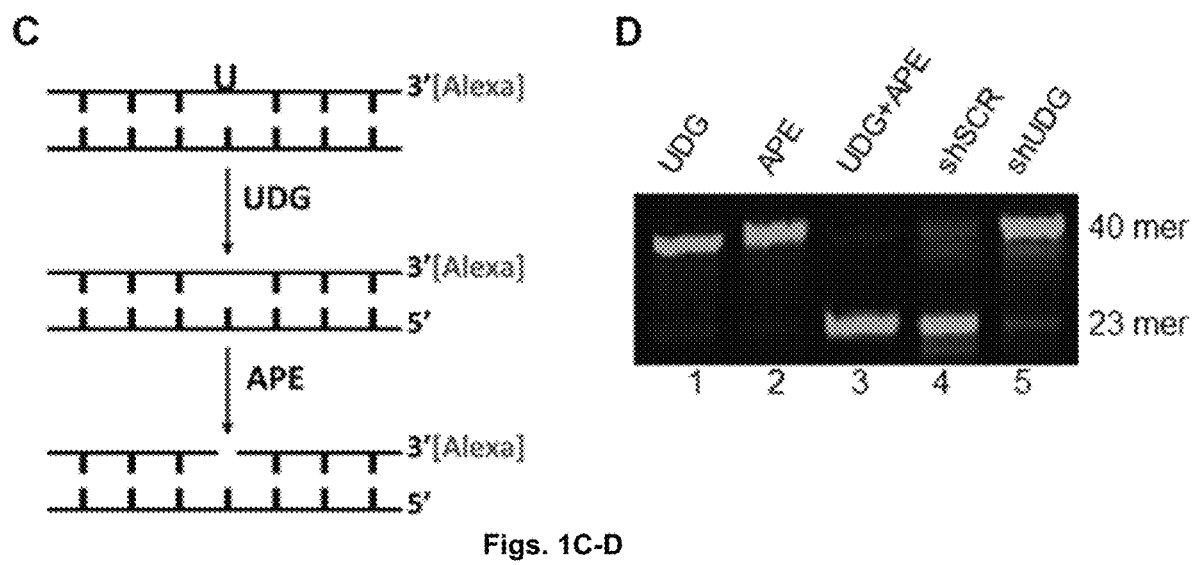
Figs. 1C-D
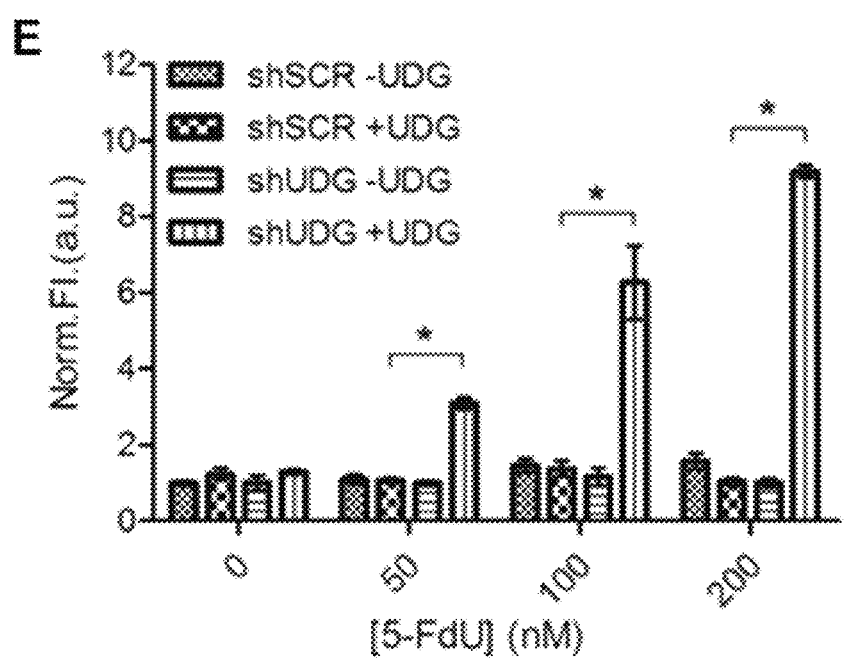
Fig. 1E

A
Cell lines and strains used in this work
| Cell line | Origin | MMR status | p53 status |
|---|---|---|---|
| DLD1 | Colon cancer | hMSH6- | Mutant |
| HCT116 | Colon cancer | hMLH1- | Wild-type |
| HCT116 p53KO | Colon cancer | hMLH1- | KO |
| RKO | Colon cancer | hMLH1- | Wild-type |
| HEC1A | Endometrial cancer | hPMS2-, hMSH6- | Mutant |
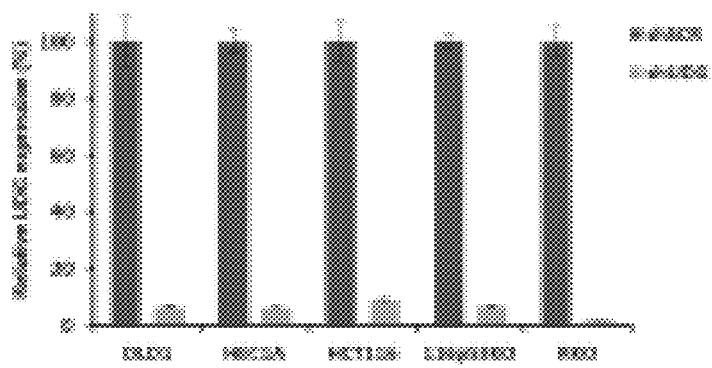
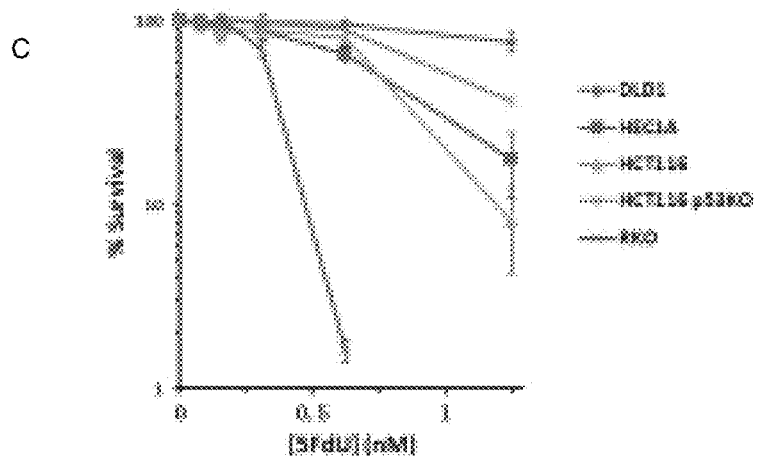
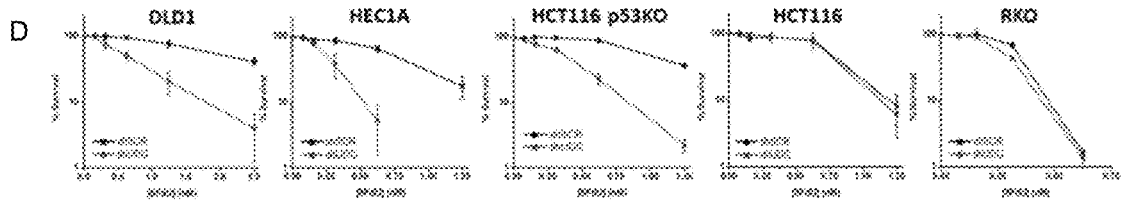
Figs. 10A-D

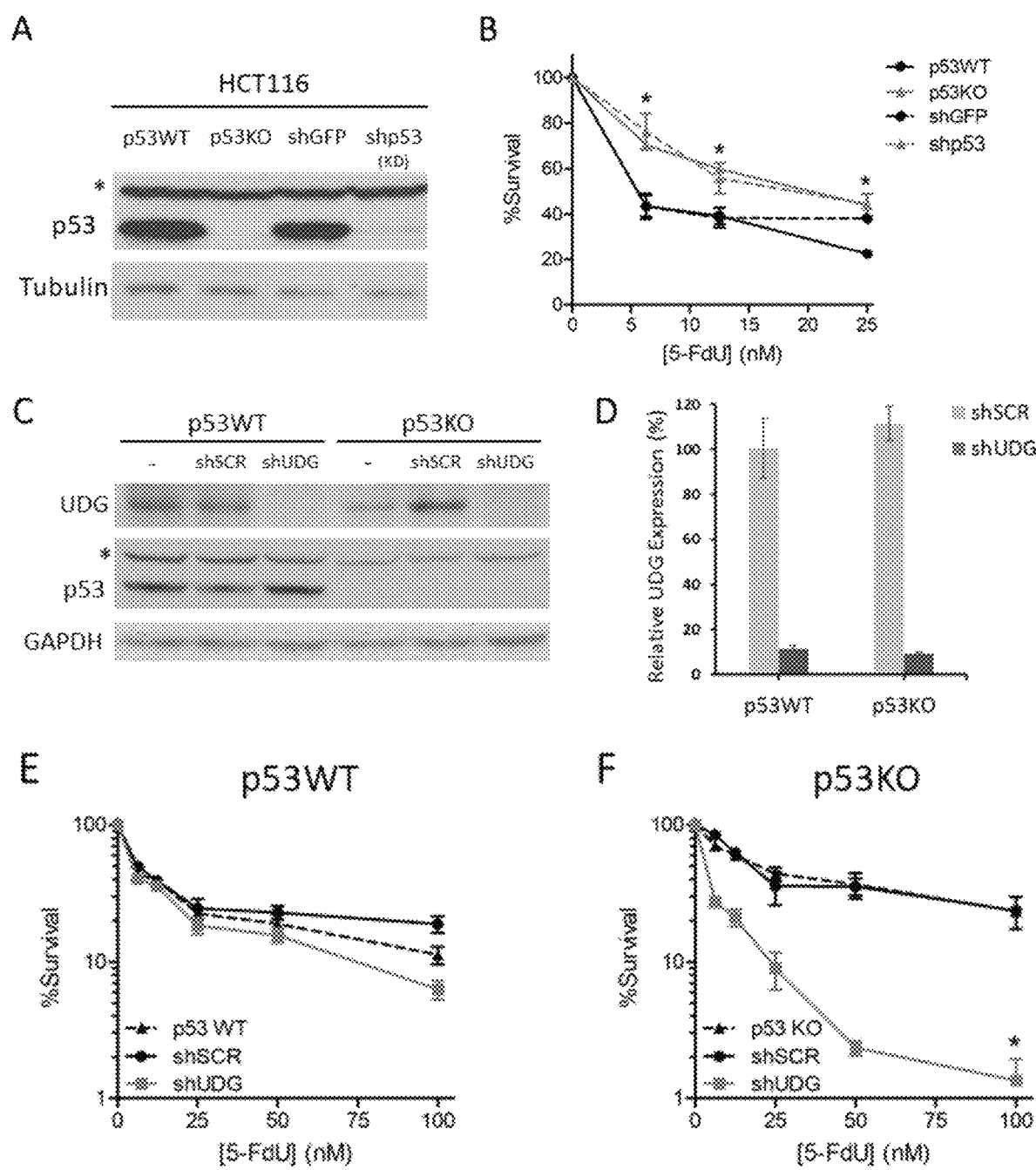
Figs. 11A-F

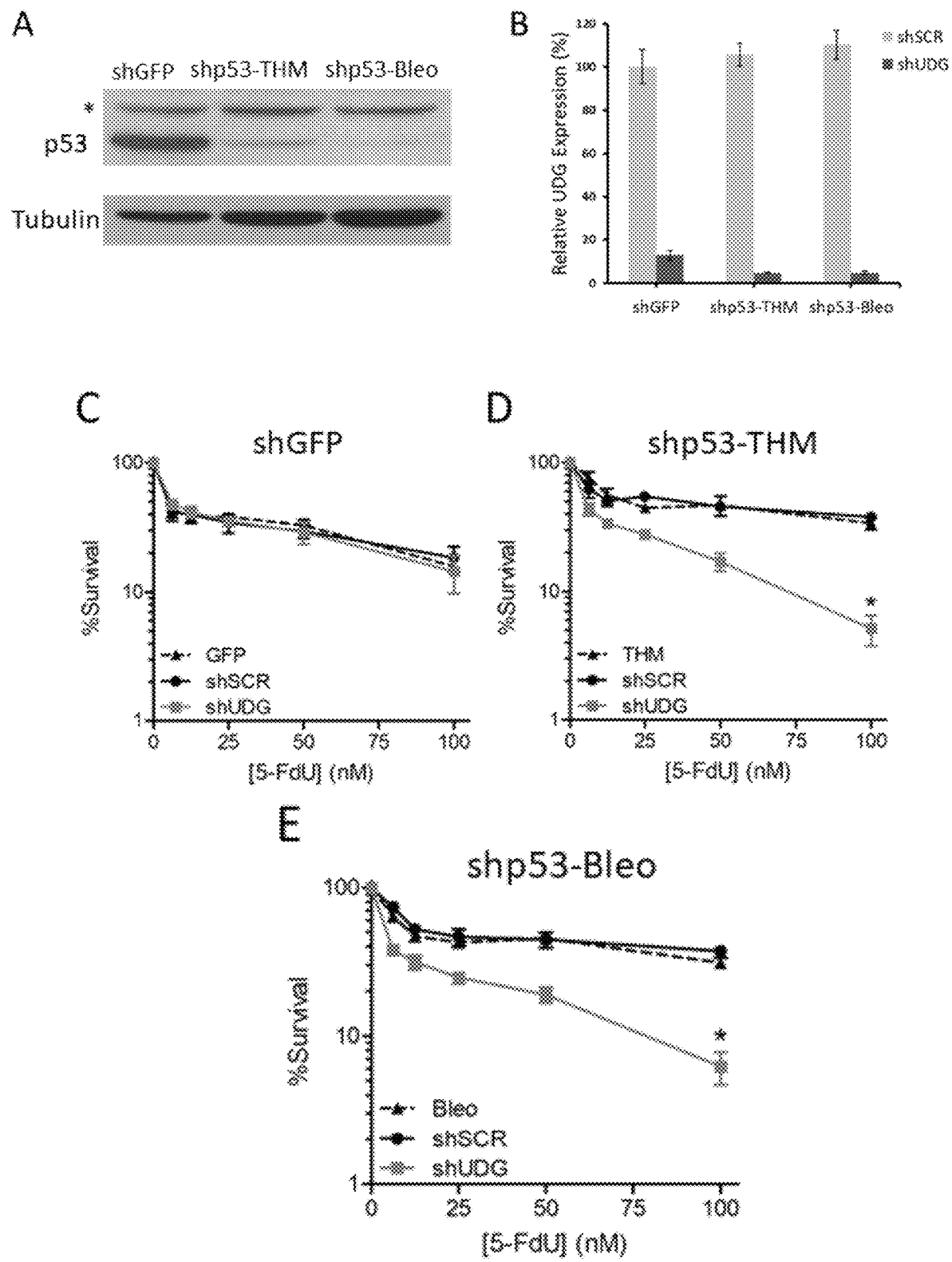
Figs. 12A-E

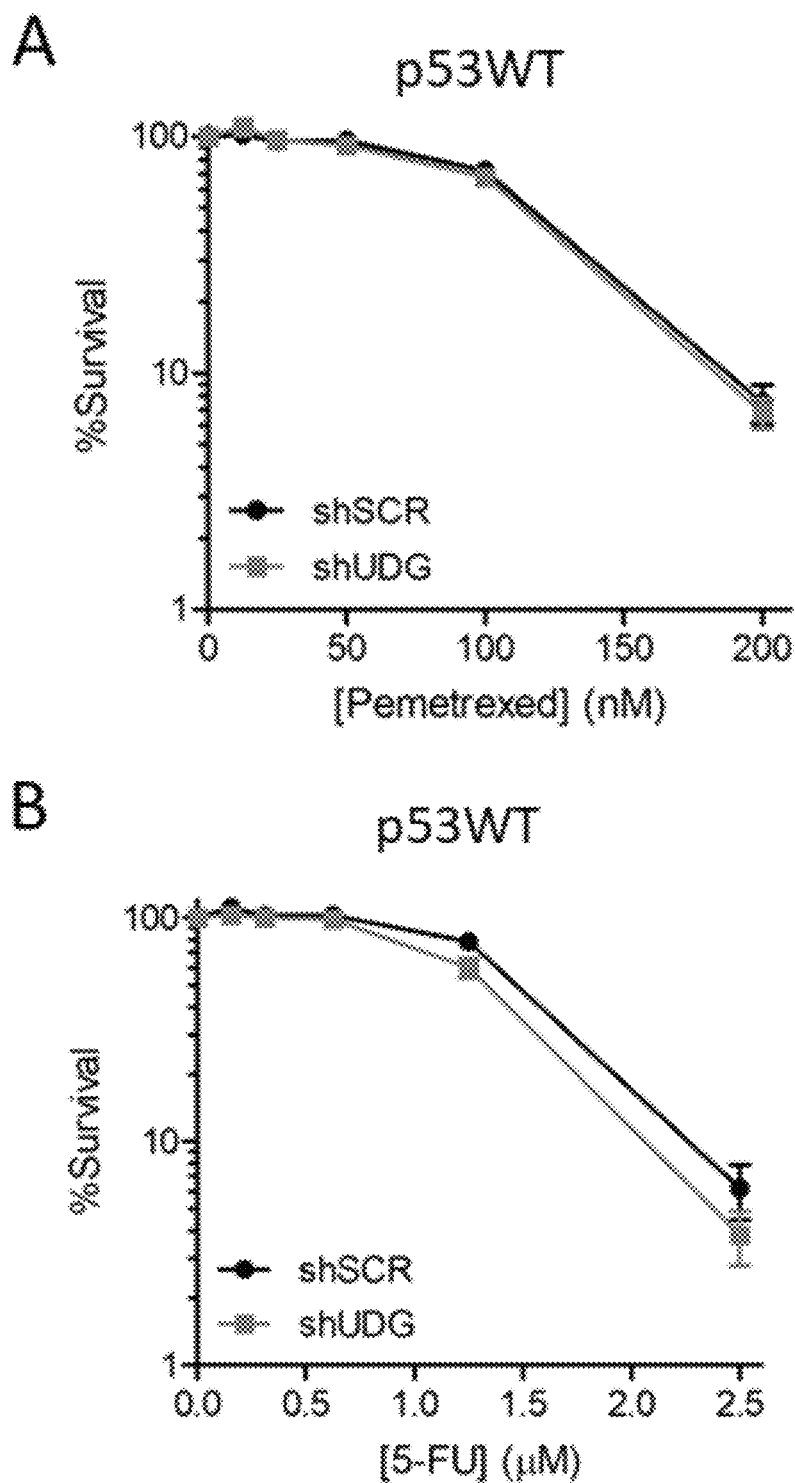
Figs. 13A-B

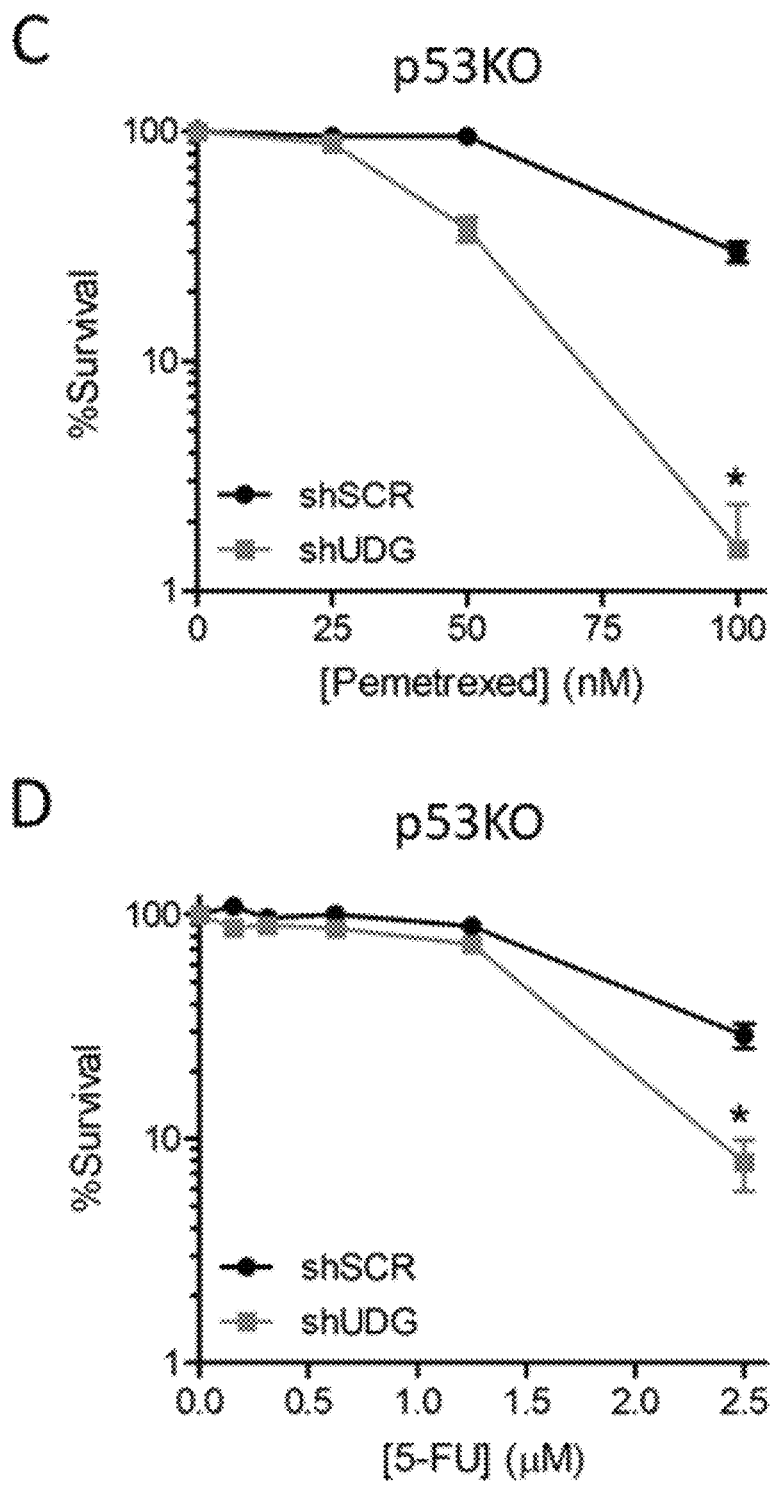
Figs. 13C-D

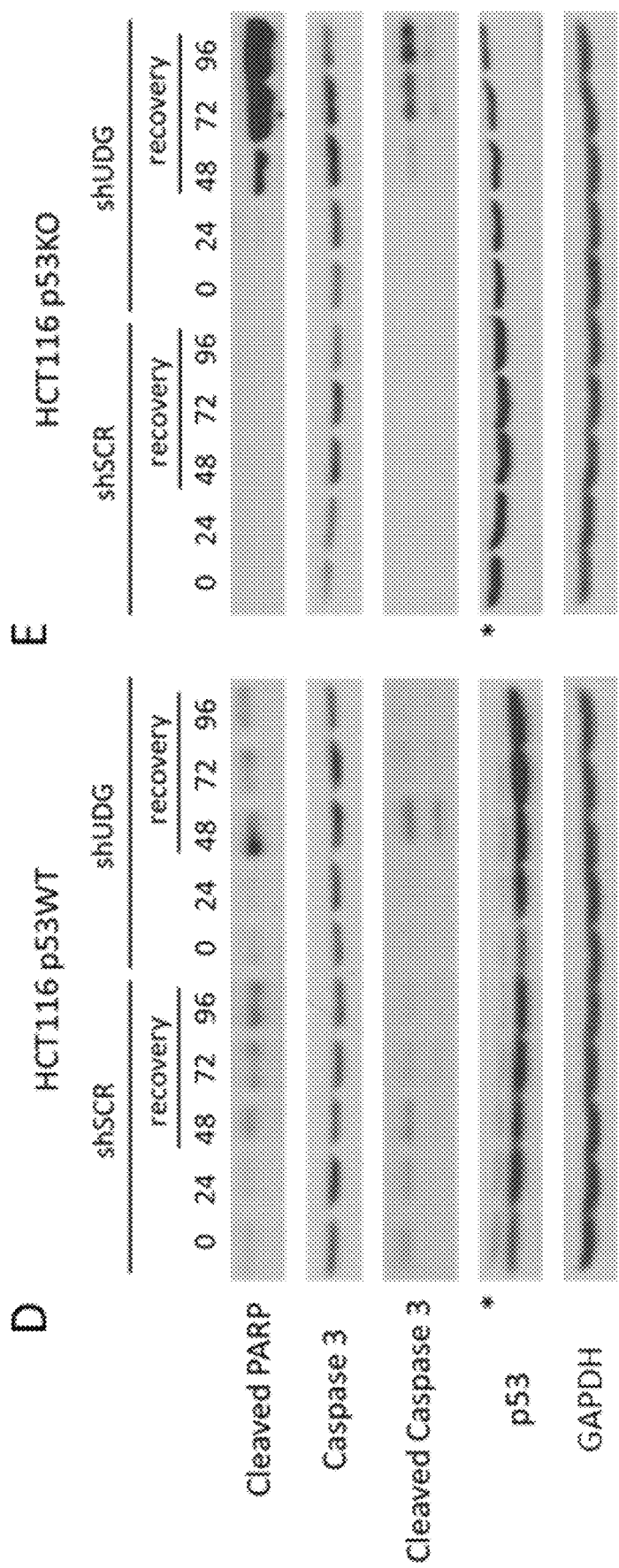
Figs. 14D-E

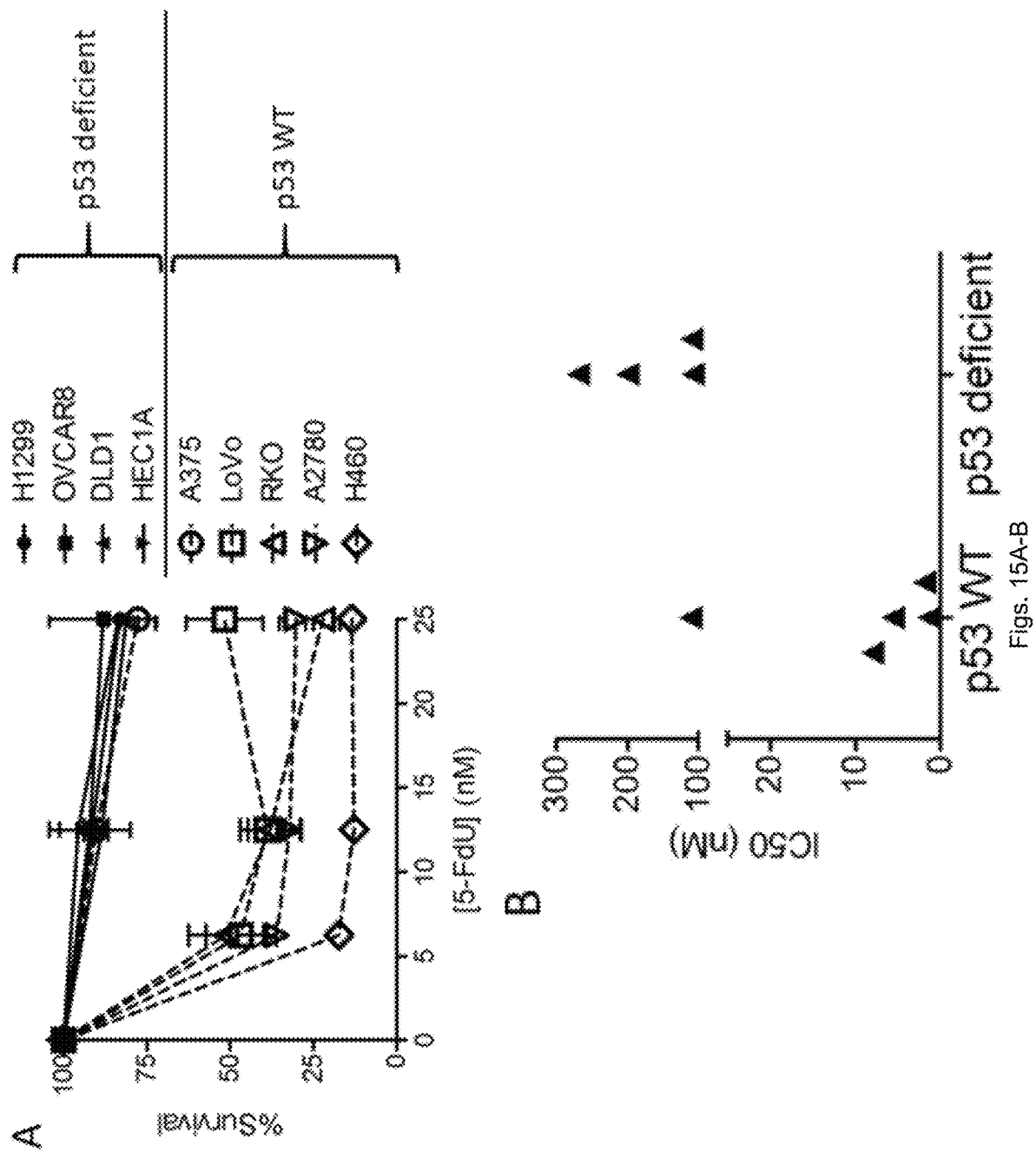
Figs. 15A-B

SEQUENCE LISTING

```
<160> NUMBER OF SEQ ID NOS: 2

<210> SEQ ID NO 1
<211> LENGTH: 40
<212> TYPE: DNA
<213> ORGANISM: Artificial Sequence
<220> FEATURE:
<223> OTHER INFORMATION: Synthetic Construct

<400> SEQUENCE: 1
tcctgggtga caaagcuaaa cactgtctcc aaaaaaaatt                           40

<210> SEQ ID NO 2
<211> LENGTH: 40
<212> TYPE: DNA
<213> ORGANISM: Artificial Sequence
<220> FEATURE:
<223> OTHER INFORMATION: Synthetic Construct

<400> SEQUENCE: 2
aggacccact gtttcgattt gtgacagagg ttttttttaa                           40
```

METHODS OF DIAGNOSING AND TREATING CANCER

RELATED APPLICATION

This application claims priority from U.S. Provisional Application Nos. 62/477,019, filed Mar. 27, 2017 and 62/438,640 filed Dec. 23, 2016, the subject matter of which are incorporated herein by reference in their entirety.

TECHNICAL FIELD

This application relates generally to methods for treating neoplastic disorders in a subject, and more particularly relates to methods of treating a p53 mutant or deficient cancer and/or solid tumor in a subject using antimetabolite antineoplastic agents and base excision repair inhibitors.

BACKGROUND

Cancer is a worldwide problem. Finding novel compositions and methods for treating cancer is of interest. The treatment of cancer falls into three general categories: chemotherapy, radiation therapy and surgery. Often, therapies are combined since a combination of therapies increases the probability the cancer will be eradicated as compared to treatment strategies utilizing a single therapy. Typically, the surgical excision of large tumor masses is followed by chemotherapy and/or radiation therapy.

Chemotherapeutic agents can work in a number of ways. For example, chemotherapeutics can work by interfering with cell cycle progression or by generating DNA strand breaks. If the cancer cell is not able to overcome the cell cycle blockage or cell injury caused by the therapeutic compound, the cell will often die via apoptotic mechanisms. The use of a single chemotherapeutic agent in the treatment of cancer, with or without surgery or radiation, has several disadvantages. Commonly, cancer cells develop resistance to the chemotherapeutic agent. Such resistance results either in the requirement for higher dosages of the drug and/or the renewed spread of the cancer. Chemotherapeutic agents can be toxic to the patient. Therefore, there is a practical upper limit to the amount that a patient can receive. However, if a second agent can be developed to inhibit the pathway causing resistance, cancer cells may become susceptible to the effects of the chemotherapeutic agent.

The design of a drug to overcome resistance to the chemotherapeutic treatment of cancer should be approached with the goals of 1) finding a combination that reverses resistance and not merely improves the activity of the chemotherapeutic with respect to activity on the tumor, and 2) finding a second drug that does not potentiate the toxic effects of the first chemotherapeutic agent. These conditions require a great deal of empirical testing of agents known to have anticancer properties with agents that either may have anticancer properties, or that may augment the first agent in other ways. Unfortunately, such approaches have thus far proven largely unsuccessful for combinations of many anticancer agents. Therefore, there exist insufficient therapies that reverse resistance to chemotherapy for the treatment of cancer.

SUMMARY

Embodiments described herein relate to a method of treating cancer in a subject. The method includes determining the p53 status and the level of UDG expression of cancer cells of the subject. An antimetabolite agent, which promotes introduction of uracil or a UDG substrate into the cancer cell DNA, and an AP endonuclease inhibitor or UDG inhibitor are administered to the subject if the determined level of UDG expression in the cancer cells is increased relative to the control level and the cancer cells are p53 mutant or deficient cancer cells.

In some embodiments, the cancer can include hepatocellular carcinoma, osteogenic sarcoma, colorectal cancer, uterine cancer, lung cancer, glioblastoma, esophageal carcinoma, bladder cancer, squamous cell carcinoma, leukemia and lymphoma. In some embodiments, the p53 related cancer is lung, colorectal, or uterine cancer. In certain embodiments, the human lung cancer is non-small lung cancer.

In some embodiments, the antimetabolite agent can include at least one of a thymidylate synthase inhibitor, antifolate agent, or a pyrimidine analogue. For example, the antimetabolite agent can be a thymidylate synthase inhibitor selected from the group consisting of pemetrexed, fludarabine, 5-fluorouracil, raltitrexed, nolatrexed, and floxuridine (5FdU). In some embodiments, the antimetabolite agent is an antifolate agent selected from the group consisting of pemetrexed and methotrexate.

In some embodiments, the AP endonuclease inhibitor is methoxyamine. In certain embodiments, the antimetabolite is pemetrexed or 5FdU and the AP endonuclease inhibitor is methoxyamine. In other embodiments the UDG inhibitor is a RNAi construct that inhibits or reduces expression of the UDG expression in the cancer cells of the subject. In certain embodiments, the RNAi construct includes a shRNA.

In some embodiments, the AP endonuclease inhibitor or UDG inhibitor can be administered at an amount effective to potentiate the cytotoxicity of the antimetabolite agent administered to the cancer cells. In some embodiments, the AP endonuclease inhibitor or UDG inhibitor is administered at an amount sufficient to sensitize the cancer cells to the antimetabolite without causing undue sensitization of normal cells.

Additional embodiments described herein relate to a method of treating a p53 mutant cancer in a subject. The method includes determining the level of UDG expression in cancer cells of the subject. An antifolate agent, which promotes introduction of uracil or a UDG substrate into the cancer cell DNA and an AP endonuclease inhibitor or UDG inhibitor are administered to the subject if the determined level of UDG activity in the cancer cells is increased relative to the control level.

In some embodiments, the p53 mutant cancer can include hepatocellular carcinoma, osteogenic sarcoma, colorectal cancer, uterine cancer, lung cancer, glioblastoma, esophageal carcinoma, bladder cancer, squamous cell carcinoma, leukemia and lymphoma. In some embodiments, the p53 mutant cancer is lung, colorectal, or uterine cancer. In certain embodiments, the human lung cancer is non-small lung cancer.

In some embodiments, the antimetabolite agent is an antifolate agent selected from the group consisting of pemetrexed and methotrexate. In some embodiments, the AP endonuclease inhibitor is methoxyamine. In certain embodiments, the antifolate is pemetrexed and the AP endonuclease inhibitor is methoxyamine. In other embodiments the UDG inhibitor is a RNAi construct that inhibits or reduces expression of the UDG expression in the cancer cells of the subject. In certain embodiments, the RNAi construct includes a shRNA.

In some embodiments, the AP endonuclease inhibitor or UDG inhibitor can be administered at an amount effective to potentiate the cytotoxicity of the antimetabolite agent administered to the cancer cells. In some embodiments, the AP endonuclease inhibitor or UDG inhibitor is administered at an amount sufficient to sensitize the cancer cells to the antimetabolite without causing undue sensitization of normal cells.

BRIEF DESCRIPTION OF THE DRAWINGS

The foregoing and other features of the application will become apparent to those skilled in the art to which the application relates upon reading the following description with reference to the accompanying drawings, in which:

FIGS. 10(A-D) illustrate that the loss of UDG overcomes the resistance of 5FdU in p53 mutant and p53 KO colon cancer cells.

FIGS. 11(A-F) illustrate that 5-FdU resistance due to loss of p53 is reversed by UDG depletion. (A) p53 expression levels were analyzed by Western blot in HCT116 cells with wild-type p53 (p53WT), knockout of p53 (p53KO), shGFP expressing vector (shGFP), and shp53 expressing vector (shp53). (*, non-specific bands) (B) Clonogenic survival assay for increasing doses of 5-FdU in HCT116 p53WT, p53KO, shGFP, and shp53 cells. HCT116 p53WT and p53KO cells stably infected with non-targeted scramble control shRNA (shSCR) or UDG-directed shRNA (shUDG) were analyzed by Western blot (C) and qPCR (D) to examine UDG levels. Clonogenic survival assays for increasing doses of 5-FdU in (E) p53WT cells alone, or with shSCR or shUDG, and (F) p53KO cells alone, or with shSCR or shUDG. Viable colonies (>50 cells) stained with methylene blue after 10 d of culture were counted. The results represent three independent experiments that were done in duplicate. (*, P<0.01).

FIGS. 12(A-E) illustrate that p53 knockdown re-sensitizes cancer cells with UDG depletion to 5-FdU. (A) HCT116 cells stably transfected with shGFP or shp53 (shp53-THM or shp53-Bleo) shRNAs were analyzed by the Western blot to examine p53 knockdown levels. (*, non-specific bands) (B) HCT116 cells expressing shGFP or shp53 (shp53-THM or shp53-Bleo) vectors were further infected with non-targeted scramble control shRNA (shSCR) or UDG-directed shRNA (shUDG). UDG mRNA levels were determined by qPCR. Clonogenic survival assays for increasing doses of 5-FdU in (C) shGFP, (D) shp53-THM, and (E) shp53-Bleo infected HCT116 cells alone, with shSCR or shUDG. Viable colonies (>50 cells) stained with methylene blue after 10 d of culture were counted. The results represent three independent experiments that were done in duplicate. (*, P<0.01).

FIGS. 13(A-D) illustrate that UDG depletion selectively sensitizes p53 KO cells to pemetrexed and 5-FU. Clonogenic survival assay in HCT116 p53 WT cells (shSCR and shUDG) treated with increasing doses of (A) pemetrexed and (B) 5-FU. Clonogenic survival assay in HCT116 p53 KO cells (shSCR and shUDG) treated with increasing doses of (C) pemetrexed and (D) 5-FU. Viable colonies (>50 cells) stained with methylene blue after 10 d of culture were counted. The results represent three independent experiments that were done in duplicate. (*, P<0.01).

FIGS. 15(A-B) illustrate that 5-FdU resistance in different types of cancer cells with p53 mutation or deficiency. (A) Clonogenic survival assay in cancer cells shown in Table 1 in response to increasing doses of 5-FdU. Cell lines with WT p53, dashed lines; cell lines with deficient (or mutant) p53, solid lines. The results represent three independent experiments that were done in duplicate. (B) IC50 values of 5-FdU for cancer cells with WT p53 or deficient p53, respectively.

DETAILED DESCRIPTION

Figure 1F:
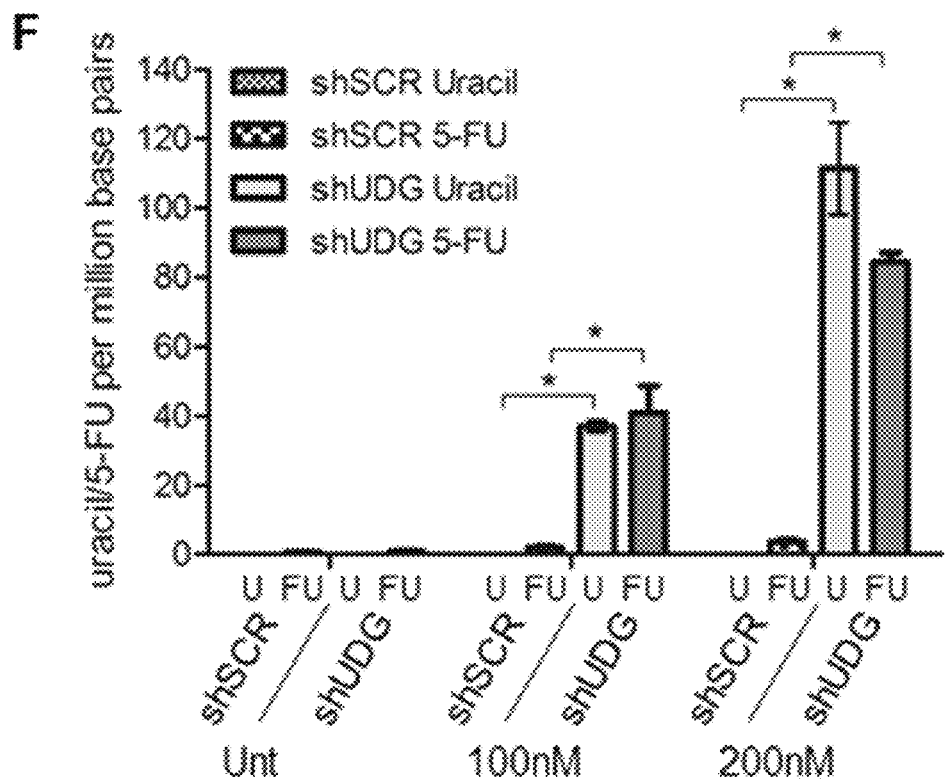
FIGS. 1(A-F) illustrates that UDG depletion causes incorporation of uracil and 5-FU into genomic DNA by 5-FdU. Lentiviral non-targeted scramble control shRNA (shSCR) or UDG-directed shRNA (shUDG) were transfected into DLD1 colon cancer cells, and stable cell lines were established. (A) UDG mRNA and (B) protein expression levels were determined by qPCR and western blot, respectively. The shRNA that we used targets both mitochondrial and nuclear UDG, which are collectively termed UDG in this study. (C) Schematic diagram of glycosylase activity assay by using 3'-Alexa tagged 40-mer DNA duplex with a uracil incorporation paired with adenine. (D) 10 μg nuclear extracts from DLD1 shSCR or shUDG cells were incubated with 3'-Alexa labeled oligonucleotide containing U:A base pair for 20 minutes at 37° C. Reactions with purified enzymes were used as controls. Cellular UDG activity was visualized by denaturing gel electrophoresis to separate intact 40-mer from 23-mer. (E) DLD1 shSCR and shUDG cells were treated with 0, 50, 100, and 200 nM 5-FdU for 48 h. Genomic DNA was extracted and treated in vitro with purified UDG (+UDG) or vehicle control (−UDG). AP sites detection was performed by incubation of DNA with a cyanine-based AP site probe. Data represent mean and SD of relative fluorescence intensity normalized to 5-FdU untreated shSCR-UDG sample from three independent experiments. (*P<0.05). (F) DLD1 shSCR and shUDG cells were untreated (Unt) or treated with 5-FdU 100 and 200 nM for 48 h. Genomic DNA was extracted and incubated in vitro with purified UDG enzyme. Uracil and 5-FU were quantified by LC-MS/MS as described in the Materials and Methods. Data represent mean and SD from three independent experiments. (*P<0.05).

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994. The definitions provided herein are to facilitate understanding of certain terms used frequently herein and are not meant to limit the scope of the application.

Unless indicated otherwise, the following terms have the following meanings when used herein and in the appended claims. Those terms that are not defined below or elsewhere in the specification shall have their art-recognized meaning.

As used in the specification and the appended claims, the singular forms "a," "an" and "the" include plural referents unless the context clearly dictates otherwise. Thus, for example, reference to "a substituent" includes a single substituent as well as two or more substituents that may be the same or different, reference to "a compound" encompasses a combination or mixture of different compounds as well as a single compound, reference to "a pharmaceutically acceptable carrier" includes two or more such carriers as well as a single carrier, and the like.

The terms "comprising" and variations thereof do not have a limiting meaning where these terms appear in the description and claims.

The term "agent" and "drug" are used herein to mean chemical compounds, mixtures of chemical compounds, biological macromolecules, or extracts made from biological materials, such as bacteria, plants, fungi, or animal particularly mammalian) cells or tissues that are suspected of having therapeutic properties. The agent or drug may be purified, substantially purified, or partially purified.

As used herein, the terms "treatment," "treating," or "treat" refer to any treatment of cancer, (e.g., colorectal, uterine cancer) in a subject including, but not limited to, inhibiting disease development, arresting development of clinical symptoms associated with the disease, and/or relieving the symptoms associated with the disease. However, the terms "treating" and "ameliorating" are not necessarily meant to indicate a reversal or cessation of the disease process underlying the cancer afflicting the subject being treated. Such terms indicate that the deleterious signs and/or symptoms associated with the condition being treated are lessened or reduced, or the rate of progression or metastasis is reduced, compared to that which would occur in the absence of treatment. A change in a disease sign or symptom can be assessed at the level of the subject (e.g., the function or condition of the subject is assessed), or at a tissue or cellular level. In accordance with the present invention, desired mechanisms of treatment at the cellular level include, but are not limited to one or more of a reduction of cancer cell process extension and cell migration, apoptosis, cell cycle arrest, cellular differentiation, or DNA synthesis arrest.

As used herein, the term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those having an enhanced risk of developing precancers and cancers. An elevated risk represents an above-average risk that a subject will develop cancer, which can be determined, for example, through family history or the detection of genes causing a predisposition to developing cancer.

The term "antimetabolite" is used herein to mean a chemotherapeutic with a similar structure to a substance (a metabolite e.g., nucleoside) required for normal biochemical reactions, yet different enough to interfere with the normal functions of cells, including cell division.

The term "antineoplastic" is used herein to mean a chemotherapeutic intended to inhibit or prevent the maturation and proliferation of neoplasms (tumors) that may become malignant, by targeting the DNA.

"Pharmaceutically acceptable" as used herein means that the compound or composition is suitable for administration to a subject to achieve the treatments described herein, without unduly deleterious side effects in light of the severity of the disease and necessity of the treatment.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

The terms "array", "micro-array", and "biochip" are used herein interchangeably. They refer to an arrangement, on a substrate surface, of hybridizable array elements, preferably, multiple nucleic acid molecules of known sequences. Each nucleic acid molecule is immobilized to a discrete spot (i.e., a defined location or assigned position) on the substrate surface. The term "micro-array" more specifically refers to an array that is miniaturized so as to require microscopic examination for visual evaluation.

The term "biological sample" is used herein in its broadest sense. A biological sample may be obtained from a subject (e.g., a human) or from components (e.g., tissues) of a subject. The sample may be of any biological tissue that includes cancer cells. Frequently, the sample will be a "clinical sample", i.e., a sample derived from a patient. Such samples include, but are not limited to, bodily fluids which may contain cancer cells, e.g., blood; tissue or fine needle biopsy samples, lung tissue; and archival samples with known diagnosis, treatment and/or outcome history. Biological samples may also include sections of tissues or cells, such as frozen sections taken from histological purposes. The term biological sample also encompasses any material derived by processing the biological sample. Derived materials include, but are not limited to, cells (or their progeny) isolated from the sample, proteins or nucleic acid molecules extracted from the sample. Processing of the biological sample may involve one or more of, filtration, distillation, extraction, concentration, inactivation of interfering components, addition of reagents, and the like.

The term "control sample" refers to one or more biological samples isolated from an individual or group of individuals that are normal (i.e., healthy).

The term "decreased level of expression" as used herein, refers to a decrease in expression of a polynucleotide, e.g., gene, RNA, DNA, or protein at least 10% or more. For example, 20%, 30%, 40%, or 50%, 60%, 70%, 80%, 90% or more, or a decrease in expression of greater than 1-fold, 2-fold, 3-fold, 4-fold, 5-fold, 10-fold, 50-fold, 100-fold or more as measured by one or more methods described herein. The term "increased level of expression" as used herein, refers to an increase in expression of a polynucleotide, e.g., gene, RNA, DNA, or protein at least 10% or more. For example, 20%, 30%, 40%, or 50%, 60%, 70%, 80%, 90% or more or an increase in expression of greater than 1-fold, 2-fold, 3-fold, 4-fold, 5-fold, 10-fold, 50-fold, 100-fold or more as measured by one or more methods, such as method described herein.

The term "diagnosis" refers to a process aimed at determining if an individual is afflicted with a disease or ailment.

The term "hybridizing" refers to the binding of two single stranded nucleic acids via complementary base pairing. The term "specific hybridization" refers to a process in which a nucleic acid molecule preferentially binds, duplexes, or hybridizes to a particular nucleic acid sequence under stringent conditions (e.g., in the presence of competitor nucleic acids with a lower degree of complementarity to the hybridizing strand). In certain embodiments of the present invention, these terms more specifically refer to a process in which a nucleic acid fragment (or segment) from a test sample preferentially binds to a particular probe and to a lesser extent or not at all, to other probes, for example, when these probes are immobilized on an array.

The terms "labeled", "labeled with a detectable agent" and "labeled with a detectable moiety" are used herein interchangeably. These terms are used to specify that an entity (e.g., a probe) can be visualized, for example, following binding to another entity (e.g., a polynucleotide or polypeptide). Preferably, the detectable agent or moiety is selected such that it generates a signal which can be measured and whose intensity is related to the amount of bound entity. In array-based methods, the detectable agent or moiety is also preferably selected such that it generates a localized signal, thereby allowing spatial resolution of the signal from each spot on the array. Methods for labeling polypeptides or polynucleotides are well-known in the art. Labeled polypeptides or polynucleotides can be prepared by incorporation of or conjugation to a label that is directly or indirectly detectable by spectroscopic, photochemical, biochemical, immunochemical, electrical, optical, or chemical means. Suitable detectable agents include, but are not limited to, various ligands, radionuclides, fluorescent dyes, chemiluminescent agents, microparticles, enzymes, calorimetric labels, magnetic labels, and haptens. Detectable moieties can also be biological molecules such as molecular beacons and aptamer beacons.

The term "morphology" is used herein to mean the visual appearance of a cell or organism when viewed with the eye, a light microscope, a confocal microscope or an electron microscope, as appropriate.

The terms "normal" and "healthy" are used herein interchangeably. They refer to an individual or group of individuals who have not shown to have cancer or tumors. In certain embodiments, normal individuals have similar sex, age, body mass index as compared with the individual from which the sample to be tested was obtained. The term "normal" is also used herein to qualify a sample isolated from a healthy individual.

The terms "nucleic acid molecule" and "polynucleotide" are used herein interchangeably. They refer to a deoxyribonucleotide or ribonucleotide polymer in either single- or double-stranded form, and unless otherwise stated, encompass known analogs of natural nucleotides that can function in a similar manner as naturally occurring nucleotides. The terms encompass nucleic acid-like structures with synthetic backbones, as well as amplification products.

The term "probe", as used herein, refers to a nucleic acid molecule of known sequence, which can be a short DNA sequence (i.e., an oligonucleotide), a PCR product, or mRNA isolate. Probes are specific DNA sequences to which nucleic acid fragments from a test sample are hybridized. Probes specifically bind to nucleic acids of complementary or substantially complementary sequence through one or more types of chemical bonds, usually through hydrogen bond formation.

The terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is the full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains, such as oxidation of sulfhydryl groups. Thus, the term "protein" (or its equivalent terms) is intended to include the amino acid sequence of the full-length native protein, subject to those modifications that do not change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative splicing or limited proteolysis), or in the alternative, may arise from differential post-translational modification (e.g., glycosylation, acylation, phosphorylation).

The term "protein analog", as used herein, refers to a polypeptide that possesses a similar or identical function as the full-length native protein but need not necessarily comprise an amino acid sequence that is similar or identical to the amino acid sequence of the protein, or possesses a structure that is similar or identical to that of the protein. Preferably, in the context of the present invention, a protein analog has an amino acid sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the amino acid sequence of the full-length native protein.

The term "protein fragment", as used herein, refers to a polypeptide comprising an amino acid sequence of at least 4 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a second polypeptide. The fragment of a marker protein may or may not possess a functional activity of the full-length native protein.

The term "subject," "individual," and "patient" are used interchangeably herein to mean a human or other animal, such as farm animals or laboratory animals (e.g., guinea pig or mice) capable of having cell cycle (influenced) determined diseases, either naturally occurring or induced, including but not limited to cancer.

The term "reverses resistance" means that the use of a second agent in combination with a primary chemotherapeutic is able to produce a significant decrease in tumor volume at a level of statistical significance (e.g., $p<0.05$) when compared to tumor volume of untreated tumor in the circumstance where the primary chemotherapeutic alone is unable to produce a statistically significant decrease in tumor volume compared to tumor volume of untreated tumor. This generally applies to tumor volume measurements made at a time when the untreated tumor is growing logarithmically.

The term "potentiate" as used herein means to enhance or increase the beneficial activity or efficacy of the anticancer agent (e.g., an antimetabolite) over that which would be expected from the anticancer agent alone or the potentiating agent alone.

The term "sensitize" as used herein means to alter cancer cells or tumor cells in a way that allows for more effective treatment of the associated neoplastic disease with an antimetabolite agent, an anticancer agent, or radiation therapy. In some embodiments, cancer cell sensitization occurs wherein normal cells are not affected to an extent that causes the normal cells to be unduly injured by the antimetabolite, chemotherapy, or radiation therapy.

The term "subject" and "individual" are used herein interchangeably. They refer to any human or mammal subject who has a disorder characterized by unwanted, rapid cell proliferation. Such disorders include, but are not limited to cancers and precancers. In particular embodiments, the subject includes any human or animal subject that is suspected of having or has been diagnosed with p53 related cancer. For methods of prevention the subject is any human or animal subject, and preferably is a human subject who may not have the disease but is at risk of acquiring a disorder characterized by unwanted, rapid cell proliferation, such as cancer. In particular embodiments, the subject includes subjects predisposed to a p53 related cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

As used herein, the terms "subject diagnosed with cancer", "subject having cancer" or "subjects identified with cancer" refers to patient subjects that are identified as having or likely having cancer. In certain embodiments, the patient subjects are identified as having or likely having a p53 related cancer, such as a p53 mutant cancer. Nonlimiting examples of diagnosing a subject with cancer include diagnoses using histological analysis conducted by a board-certified pathologist and diagnostic tests based on molecular approaches. In some embodiments, diagnostic tests for identifying a p53 mutation in a subject or subject sample can be achieved using diagnostic sequencing assays based on mRNA (using cDNA sequencing) and/or genomic DNA sequencing.

As used herein "p53 related cancer" refers to any cancer, such as a p53 mutant cancer, in which p53 is related to the onset or progression thereof. Such a cancer can be caused by a mutation in the p53 gene [GenBank Accession Nos. NC-000017: 7512464-7531642 (genomic region); NM-000546 (mRNA); NP-000537 (protein)] leading to an abnormal structure and/or function of the p53 protein. Such a mutation can be a missense, nonsense, splice mutation, promoter mutation, deletion, insertion, duplication and the like. Various mutations in the p53 protein result in intermediate or severe conformational changes leading to abnormal function of the p53 protein. p53 is a nuclear transcription factor with a pro-apoptotic function and it is estimated that over 50% of human cancers carry loss of function mutations in p53 gene. Non-limiting examples of p53 related cancer include those caused by germline mutations in the p53 gene (e.g., in the case of Li-Fraumeni syndrome 1, OMIM #151623) as well as those caused by somatic mutations in the p53 gene. In certain embodiments, non-limiting examples of p53 related cancers include, but are not limited to, hepatocellular carcinomas, osteogenic sarcomas, colorectal cancer, uterine cancer, lung cancer (such as non-small cell lung cancer), glioblastomas, esophageal carcinoma, bladder cancer, squamous cell carcinomas, leukemia and lymphoma.

The term "synergistic effect" as used herein means the combined effect of two or more anticancer agents or chemotherapy drugs can be greater than the sum of the separate effects of the anticancer agents or chemotherapy drugs alone.

The term "therapeutically effective amount" means the amount of the subject compound(s) that will elicit a desired response, for example, a biological or medical response of a tissue, system, animal, or human that is sought, for example, by a researcher, veterinarian, medical doctor, or other clinician. For example, a therapeutically effective amount of one or more of the therapeutic agents described herein or combinations thereof provides an amount that is effective to reduce or arrest a disease or disorder such as abnormal cell growth or cell migration in a subject. The result can be a reduction and/or alleviation of the signs, symptoms, or causes of a disease or disorder, or any other desired alteration of a biological system. The effectiveness of treatment may be measured by evaluating a reduction in tumor load or tumor volume or decrease in tumor growth or tumor cell invasion and/or migration in a subject in response to the administration of a one or more of the therapeutic agents described herein or combinations thereof. The reduction in tumor load may represent a direct decrease in mass, or it may be measured in terms of tumor growth delay, which is calculated by subtracting the average time for control tumors to grow over to a certain volume from the time required for treated tumors to grow to the same volume. The decrease in tumor cell metastasis may represent a direct decrease in tumor cell migration, or it may be measured in terms of the delay of tumor cell metastasis. An effective amount of one or more of the therapeutic agents described herein or combinations thereof in either case may be determined by one of ordinary skill in the art using routine experimentation.

The terms "uracil DNA glycosylase" or "UDG" or "UNG" refer to a conserved DNA repair protein expressed in all types of human cells. It specifically removes uracil from DNA and protects cells from cytotoxicity and mutagenicity. Human UDG is encoded by the UDG gene. Alternative promoter usage and splicing of this gene produces two different isoforms: the mitochondrial UDG1 and the nuclear UDG2. Nuclear UDG (UDG2) is the predominant form in cells and represents greater than 90% of the total enzyme activity.

The term "wild type" (wt) cell or cell line is used herein, for purposes of the specification and claims, to mean a cell or cell line that retains the characteristics normally associated with that type of cell or cell line for the physiological process or morphological characteristic that is being examined. It is permissible for the cell or cell line to have non-wild type characteristics for physiological process or morphological characteristics that are not being examined as long as they do not appreciably affect the process or characteristic being examined.

Embodiments described herein relate to methods of treating cancer in a subject with an antimetabolite agent that induces or promotes incorporation of a UDG substrate into DNA of the cancer cells. The methods include determining the p53 status of cancer cells in the subject and the level of UDG expression in the cancer cells of the subject. The antimetabolite agent is administered in combination with an AP endonuclease inhibitor or UDG inhbitor to the subject if the determined level of UDG expression in the cancer cells is increased relative to the control level and the cancer cells are p53 mutant or deficient cancer cells, wherein the antimetabolite promotes introduction of uracil or a UDG substrate into the cancer cell DNA.

UDG substrates, such as uracil and/or 2-fluoroadenine 9-β-Darbinofuranoside-triphosphate can be incorporated into DNA of cancer cells by administering antimetabolite agents to the cancer cells. The UDG substrates can serve as a poor substrate for DNA replication enzymes, leading to the inhibition of DNA replication, chain termination, and loss of genome integrity. To maintain the genome integrity of the cancer cells, the cancer cells rapidly eliminate the UDG substrate from the DNA by base excision repair (BER), which is initiated by the UDG (or UNG) enzyme. The UDG enzyme hydrolyzes the N-glycosidic bond between the UDG substrate (e.g., uracil residue) and the deoxyribose sugar of the DNA backbone, liberating the UDG substrate and generating an abasic site (e.g., an apurinic or apyrimidinic (AP) site). An apurinic or apyrimidinic (AP) site results from the loss of a purine or pyrimidine residue, respectively, from DNA (deoxyribonucleic acid). The AP site is further processed by a 5'-3' endonuclease (AP endonuclease (APE)) that incises the phosphodiester bond on both sides of the damaged purine or pyrimidine base. The AP endonucleases can introduce chain breaks by cleaving the phosphodiester bonds at the AP sites.

It has been shown that, 5-fluorodeoxyuridine (5-FdU, floxuridine); an antimetabolite chemotherapeutic drug used in cancer care and a thymidylate synthase (TS) inhibitor has only modest effectiveness against cancer. Once transported into cells, 5-FdU can be converted to fluorodeoxyuridine monophosphate (FdUMP) or fluorodeoxyuridine triphosphate (FdUTP). FdUMP inhibits TS, causing nucleotide pool imbalance and uracil incorporation into DNA. On the other hand, FdUTP is also incorporated into DNA as the modified base 5-FU. Therefore, mechanisms regulating the removal and repair or uracil and other UDG substrates, such as 5-FU, play important roles in determining the anticancer effect of antimetabolites such as 5-FdU.

In mammalian cells, both uracil and 5-FU are primarily removed by UDG, a step critical for the subsequent DNA damage repair via the base excision repair (BER) pathway. However, how exactly UDG regulates the cellular sensitivity to 5-FdU was not understood. It has been discovered that UDG depletion leads to persistence of incorporation of both uracil and 5-FU into DNA following exposure to the 5-FdU (a thymidylate synthase antimetabolite agent), and UDG depletion significantly enhanced 5-FdUs cytotoxicity in various cancer cells. It was further discovered that UDG depletion also dramatically increased DNA damage induced by 5-FdU, indicating the deficiency of damage repair in these cells.

In addition, it was discovered that depletion of UDG is able to specifically enhance the cytotoxicity of an antimetabolite agent cancer in cells with p53 mutation or deficiency. Without being bound by theory, the mechanism appears to be that loss of UDG induces early S phase arrest in p53 deficient cancer cells following 5-FdU exposure and uracil and 5FU incorporation due to loss of UDG accelerate stall or collapse of replication fork and potentiate cytotoxicity of 5FdU in p53-mutant and p53-deficient cancer cells.

Advantageously, the identification of UDG expression as a predictive marker for antimetabolite resistance in p53 related cancers can be used to potentiate antimetabolite efficacy via BER inhibition. It is further contemplated that inhibition of UDG (e.g., using AP endonuclease or a UDG inhibitor) induced BER restores antimetabolite sensitivity in p53 related cancer cells expressing increased levels of UDG. Therefore, tailoring chemotherapy based on determined p53 status (e.g., mutant, deficient or wild type) and measured UDG expression of a subject's cancer cells can be employed as a favorable strategy for aggressive, treatment-refractory malignancies, such as cancer.

The P53 tumor suppressor gene has been identified in a wide variety of human cancers (see Vogelstein et al., (2000) Nature 408:307-310). The p53 related cancer can be selected from, but not limited to, the group consisting of hepatocellular carcinomas, osteogenic sarcomas, colorectal cancer, uterine cancer, lung cancer, glioblastomas, esophageal carcinoma, bladder cancer, squamous cell carcinomas, leukemia and lymphoma. In some embodiments, the p53 related cancer treated in a method described herein is p53 related lung, colorectal or uterine cancer. In a certain embodiment, the p53 related cancer treated in a method described herein is p53 related non-small cell lung cancer.

Methods used for the detection of P53 mutations are typically based either on genomic DNA or mRNA as a template (Ohgaki et al. (2004) *Cancer Res.* 64:6892-6899, Taubert et al. (1998) *Anticancer Res.* 18:183-187, Sjogren et al. (1996) *J Natl Cancer Inst.* 88:173-182). For example, the P53 gene status can be evaluated, and thus determined, using both cDNA and DNA sequencing and real-time quantitative RT-PCR. However, P53 mutations are detected more frequently at the mRNA level (using cDNA sequencing) than at the DNA level in glioblastomas, colorectal cancer and pleomorphic xanthoastrocytoma (see for example Szybka et al. (2008) *Br J Cancer* 98:1431-1433, Szybka et al. (2009) *BMC Cancer* 11:2782009, and Zakrzewska et al., (2009) *Cancer Genet Cytogenet* 193:93-97).

Additional assays to evaluate and determine the p53 status of a subject's cancer cells can include immunoassays featuring antibodies directed against p53 mutant proteins. Immunoassays for evaluating the p53 status of a subject's cancer cells can include an enzyme linked immunosorbent assay (ELISA), Western blot, radio-immunoassays, fluorescence activated cell sorting (FACS) and molecular weight based approaches.

In some embodiments, an ELISA can be used to evaluate the p53 status (i.e., the presence of a p53 mutation or deficiency), of a subjects cancer cells (see for example U.S. Pat. No. 8,207,309 B2, incorporated herein by reference). An ELISA involves fixation of a sample (e.g., fixed cells or a proteinaceous solution) containing an antigen (e.g., p53 mutant proteins) to a surface such as a well of a microtiter plate. An antigen specific antibody coupled to an enzyme is applied and allowed to bind to the antigen. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

In some embodiments, the level of UDG expression in the p53 mutant or deficient cancer cells of the subject can be determined by obtaining a sample of cancer cells from the subject diagnosed with p53 related cancer and measuring the level of UDG expression in the cancer cells. In some embodiments, both the level of UDG expression in the cancer cells and the p53 status of the cancer cells can be determined from the same sample if necessary. For example if the subject has not yet been diagnosed with a p53 related cancer, assays to determine the p53 status of the cancer cells can be performed using the same sample used to determine the level of UDG expression. In other embodiments, the level of UDG expression in the cancer cells and the p53 status of the cancer cells can be determined from similar biological samples (e.g., samples from the same tissue, fluid, or body part) obtained at different times. In yet other embodiments, the level of UDG expression in the cancer cells and the p53 status of the cancer cells can be determined from dissimilar biological samples (e.g., samples from the different tissue, fluid, or body part) obtained at different times.

In some embodiments, the p53 related cancer is a cancer or tumor in which UDG is expressed at a greater level or amount (e.g., over expressed) compared to normal cells or other cancer cells. UDG is expressed in several types of human tumor cell types at higher levels than corresponding normal cells and at least some other cancers. Cancers or cancer cells that have a high UDG expression level compared to normal cells can include, but are not limited to, lung cancer, including non-small cell lung cancer cells, lymphoma, chronic lymphotic leukemia, mesothelioma, colorectal cancer, pancreatic cancer, breast cancer, cervical cancer, leukemia, and non-Hodgkin's lymphoma.

The samples used in the practice of the inventive methods may be fresh or frozen samples collected from a subject, or archival samples. Biological samples may be collected by any non-invasive means, such as, for example, by drawing blood from a subject, or using fine needle aspiration or needle biopsy. Alternatively, biological samples may be collected by an invasive method, including, for example, surgical biopsy. In certain embodiments, the inventive methods are performed on the biological sample itself without or with limited processing of the sample.

In other embodiments, the inventive methods are performed at the single cell level (e.g., isolation of cells from a biological sample). However, in such embodiments, the inventive methods are preferably performed using a sample comprising many cells, where the assay is "averaging" expression over the entire collection of cells present in the sample. Preferably, there is enough of the biological sample to accurately and reliably determine the expression of UDG and p53 status if necessary. Multiple biological samples may be taken from the same tissue/body part in order to obtain a representative sampling of the tissue.

In still other embodiments, the level of UDG expression can be measured in a protein extract prepared from cancer cells of a biological sample. The protein extract can contain the total UDG content by the cancer cell or cells. Methods of protein extraction are well known in the art (see, for example "Protein Methods", D. M. Bollag et al., 2nd Ed., 1996, Wiley-Liss; "Protein Purification Methods: A Practical Approach", E. L. Harris and S. Angal (Eds.), 1989; "Protein Purification Techniques: A Practical Approach", S. Roe, 2nd Ed., 2001, Oxford University Press; "Principles and Reactions o/Protein Extraction, Purification, and Characterization", H. Ahmed, 2005, CRC Press: Boca Raton, Fla.). Numerous different and versatile kits can be used to extract proteins from cells, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). User Guides that describe in great detail the protocol to be followed are usually included in all these kits. Sensitivity, processing time and costs may be different from one kit to another. One of ordinary skill in the art can easily select the kits most appropriate for a particular situation. After the protein extract has been obtained, the protein concentration of the extract can be standardized to a value being the same as that of the control sample in order to allow signals of the UDG expression to be quantitated. Such standardization can be made using photometric or spectrometric methods or gel electrophoresis.

In yet other embodiments, the level of UDG expression can be measured from nucleic acid molecules extracted from cancer cells of a biological sample. For example, RNA may be extracted from the sample before analysis. Methods of RNA extraction are well known in the art (see, for example, J. Sambrook et al., "Molecular Cloning: A Laboratory Manual", 1989, 2nd Ed., Cold Spring Harbor Laboratory Press: Cold Spring Harbor, N.Y.). Most methods of RNA isolation from cells are based on the disruption of the tissue in the presence of protein denaturants to quickly and effectively inactivate RNAses. Isolated total RNA may then be further purified from the protein contaminants and concentrated by selective ethanol precipitations, phenol/chloroform extractions followed by isopropanol precipitation or cesium chloride, lithium chloride or cesium trifluoroacetate gradient centrifugations. Kits are also available to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Qiagen, Inc. (Valencia, Calif.).

In certain embodiments, after extraction, mRNA is amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "Molecular Cloning: A Laboratory Manual", 1989, 2nd Ed., Cold Spring Harbor Laboratory Press: New York; "Short Protocols in Molecular Biology", F. M. Ausubel (Ed.), 2002, 5th Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA, or using thermostable DNApolymerases (such as avian myeloblastosis virus reverse transcriptase or Moloney murine leukemia virus reverse transcriptase).

In general, UDG expression levels in cancer cells, such as those obtained from a subject, can be determined by contacting cancer cells in a biological sample isolated from a subject with binding agents for UDG; detecting, in the sample, the levels of UDG that bind to the binding agents; and comparing the levels of UDG in the sample with the levels of UDG in a control sample. As used herein, the term "binding agent" refers to an entity, such as a polypeptide or antibody that specifically binds to UDG. An entity "specifically binds" to UDG if it reacts/interacts at a detectable level with UDG but does not react/interact detectably with peptides containing unrelated sequences or sequences of different polypeptides.

In certain embodiments, the binding agent is an RNA molecule, or a polypeptide (e.g., a polypeptide that comprises a polypeptide sequence of a protein marker, a peptide variant thereof, or a non-peptide mimetic of such a sequence).

In other embodiments, the binding agent is an antibody specific for UDG. Antibodies for use in the methods include monoclonal and polyclonal antibodies, immunologically active fragments (e.g., Fab or (Fab)2 fragments), antibody heavy chains, humanized antibodies, antibody light chains, and chimeric antibodies. Antibodies, including monoclonal and polyclonal antibodies, fragments and chimeras, may be prepared using methods known in the art (see, for example, R. G. Mage and E. Lamoyi, in "Monoclonal Antibody Production Techniques and Applications", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czemik et al., NeuroNeuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S. Neuberger et al., Nature, 1984, 312: 604-608; S. Takeda et al., Nature, 1985, 314: 452-454). Antibodies to be used in the methods can be purified by methods well known in the art (see, for example, S. A. Minden, "Monoclonal Antibody Purification", 1996, IBC Biomedical Library Series: Southbridge, Mass.). For example, antibodies can be affinity purified by passage over a column to which a protein marker or fragment thereof is bound. The bound antibodies can then be eluted from the column using a buffer with a high salt concentration.

Instead of being prepared, antibodies to be used in the methods described herein may be obtained from scientific or commercial sources.

In certain embodiments, the binding agent is directly or indirectly labeled with a detectable moiety. The role of a detectable agent is to facilitate the measuring of the UDG expression levels by allowing visualization of the complex formed by binding of the binding agent to UDG (or analog or fragment thereof). The detectable agent can be selected such that it generates a signal which can be measured and whose intensity is related (preferably proportional) to the amount of UDG present in the sample being analyzed. Methods for labeling biological molecules such as polypeptides and antibodies are well-known in the art (see, for example, "Affinity Techniques. Enzyme Purification. Part B", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

Any of a wide variety of detectable agents can be used in the methods described herein. Detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In certain embodiments, the binding agents (e.g., antibodies) may be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinylether-maleic acid copolymer, amino acid copolymer, ethylene-maleic acid copolymer, nylon, silk, and the like. Binding agents may be indirectly immobilized using second binding agents specific for the first binding agents (e.g., mouse antibodies specific for the protein markers may be immobilized using sheep anti-mouse IgG Fc fragment specific antibody coated on the carrier or support).

UDG expression levels in the methods described herein may be determined using immunoassays. Examples of such assays are radioimmunoassays, enzyme immunoassays (e.g., ELISA), immunofluorescence immunoprecipitation, latex agglutination, hemagglutination, and histochemical tests, which are conventional methods well-known in the art. As will be appreciated by one skilled in the art, the immunoassay may be competitive or noncompetitive. Methods of detection and quantification of the signal generated by the complex formed by binding of the binding agent with the UDG will depend on the nature of the assay and of the detectable moiety (e.g., fluorescent moiety).

Alternatively, UDG expression levels may be determined using mass spectrometry based methods or image (including use of labeled ligand) based methods known in the art for the detection of proteins. Other suitable methods include proteomics-based methods. Proteomics, which studies the global changes of protein expression in a sample, typically includes the following steps: (I) separation of individual proteins in a sample by electrophoresis (2-D PAGE), (2) identification of individual proteins recovered from the gel (e.g., by mass spectrometry or N-terminal sequencing), and (3) analysis of the data using bioinformatics.

As already mentioned above, the methods described herein may involve determination of the expression levels of a set of nucleic acid molecules comprising polynucleotide sequences coding for UDG. Determination of expression levels of nucleic acid molecules in the practice of the inventive methods may be performed by any method, including, but not limited to, Southern analysis, Northern analysis, polymerase chain reaction (PCR) (see, for example, U.S. Pat. Nos. 4,683,195; 4,683,202, and 6,040,166; "PCR Protocols: A Guide to Methods and Applications", Innis et al. (Eds.), 1990, Academic Press: New York), reverse transcriptase PCR(RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320308), one-sided PCR (Ohara et al., Proc. Natl. Acad. Sci., 1989, 86: 5673-5677), in situ hybridization, Taqman based assays (Holland et al., Proc. Natl. Acad. Sci., 1991, 88:7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan™, and the like.

Nucleic acid probes for use in the detection of polynucleotide sequences in biological samples may be constructed using conventional methods known in the art. Probes may be based on nucleic acid sequences encoding at least 5 sequential amino acids from regions of nucleic acids encoding UDG, and preferably comprise about 15 to about 50 nucleotides. A nucleic acid probe may be labeled with a detectable moiety, as mentioned above in the case of binding agents. The association between the nucleic acid probe and detectable moiety can be covalent or non-covalent. Detectable moieties can be attached directly to nucleic acid probes or indirectly through a linker (E. S. Mansfield et al., Mol. Cell. Probes, 1995, 9: 145-156). Methods for labeling nucleic acid molecules are well-known in the art (for a review of labeling protocols, label detection techniques and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35:135-153).

Nucleic acid probes may be used in hybridization techniques to detect polynucleotides encoding UDG. The technique generally involves contacting an incubating nucleic acid molecules in a biological sample obtained from a subject with the nucleic acid probes under conditions such that specific hybridization takes place between the nucleic acid probes and the complementary sequences in the nucleic acid molecules. After incubation, the non-hybridized nucleic acids are removed, and the presence and amount of nucleic acids that have hybridized to the probes are detected and quantified.

Detection of nucleic acid molecules comprising polynucleotide sequences coding for UDG may involve amplification of specific polynucleotide sequences using an amplification method such as PCR, followed by analysis of the amplified molecules using techniques known in the art. Suitable primers can be routinely designed by one skilled in the art. In order to maximize hybridization under assay conditions, primers and probes employed in the methods of the invention generally have at least 60%, preferably at least 75% and more preferably at least 90% identity to a portion of nucleic acids encoding a protein marker.

Hybridization and amplification techniques described herein may be used to assay qualitative and quantitative aspects of expression of nucleic acid molecules comprising polynucleotide sequences coding for the inventive protein markers.

Alternatively, oligonucleotides or longer fragments derived from nucleic acids encoding each protein marker may be used as targets in a microarray. A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637). Microarray technology allows for the measurement of the steady-state level of large numbers of polynucleotide sequences simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; 1.1. Chen et al., Genomics, 1998, 51: 313324; U.S. Pat. Nos. 5,143,854; 5,445,934; 5,807,522; 5,837,832; 6,040,138; 6,045,996; 6,284,460; and 6,607,885).

Once the expression levels of UDG in the cancer cells has been measured or determined (as described above), the measured level of UDG expression is compared to a control level. The control level can be based upon the level of UDG in a normal cell obtained from a control population (e.g., the general population) or a select population of subjects. For example, the select population may be comprised of apparently healthy subjects or from subjects at risk of developing cancer.

The control level can be related to the value used to characterize the level of UDG expression obtained from the subject. The control level can also take a variety of forms. For example, the control level can be a single cut-off value, such as a median or mean. The control level can be established based upon comparative groups, such as where the level in one defined group is double the level of another defined group.

Control levels of UDG expression in cells, for example, can be obtained (e.g., mean levels, median levels, or "cut-off" levels) by assaying a large sample of subjects in the general population or a select population and then using a statistical model, such as the predictive value method for selecting a positivity criterion or receiver operator characteristic curve that defines optimum specificity (highest true negative rate) and sensitivity (highest true positive rate), as described in Knapp, R. G. and Miller, M. C. (1992): *Clinical Epidemiology and Biostatistics*, William and Wilkins, Harual Publishing Co. (Malvern, Pa.).

Depending upon the level or value of measured UDG when compared to the control level, a determination can be made as to whether the p53 mutant or deficient cancer cells or p53 related cancer of the subject is more or less susceptible, sensitive, and/or resistance to treatment with an antimetabolite. A measured or determined expression level of UDG for the p53 related cancer higher or increased compared to the control level identifies the p53 related cancer as being less susceptible to treatment with the antimetabolite agent administered alone and hence the antimetabolite agent as being less effective in treating the cancer. In contrast, a measured or determined expression level of UDG less than the control level identifies the p53 related cancer as being more susceptible to treatment with the antimetabolite agent administered alone and hence the antimetabolite agent as being more effective in treating the cancer.

By determining the efficacy of an antimetabolite agent, such as the thymidylate synthase inhibitor floxuridine (5FdU), to treating p53 related cancer and/or susceptibility, sensitivity, and/or resistance of the p53 mutant or deficient cancer cell to the antimetabolite, skilled physicians may select and prescribe treatments adapted to each individual patient with increased efficiency. In some embodiments, a method of treating p53 related cancer with an antimetabolite can include first determining the level of UDG expression of cancer cells of a subject diagnosed with a p53 related cancer and then administering an antimetabolite agent alone or in combination with a BER inhibitor, such as an AP endonuclease inhibitor, or UDG inhibitor depending on the determined or measured level of UDG expression.

In some embodiments, an antimetabolite agent can be administered alone or without a UDG induced BER pathway inhibitor, such as an AP endonuclease inhibitor or UDG inhibitor when the level of UDG expression for the cancer is lower than a control value in order to mitigate side-effect burdens on the patient being treated.

The antimetabolite agent can include agents, compounds, or small molecules that induce or promote incorporation of a UDG substrate, such as uracil, into DNA of cancer cells of the subject. Exemplary antimetabolite agents include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine (5-fluorodeoxyuridine, 5FdU), fludarabine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pemetrexed pentostatin, piritrexim, plicamycin, Asahi Chemical PL-AC, raltitrexed stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

In some embodiments, the antimetabolite agent can be a thymidylate synthase (TS) inhibitor that when administered to a cancer cell of a subject promotes incorporation of a UDG substrate such as uracil, into the DNA of the cell. In a particular embodiment, the antimetabolite TS inhibitor is a fluoropyridine selected from the group consisting of capecitabine, floxuridine (5-fluorodeoxyuridine or 5FdU), fluorouracil (5-FU) and derivatives of 5-fluorouracil with anti-cancer activity, such as those described in U.S. Pat. No. 4,336,381. Further 5-FU derivatives have been described in the following patents listed in JP 50-50383, JP 50-50384, JP 50-64281, JP 51-146482, and JP 53-84981 hereby individually incorporated by reference herein. Other such TS inhibitors are known in the art (see Theti et al. Cancer res. (2003) 63:3612-3618; Ackland et al., Cancer Chemother Biol Response modif. (2002) 20:1-36; Pawelczak et al, Act Biochim Pol. (2002) 49:407-420; Chu et al. Cancer Chemother. Pharmacol. (2003) 52 supl 1:80-89; Wang et al. Leuk lymphoma. (2003) 44(6):1027-1035; Van Der Laan et al., Int. J. Cancer (1992) 51:909-914; Papamichael, Stem Cell. (2000) 18:166-175; Prezioso, et al., Cancer chemother. Pharmacol. (1992) 30:394-400; Ismail et al., Cancer Chemother Biol response Modif. (2001) 19:1-19). In an exemplary embodiment, the TS inhibitor is floxuridine (5FdU).

In other embodiments, the antimetabolite agent can be an antifolate agent that when administered to a cancer cell of a subject blocks TS and promotes incorporation of a UDG substrate into the DNA of the cell. An example of an antifolate agent is pemetrexed. Pemetrexed inhibits several key folate-dependant enzymes in the thymidine and purine biosynthetic pathways, including thymidylate synthase, dihydrofolate reductase, and glycinamide ribonucleotide formyltransferase. As an analogue of methylenetetrahydrofolate, pemetrexed directly blocks dTMP production by depleting tetrahydrofolate pools required for TS. In comparison to other anti-metabolites, pemetrexed is the most potent inducer of uracil incorporation into DNA. Additional agents capable of inhibiting TS for use in methods described herein may be selected from the group consisting of, but not limited to, Raltitrexed (also referred to as Tomudex, TDX, or ZD 1694), nolatrexed, ZD9331, GS7904L, BGC 945, OSI-7904L UFT, S-1,5-ethynyluracil, pemetrexed, nolatrexed, trimetrexate, LU231514, edatrexate, GW1843, Leucovorin, Levimosole, methotrexate, PDX, 10-EdAM, ICI-198,583, DDATHF and thymydilate synthase inhibitors other than anti-folate compounds such as CB300638, 4-S-CAP, N-ac-4-S-CAP.

In still other embodiments, the antimetabolite agent can be a nucleoside analogue that when administered to a cancer cell of a subject promotes incorporation of a UDG substrate into the DNA of the cell. In some examples, the nucleoside analogue can be 2-Fluoroadenosine-5'-phosphate or fludarabine (F-ara-A). Fludarabine is one of the most active agents in the treatment of chronic lymphocytic leukemia. The compound acts by inhibiting DNA synthesis. Treatment of cells with fludarabine is associated with the accumulation of cells at the G1/S phase boundary and in S phase; thus, it is a cell cycle S phase-specific drug. Incorporation of the active metabolite, F-araATP, retards DNA chain elongation. Fludarabine is also a potent inhibitor of ribonucleotide reductase, the key enzyme responsible for the formation of dATP.

In some embodiments, an antimetabolite agent can be administered in combination with an AP endonuclease to promote or enhance the cytotoxicity of the antimetabolite agent when it is determined that the expression level of UDG for the p53 related cancer is higher than the control level. As discussed above, administration of an antimetabolite in combination with an AP endonuclease inhibitor to a p53 mutant or deficient cancer cell can enhance antimetabolite induced cell death by binding of the AP endonuclease inhibitor to AP sites that are excised by DNA glycosylases including UDG. This enhances the cytotoxicity of the antimetabolite agents by further inhibition of the BER pathway and allows effective treatment of cancers that express high levels of UDG that were previously found to be resistant to treatment with antimetabolite agents.

In some embodiments, the AP endonuclease inhibitor that potentiates the cytotoxicity of the antimetabolite agent can be a small molecule compound with a primary amine group that forms a covalent linkage with and/or binds to an aldehyde group of an AP site induced by the antimetabolite agent. In single-nucleotide BER, the deoxyribose phosphate (dRP) in the abasic site is removed by the lyase activity of DNA pol β. Binding of the AP endonuclease inhibitor to an aldehyde group can structurally alter the AP site so that AP endonuclease does not recognize the modified AP site and/or prevent AP endonuclease-mediated cleavage of phosphodiester bonds, thus blocking single nucleotide BER.

In some embodiments, the reaction of the AP endonuclease inhibitor with the AP site aldehyde group in the p53 mutant or deficient cancer cells can be faster than AP endonuclease to inhibit repair of DNA. Advantageously, administration of the AP endonuclease inhibitor in combination with the antimetabolite agent to p53 mutant or deficient tumor cells can bypass other resistance factors, such as MMR defects and high MGMT activity in the tumor cells.

In some embodiments, the AP endonuclease inhibitor can be an aminooxy small molecule that can react with an AP site faster than AP endonuclease. One example of an aminooxy compound that that can react with an AP site faster than AP endonuclease is methoxyamine (MX) or salts thereof. Methoxyamine when administered in combination with an antimetabolite agent, such as pemetrexed, to a subject with cancer can potentiate the anticancer effect of the antimetabolite agent without additive systemic toxicity.

In other embodiments the AP endonuclease inhibitor can be a small molecule having the formula V:

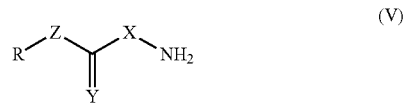

(V)

wherein X is O or NH,
Y is O, S, or NH,
Z is absent or represents O, S, or NH,
R represents a hydrogen or a hydrocarbon moiety, and pharmaceutically acceptable salts thereof.

Other examples of small molecules primary amine compounds that can bind to AP sites and prevent APE-mediated cleavage of phosphodiester bonds include O-benzylhydroxylamine; ethyl aminooxyacetate; aminooxyacetic acid; ethyl aminooxyacetate; $H_2N-OCHMeCO_2H$; carboxymethoxyamine; aminooxyacetic acid; $HN=C(NH_2)SCH_2CH_2ONH_2$; $H_2N-O(CH_2)_3SC(NH_2)=NH$; $MeOC(O)CH(NH_2)CH_2O-NH_2$; $H_2NOCH_2CH(NH_2)CO_2H$; canaline; $H_2N-O(CH_2)_4O-NH_2$; O-(p-nitrobenzyl)hydroxylamine; 2-amino-4-(aminooxymethyl)thiazole; 4-(aminooxymethyl)thiazole; O,O'-(o-phenylenedimethylene)dihydroxylamine; 2,4-dinitrophenoxyamine; O,O'-(m-phenylenedimethylene)dihydroxylamine; O,O'-(p-phenylenedimethylene)dihydroxylamine; $H_2C=CHCH_2O-NH_2$; $H_2N-O(CH_2)_4O-NH_2$; $H_3C(CH_2)_{15}O-NH_2$, 2,2'-(1,2-ethanediyl)bis(3-aminooxy)butenedioic acid dimethyl diethyl ester; compounds having any of the following structures:

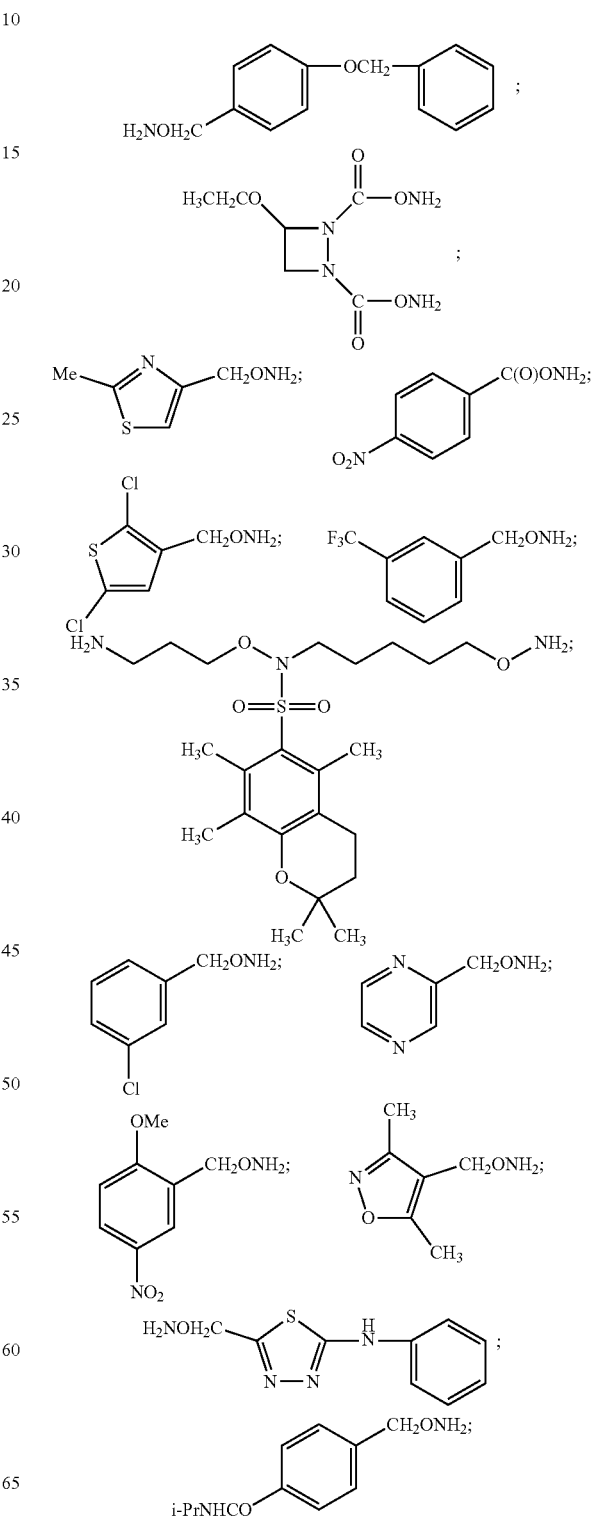

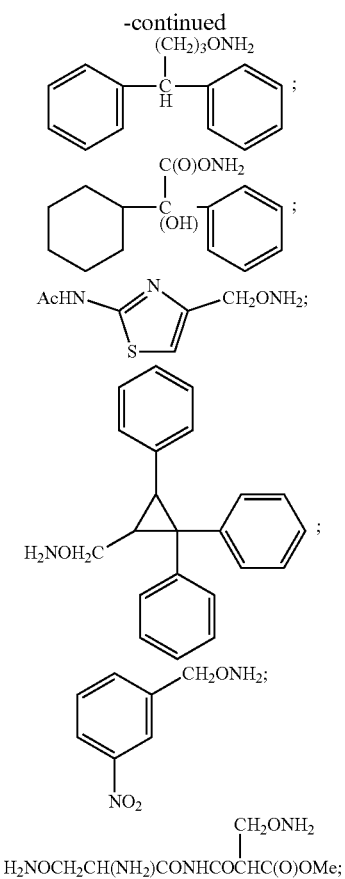

and pharmaceutically acceptable salts of any of these compounds.

Additional exemplary small molecule inhibitors of APE DNA repair for use in a method described herein as an AP endonuclease inhibitor are described in Al-Safi et al., (Current Molecular Pharmacology, 2012, 5, 14-35), the entirety of which is incorporated herein by reference. In some embodiments, the AP endonuclease inhibitor can be selected from lucanthone and CRT0044876 (7-nitroindole-2-carboxylic acid).

Still other examples of small molecule primary amine compounds that can bind to AP sites and prevent APE-mediated cleavage of phosphodiester bonds for use in a method describe herein as an AP endonuclease inhibitor can be identified using a high-throughput screening assay described in U.S. Pat. Nos. 8,367,332, 8,324,282, 6,635,677, and 6,465,448.

In some embodiments, the antimetabolite agent can be administered in combination with a UDG inhibitor to promote or enhance the cytotoxicity of the antimetabolite agent when it is determined that the expression level of UDG for the p53 related cancer in a subject is higher than the control level. In some embodiments, an UDG inhibitor is administered in an amount efficient to enhance or increase the effect of an antimetabolite agent.

In other embodiments, the endogenous UDG gene product or a UDG regulatory element gene product is modified through the use of a gene silencing agent that reduces or inhibits expression of UDG or a UDG regulatory element that promotes UDG expression, in p53 mutant or deficient cancer tissue or cancer cells of a subject in need thereof. "Expression", means the overall flow of information from a gene to produce a gene product (typically a protein, optionally post-translationally modified or a functional/structural RNA).

In some embodiments, the agent can include an RNAi construct that inhibits or reduces expression of the UDG expression in a cell. RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner.

As used herein, the term "dsRNA" refers to siRNA molecules or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the application describes other forms of expression vectors that serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, embodiments tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA Likewise, bases may be modified to block the activity of adenosine deaminase. The RNAi construct may be produced enzymatically or by partial/total organic synthesis, a modified ribonucleotide can be introduced by in vitro enzymatic or organic synthesis.

Methods of chemically modifying RNA molecules can be adapted for modifying RNAi constructs (see for example, *Nucleic Acids Res*, 25:776-780; *J Mol Recog* 7:89-98; *Nucleic Acids Res* 23:2661-2668; Antisense *Nucleic Acid Drug Dev* 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount, which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules described herein can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (*Proc Natl Acad Sci USA*, 98:9742-9747; *EMBO J*, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain embodiments, the RNAi construct is in the form of a hairpin structure (named as hairpin RNA or shRNA). The hairpin RNAs can be synthesized exogenously or can be formed by transcribing from RNA polymerase III promoters in vivo. Examples of making and using such hairpin RNAs for gene silencing in mammalian cells are described in, for example, *Genes Dev*, 2002, 16:948-58; *Nature*, 2002, 418: 38-9; *RNA*, 2002, 8:842-50; and *Proc Natl Acad Sci*, 2002, 99:6047-52. Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an example of a vector for bi-directional transcription of a transgene to yield both sense and antisense RNA transcripts of the same transgene in a eukaryotic cell. Accordingly, certain embodiments provide a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

In some embodiments, a lentiviral vector can be used for the long-term expression of a siRNA, such as a short-hairpin RNA (shRNA), to knockdown expression of the RPTP in a cancer cell. Although there have been some safety concerns about the use of lentiviral vectors for gene therapy, self-inactivating lentiviral vectors are considered good candidates for gene therapy as they readily transfect mammalian cells.

By way of example, short-hairpin RNA (shRNA) down regulation of the UDG expression can be created using OligoEngene software (OligoEngine, Seattle, Wash.) to identify sequences as targets of siRNA. The oligo sequences can be annealed and ligated into linearized pSUPER RNAi vector (OligoEngine, Seattle, Wash.) and transformed in *E coli* strain DH5α cells. After positive clones are selected, plasmid can be transfected into 293T cells by calcium precipitation and selected with puromycin. The viral supernatant collected containing shRNA can then be used to infect mammalian cancer cells in accordance with a method described herein in order to down regulate the UDG gene product thereby decreasing UDG expression level in the cells. An exemplary UDG shRNA clone can include the UDG shRNA clone NM_003362.2-656s21c1.

In another embodiment, the gene silencing agent that reduces or inhibits expression of UDG or a UDG regulatory element that promotes UDG expression can include antisense oligonucleotides (ASOs). Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

The binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein (e.g., UDG).

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups, such as peptides (e.g., for targeting host cell receptors), or agents facilitating transport across the cell membrane (see, e.g., *Proc Natl Acad Sci* 86:6553-6556; *Proc Natl Acad Sci* 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., *BioTechniques* 6:958-976) or intercalating agents. (See, e.g., *Pharm Res* 5:539-549). To this end, the oligonucleotide may be conjugated or coupled to another molecule.

Oligonucleotides described herein may be synthesized by standard methods known in the art, e.g., by use of an automated DNA synthesizer (such as are commercially available from Bio search, Applied Biosystems, etc.). As examples, phosphorothioate oligonucleotides may be synthesized by the method of Stein et al. (*Nucl. Acids Res.* 16:3209), methylphosphonate oligonucleotides can be prepared by use of controlled pore glass polymer supports (*Proc Natl Acad Sci* 85:7448-7451).

The selection of an appropriate oligonucleotide can be performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

A number of methods have been developed for delivering antisense DNA or RNA to cells; e.g., antisense molecules can be injected directly into the tumor tissue site, or modified antisense molecules, designed to target the desired cancer cells (e.g., antisense linked to peptides or antibodies that specifically bind receptors or antigens expressed on the target cell surface) can be administered systematically.

However, it may be difficult to achieve intracellular concentrations of the antisense oligonucleotide sufficient to suppress translation on endogenous mRNAs in certain instances. Therefore, another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the antisense RNA can be by a promoter known in the art to act in mammalian, preferably human cells. Such promoters can be inducible or constitutive. Such promoters include but are not limited to: the SV40 early promoter region (*Nature* 290:304-310), the promoter contained in the 3' long terminal repeat of Rous sarcoma virus (*Cell* 22:787-797), the herpes thymidine kinase promoter (*Proc Natl Acad Sci* 78:1441-1445), the regulatory sequences of the metallothionein gene (*Nature* 296:39-42), etc. A type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

In some embodiments, the antimetabolite agent can be administered to an individual in combination with the AP endonuclease inhibitor or UDG inhibitor. For example, the antimetabolite agent and AP endonuclease inhibitor can be administered to an individual together in a parenteral formulation. Alternatively, the antimetabolite agent and AP endonuclease inhibitor can be administered to an individual together in an oral formulation, such as a solid dosage formulation.

In some embodiments, the antimetabolite agent and AP endonuclease inhibitor or UDG inhibitor can be administered to an individual sequentially, where the individual is first given the antimetabolite agent and then given the AP endonuclease inhibitor or UDG inhibitor. For example, the individual can be given the antimetabolite agent in a parenteral formulation, such as an intravenous formulation, or an oral formulation, such as a solid dosage formulation and then given the AP endonuclease inhibitor or UDG inhibitor in a parenteral formulation, such as an intravenous formulation, or an oral formulation, such as a solid dosage formulation.

Alternatively, in some embodiments, the antimetabolite agent and AP endonuclease inhibitor or UDG inhibitor can be administered to an individual sequentially, where the individual is first given the AP endonuclease inhibitor or UDG inhibitor and then given the antimetabolite agent. For example, the individual can be given the AP endonuclease inhibitor or UDG inhibitor in a parenteral formulation, such as an intravenous formulation, or an oral formulation, such as a solid dosage formulation and then given the antimetabolite agent in a parenteral formulation, such as an intravenous formulation, or an oral formulation, such as a solid dosage formulation.

In some embodiments, the antimetabolite agent and the AP endonuclease inhibitor or UDG inhibitor can create an anticancer effect greater than that of the separate anticancer effects of the individual agents. For example, the combined anticancer effect of the antimetabolite agent and the AP endonuclease inhibitor or UDG inhibitor can have a synergistic effect that is found to be greater than the added anticancer effect of the antimetabolite agent and AP endonuclease inhibitor when used individually.

In certain embodiments, an antimetabolite agent, such as the thymidylate synthase inhibitor 5FdU, that induces incorporation of uracil into DNA of the p53 related cancer can be administered in combination with an AP endonuclease inhibitor (e.g methoxyamine) or UDG inhibitor, after it is determined that cancer of subject has an increased level of UDG expression compared to a control level.

In some embodiments, the antimetabolite agent can be administered in a dose of from about 10 mg/m² to about 5,000 mg/m² body surface area. For example, the dose can be from about 20 mg/m² to about 200 mg/m² body surface area; the dose can be from about 150 mg/m² to about 500 mg/m² body surface area; the dose can be from about 400 mg/m² to about 1000 mg/m² body surface area; the dose can be from about 900 mg/m² to about 5,000 mg/m² body surface area; the dose can be from about 200 mg/m² to about 1,000 mg/m² body surface area; or the dose can be from about 500 mg/m² to about 600 mg/m² body surface area. In some embodiments, the antimetabolite agent can be pemetrexed and pharmaceutically acceptable salts thereof.

In some embodiments, the ratio of AP endonuclease inhibitor to antimetabolite agent can be from about 1 to about 1:10000. For example, ratio of AP endonuclease inhibitor to antimetabolite agent can be from about 1:2 to about 1:100; the ratio of AP endonuclease inhibitor to antimetabolite agent can be from about 1:50 to about 1:500; the ratio of AP endonuclease inhibitor to antimetabolite agent can be from about 1:450 to about 1:10000; the ratio of AP endonuclease inhibitor to antimetabolite agent can be from about 1:5 to about 1:500; the ratio of AP endonuclease inhibitor to antimetabolite agent can be from about 1:10 to about 1:50; the ratio of AP endonuclease inhibitor to antimetabolite agent can be from about 1:15 to about 1:40; or the ratio of AP endonuclease inhibitor to antimetabolite agent can be from about 1:20 to about 1:30.

In some embodiments, an AP endonuclease inhibitor is administered in an amount efficient to enhance or increase the effect of an antimetabolite agent.

Candidate combinations of antimetabolite agents and AP endonuclease inhibitors or UDG inhibitors may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al, Proc. Natl. Acad. Sci. USA, 92:3439-3443 (1995)). Candidate agents can be used in these animal models to determine if a candidate agent(s) increases antimetabolite (e.g., thymidylate synthase inhibitor) anti-cancer efficacy, decreases one or more of the symptoms associated with the p53 related cancer, including, for instance, cancer metastasis, cancer cell motility, cancer cell invasiveness, or combinations thereof.

In other embodiments, the antimetabolite agent or combination of antimetabolite agent and AP endonuclease inhibitor or UDG inhibitor can be administered to subject in combination with at least one other BER inhibitor. The at least one other BER inhibitor can include, for example, a PARP inhibitor. Examples of PARP inhibitors are 4-amino-1,8-naphthalimide (ANI), PD128763, 3-AB, 6-AN, and 8-hydroxy-2-methyl-quinazolin-4-[$^3$H]one (NU-1025).

Other examples of BER inhibitors that can be administered to the subject in combination with the antimetabolite agent and or AP endonuclease inhibitor include DNA polymerase inhibitors (e.g., DNA polymerase β, γ or ε, such as prunasin, aphidicolin, 2',3'-dideoxycytidine triphosphate (ddCTP), 2',3'-dideoxythymidine triphosphate (ddTTP), 2',3'-dideoxyadenosine triphosphate (ddATP), 2',3'-dideoxyguanosine triphosphate (ddGTP), 1-beta-D-arabinofuranosylcytosine (Ara-C), caffeine, arabinocytidine, and bleomycin.

Still other examples of BER inhibitors include DNA ligase inhibitors (e.g., DNA ligase I, II, or III), such as ursolic and oleanolic acids, aleuritolic acid, protolichesterinic acid, swertifrancheside, fulvoplumierin, fagaronine chloride, and bleomycin. XRCC1 is the protein partner of DNA ligase III, and inhibitors of XRCC1, such as 3-AB, are useful as BER inhibitors as well.

Further examples of BER inhibitors include topoisomerase II inhibitors. Topoisomerase inhibitors induce DNA cleavage and other chromosomal aberrations, including sister chromatid exchanges. Compounds useful as BER inhibitors also include topoisomerase II inhibitors, such as etoposide (VP-16, VP-16-123), meso-4,4'-(2,3-butanediyl)-bis-(2,6-piperazinedione) (ICRF-193, a bisdioxopiperazine), doxorubicin (DOX), L amsacrine (4',9-acridinylaminomethanesulfon-m-anisidide; mAMSA), pazelliptine, nalidixic acid, oxolinic acid, novobiocin, coumermycin A1, fostriecin, teniposide, mitoxantrone, daunorubicin, N-[2-dimethylamino)ethyl] acridine-4-carboxamide (DACA), merbarone, quinacrine, ellipticines, epipodophyllotoxins, ethidium bromide, epirubicin, pirarubicin, 3'-deamino-3'-morpholino-13-deoxo-10-hydroxy caminomycin; 2",3"-bis pentafluorophenoxyacetyl-4',6'-ethylidene-beta-D glucoside of 4'-phosphate-4'-dimethylepipodophyollotoxin 2N-methyl glucamine salt (F11782; a fluorinated lipophilic epipodophylloid), adriamycin, actinomycin D, anthracyclines (such as 9-aminoanthracycline), and pyrazoloacridine (PZA). Topoisomerase I inhibitors, such as camptothecin and topotecan can also be used as BER inhibitors.

In some embodiments, other enzyme inhibitors, whether known in the art or hereafter identified, as well as inhibitors of other elements of the BER pathway, such as DNA alkyltransferase, may be employed in compositions and methods without departing from the scope and spirit of the present embodiments.

In still other embodiments, the antimetabolite agent or combination of antimetabolite agent and AP endonuclease inhibitor or UDG inhibitor can be administered to subject in combination with at least one other anticancer agent that induces formation of AP sites. Anticancer agents that induce the formation of AP sites include intercalating agents, such as bleomycin, adriamycin, quinacrine, echinomycin (a quinoxaline antibiotic), and anthrapyrazoles.

Radiation, such as gamma radiation, UVA, and UVB, can be used to generate AP sites. Ultraviolet light is absorbed in DNA with the formation of UV-specific di-pyrimidine photoproducts. Exposure to gamma irradiation, UVA, and UVB can induce damaged pyrimidine photodimers Anticancer agents that induce the formation of AP sites can also include DNA oxidizing agents, such as hydrogen peroxide.

Anticancer agents that induce the formation of AP sites can further include alkylating agents, such as temozolomide (TMZ), 1,3-bis(2-chloroethyl)-1-nitrosourea (BCNU), $MeOSO_2(CH_2)_2$-lexitropsin (Me-Lex), cis-diamminedichloroplatinum II (cisplat; cis-DDP), mitomycin bioreductive alkylating agents, quinones, streptozotocin, cyclophosphamide, nitrogen mustard family members such as chlorambucil, pentostatin (and related purine analogs), fludarabine, bendamustine hydrochloride, chloroethylating nitrosoureas (e.g., lomustine, fotemustine, cystemustine), dacarbazine (DTIC), and procarbazine. In certain embodiments, the alkylating agent is a nitrosoruea, such as a mustine.

Alkylating agents can function by adding methyl groups to DNA, cross-linking macromolecules essential for cell division, and linking guanine bases in DNA through their $N^7$ atoms. Both inter- and intra-strand cross-links can be mediated by alkylating agents. Inter-strand cross-links prevent the separation of the DNA strands necessary for cell division, and by being more difficult to repair, constitute the more lethal lesion.

In certain embodiments, the anticancer agent is selected from radiosensitizers such as 5-iodo-2'-deoxyuridine (IUdR), 6-thioguanine, hypoxanthine, uracil, ecteinascidin-743, and camptothecin and analogs thereof.

In certain embodiments, the anticancer agent is not temozolomide. In certain embodiments, the anticancer agent is not BCNU. In certain embodiments, the anticancer agent is not PE128723, 6-AN, 3-AB, BCNU, or temozolomide It will be appreciated that compositions or formulations provided herein may be in any form, which allows for the composition to be administered to a patient. For example, the composition may be in the form of a solid, liquid or gas (e.g., aerosol). Other routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavemous, intrathecal, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

Pharmaceutical compositions can include physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example, dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries, which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Additional therapeutic or diagnostic agents may be incorporated into the pharmaceutical compositions. Alternatively or additionally, pharmaceutical compositions may be combined with other compositions that contain other therapeutic or diagnostic agents.

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the invention into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 10 microgram/kg and 100 mg/kg body weight, preferably between about 100 microgram/kg and 10 mg/kg body weight. Alternatively, dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

The present invention is illustrated by the following examples. It is to be understood that the particular examples, materials, amounts, and procedures are to be interpreted broadly in accordance with the scope and spirit of the invention as set forth herein.

Example 1

Inhibition of Uracil DNA Glycosylase Sensitizes Cancer Cells to 5-Fluorodeoxyuridine Through Replication Fork Collapse-Induced DNA Damage Materials and Methods Cell Lines and Drugs DLD1 colon cancer cells were purchased from American Type Culture Collection, and HEC1A cells were a gift from Dr. Sanford Markowitz at Case Western Reserve University. Cells were maintained in growth medium DMEM supplemented with 10% dialyzed fetal bovine serum containing penicillin and streptomycin. Cells were incubated at 37° C. in a humidified atmosphere of 5% $CO_2$. Drugs and chemicals used in this study are: 5-fluorodeoxyuridine (Sigma Aldrich), thymidine (Sigma Aldrich), pemetrexed (LC laboratories), temozolomide (Ochem Inc), cisplatin and doxorubicin.

Lentiviral shRNA Knockdown

UDG knockdown was performed via shRNA transduction with validated clone from Sigma-Aldrich. The ID of UDG shRNA clone is NM_003362.2-656s21c1. A non-targeted scramble control shRNA clone (Sigma-Aldrich) was also used. Transfection of shRNA clones was performed according to manufacturer's specifications from Lipofectamine 2000 (Invitrogen). Lentiviral particles were produced via HEK293 cells, and targeted cells were infected and selected with puromycin. The stable UDG knockdown levels were verified for q-PCR and western blot analysis.

Glycosylase Activity Assay

UDG activity was determined by using a green emitting Alexa 532 labeled 40-mer duplex DNA containing a U:A base pair that was synthesized by IDT with the sequence:

(SEQ ID NO: 1)
5'-TCCTGGGTGACAAAGCUAAACACTGTCTC CAAAAAAATT
[Alexa]-3'

(SEQ ID NO: 2)
3'-AGGACCCACTGTTTCGATTTGTGACAGAG GTTTTTTTTAA-5'

For the reaction, 5 pmol (10 µL) diluted DNA aliquots were incubated with either purified enzymes UDG and APE (New England Biolabs) sequentially or 10 µg nuclear extracts isolated from cells at 37° C. for 20 minutes. Nuclear extracts were prepared by using the NucBuster isolation procedure (EMD Bioscience Calbiochem). Reaction products were resolved in the dark by electrophoresis on 20% denaturing polyacrylamide gels (5.3 g urea, 5.0 mL 40% acrylamide, 2.3 mL 5×TBE buffer, 200 µL 10% APS, and 20 µL TEMED). Gels were visualized by a Typhoon Tri+ Variable Mode Imager (Amersham Biosciences).

Apyrimidinic (AP) Site Detection

The amount of cellular AP sites was assessed as we previously described by using a NIR cyanine-based AP site probe. Briefly, following 5-FdU exposure, genomic DNA was obtained from phenol-chloroform extraction, dissolved in 1×UDG reaction buffer (20 mM Tris-HCl, 1 mM EDTA and 1 mM dithiothreitol, pH 8.0), and incubated with either the UDG enzyme (1 µL, 5 units) or 1 µL UDG storage buffer (10 mM Tris-HCl, 50 mM KCl, 1 mM DTT, 0.1 mM EDTA, 0.1 mg/ml BSA, 50% Glycerol, pH 7.4) as a vehicle control at 37° C. for 1 h. After the reaction, AP site probe with a final concentration of 25 µM was added and incubated at 37° C. for 1 h. Following incubation, extracted DNA was precipitated, and the supernatant was discarded. DNA pellets were resuspended in $H_2O$, and DNA concentrations were measured and adjusted. The fluorescence intensities of each sample were analyzed with 760 nm excitation and emission scan of 790-847 nm.

Quantitative Determination of Uracil and 5-FU Incorporated in Cellular DNA by LC-MS/MS Genomic DNA was extracted from cells treated with 5-FdU via phenol-chloroform mixture. 80 µg of DNA sample was dissolved in 1×UDG reaction buffer (20 mM Tris-HCl, 1 mM EDTA and 1 mM dithiothreitol, pH 8.0) and incubated with UDG enzyme (1 µL, 5 units) for 1 h at 37° C. For LC-MS/MS analysis of DNA-incorporated uracil and 5-FU, 75 µL of the enzyme reaction mixture was obtained, and uracil-1,3-$^{15}N_2$ was used as the internal standard (Sigma-Aldrich). All uracil and 5-FU standards, internal standard, and QC samples were prepared in 1×UDG reaction buffer. The separation of analytes were achieved by a Shimadzu LC-20AD HPLC system with a Shimadzu SIL-20AC autosampler (Shimadzu) on a Waters Xbridge HILIC pre-column (2.1×10 mm, 3.5 µm) and a Xbridge HILIC column (2.1×100 mm, 3.5 µm) (Waters Corporation) using a mobile phase consisting of 87.5% acetonitrile and 12.5% 10 mM ammonium formate at a flow rate of 0.200 mL/min. Quantitation of the analytes was accomplished by a AB Sciex API 3200 triple quadrupole tandem mass spectrometer (AB Sciex), which was operated in the negative multiple-reaction-monitoring (MRM) mode with mass transitions of m/z 110.8>42.0 for uracil, m/z 112.9>43.0 for uracil-1,3-$^{15}N_2$ and m/z 129.0>42.0 for 5-FU. This method has lower limits of quantitation of 2.50 ng/mL and linear calibration ranges up to 500 ng/mL for both uracil and 5-FU with a sample injection volume of 15 µL, as well as a total analysis time of 6 min.

Clonergic Survival Assay

DLD1 (200 cells/well) or HEC1A (300 cells/well) cells were plated in 6-well culture dishes and allowed to adhere for 16 h. Cells were treated with drug for 24 h, gently washed twice with 1×PBS, and incubated with fresh media for at least 10 days to allow individual colonies to form. Colonies were stained with methylene blue, and only colonies containing ≥50 cells were counted. The percentage of survival was determined relative to untreated control averaged over 3 independent experiments.

Cell Cycle and Bromo-Deoxyuridine (BrdU)/PI Labeling Analysis

For cell cycle analysis, DLD1 cells were synchronize by serum starvation for 48 h and released in fresh media for 16 h. The cells were then treated with 100 nM 5-FdU for 4, 8, 12, 20, 24, 28, 32, 36, 48, 72, and 96 h. At each time point, cells were harvested and fixed with methanol. Fixed cells were incubated with DNase-free RNaseA (Roche) and stained with 50 µg/mL PI solution (Sigma-Aldrich). For BrdU/PI labeling analysis, cells were treated with 100 nM 5-FdU for 24 h and pulsed with 10 µM BrdU (BD Biosciences Pharmingen, BrdU Flow Kit) for 45 minutes before collecting cells. According to manufacturer's instructions from BD Biosciences Pharmingen, cells were fixed, treated with DNAse for 1 h at 37° C., stained with FITC anti-BrdU for 20 minutes, and incubated with PI staining solution (50 µg/mL PI, 10 mM Tris-HCl pH 7.5, 5 mM MgCl2, 10 µg/mL DNase-free RNaseA) for 30 minutes at 37° C. For both assays, cells were analyzed on a BD LSRII instrument.

DNA Fiber Assays

DNA fiber analysis was performed as described by Han et al. (*J. Biol.* (2015) 290:12370-8). Cells treated with 100 nM 5-FdU for 24 h were pulse-labeled with 100 µM chlorodeoxyuridine (CldU) for 20 minutes, washed with PBS, and 25 µM Iododeoxyuridine (IdU) for 20 minutes. Cells were collected in PBS, and 2.5 µL of cell suspension was dropped on glass slide. 7.5 µL of lysis buffer (0.5% SDS, 200 mM Tris-HCl pH 7.4, 50 mM EDTA) was dropped on the cell suspension and lysis for 10 minutes. Slides were then tilted at 15° to spread the suspension and placed horizontally to allow air-dry. After drying, slides were fixed in 3:1 methanol:acetic acid for 15 minutes, washed with water, and placed at −20° C. overnight. Slides were then treated with 2.5 M HCl for 1 h, washed with PBS containing 0.1% Tween-20, washed twice with PBS, blocked in PBS containing 5% BSA and 0.1% Tween 20 for 20 minutes, and rinsed with PBS three times. After washing, 100 µL primary antibodies: mouse anti-BrdU/IdU (Becton Dickinson, 1:100) and rat anti-BrdU/CIdU (AbD Serotec, 1:400) diluted in PBS containing 5% BSA and 0.1% were added to incubate in a humid chamber for 4-6 h. After incubation, slides were washed with PBS three times, incubated with secondary fluorescent antibodies: sheep anti-mouse Alexa Fluor 488 (Life technologies) and donkey anti-rat Alexa Fluor 594 (Life technologies) diluted in PBS containing 5% BSA for 1 h. Slides were washed with PBS three times and mounted with Vectashield mounting medium. Image acquisition was performed on a Leica laser microscope. DNA fiber length was measured by using ImageJ software (NCI/NIH).

Immunofluorescence Staining

Cells cultured on glass coverslips were treated with 5-FdU in the presence or absence of 10 µM caspase inhibitor Q-VD-OPH (BioVision Inc). Cells were fixed in 3.7% formaldehyde for 10 minutes, blocked with PBS containing 10% FBS and 0.1% Triton X-100 for 20 minutes, washed with PBS three times, and incubated with primary anti-γH2AX antibody (Millipore, dilution: 1:150) in PBS containing 0.1% Triton X-100 at 4° C. overnight. The cells were then washed with PBS three times, incubated with secondary antibodies (Alexa Fluor 594, Life Technologies; dilution: 1:400) in PBS containing 0.1% Triton X-100 for 1 h, and washed with PBS three times. The slides were mounted with antifade solution with DAPI (Cell Signaling) and visualized on a Leica laser microscope.

Western Blots and qPCR

Western blots were performed as described in Yan et al. (*Clin Cancer Res*. (2007) 13:1532-39). Antibodies used were as follows: Anti-UDG (FL-313) (Santa Cruz Biotechnology), anti-Cleaved PARP (Asp214)(19F4) (Cell Signaling), and anti-α-Tubulin (Calbiochem). For quantitative RT-PCR, total RNA from cells was extracted using RNeasy Plus Mini Kit (Qiagen), and cDNA synthesis was carried out by using SuperScript III First Strand Kit (Life Technologies). Q-PCR was performed with validated TaqMAN MGB FAM™ dye labeled probes (Applied Biosystems) for UDG on an ABI 7500 Fast Real-time PCR System (Applied Biosystems). β-Actin was used as an endogenous control, and relative gene expression was calculated as $2^{-\Delta\Delta Ct}$.

Statistics

Statistical significance between two treatment groups was determined by unpaired 2-tailed student's t test. Significance was assigned for a P-value <0.05. Standard software Graph-Pad Prism (San Diego, Calif., USA) and Excel 2013 (Microsoft Corp., Redmond, Wash.) were used for all statistical analysis.

Results

UDG Removes Uracil and 5-FU Incorporated into DNA Following 5-FdU Treatment

Studies have demonstrated that the nuclear form of UDG is responsible for the removal of uracil and 5-FU from DNA in vitro in comparison with other glycosylases. To confirm this activity of UDG in vivo, we generated DLD1 colon cancer cells whose expression of UDG was depleted by shRNA (FIGS. 1A, 1B). We then determined if the enzymatic activity of UDG is reduced in UDG depleted cells by the glycosylase activity assay. In brief, we incubated isolated nuclear extracts with a fluorescently tagged 40-mer DNA duplex that contains a U:A base pair. If the activity of UDG is intact, the uracil base will be removed, creating an abasic/apyrimidinic (AP) site. AP sites will be subsequently cleaved by the downstream BER protein AP endonuclease (APE) to generate a 23-mer band that can be visualized by gel electrophoresis (FIG. 1C). As expected, purified UDG and APE enzymes efficiently removed uracil in the DNA duplex (FIG. 1D, lane 3), serving as a positive control. Nuclear extracts from non-targeted scramble (shSCR)-transfected cells almost completed removed uracil bases (oligo cutting) (FIG. 1D, lane 4). However, extracts from shUDG-transfected cells exhibited markedly reduced activity of removing uracil (minimal cutting) (FIG. 1D, lane 5). These results confirm that UDG is the major contributor to the uracil removal from DNA in cells.

To further study the role of UDG in removing genomic uracil and/or 5-FU, we assessed the levels of uracil and 5-FU in cellular DNA after 5-FdU treatment by the AP site detection assay. Since dUTP and 5-FdUTP pools are not elevated in cancer cells cultured with standard serum in response to 5-FdU, we used medium containing 10% dialyzed serum in this study. We first extracted DNA from cells treated with 5-FdU, exposed the DNA to exogenous UDG to remove residual uracil and 5-FU bases, and then the newly generated AP sites were detected by a novel near infrared (NIR) cyanine-based probe that we previously synthesized and reported. The results showed that the levels of AP sites in shSCR-transfected cells remained low after 5-FdU treatment even at high concentrations (FIG. 1E). In contrast, DNA from shUDG-transfected cells displayed a dramatic increase in the levels of detected AP sites in a 5-FdU dose dependent manner (FIG. 1E), suggesting accumulation of genomic uracil and 5-FU in UDG depleted cells.

AP sites are the common product of removal of uracil and/or 5-FU from DNA. Therefore, the AP site detection assay provides an assessment of the combined cellular levels of uracil and 5-FU but cannot distinguish which one is dominant. Since the pathways of uracil and 5-FU incorporation differ (TS inhibition leads to uracil incorporation, whereas phosphorylation of 5-FdU leads to 5-FU incorporation), the individual levels of uracil and 5-FU may determine which pathway predominantly contribute to UDG removable lesions. To address this issue, we isolated genomic DNA from cells treated with 5-FdU, incubated the DNA with purified UDG, and measured the levels of released uracil and 5-FU by LC-MS/MS. Very low levels of uracil and 5-FU were detected from shSCR-transfected cells even after treatment with high concentrations of 5-FdU (FIG. 1F), indicating efficient removal of these bases from DNA by UDG. On the other hand, a significant increase of both uracil and 5-FU was detected from shUDG-transfected cells after 5-FdU treatment (FIG. 1F). These data demonstrate that 5-FdU treatment leads to roughly equivalent incorporation of both uracil and 5-FU into DNA, indicating that both lesions can contribute to the genotoxicity. These results further suggest that UDG plays a major role in removing these bases and limiting such toxicity.

Loss of UDG Enhances Cytotoxicity of 5-FdU in Cancer Cells

Figure 2A:
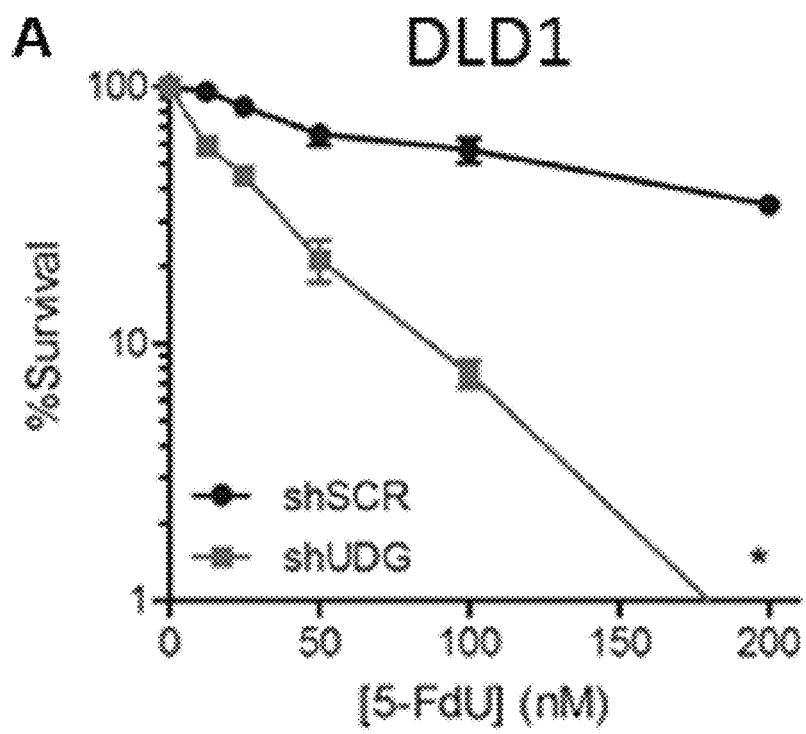
FIGS. 2(A-J) is a graphical illustration that UDG depletion enhances 5-FdU sensitivity in cancer cells Colony survival assays in (A) DLD1 and (B) HEC1A shSCR and shUDG cancer cells treated with increasing doses of 5-FdU, and cell survival was measured as described in Materials and Methods. UDG expression level in HEC1A cells was determined by western blot (inset). Colony survival assays in (C) DLD1 and (D) HEC1A shSCR and shUDG cells treated with increasing doses of pemetrexed. Colony survival assays in DLD1 and HEC1A shSCR and shUDG cells treated with increasing doses of (E, F) cisplatin, (G, H) doxorubicin, or (I, J) temozolomide (TMZ). Viable colonies (>50 cells) stained with methylene blue after 10 d of culture were counted. All survival data represent mean and SEM from at least 3 independent experiments. (*P<0.05).
Figure 2B:
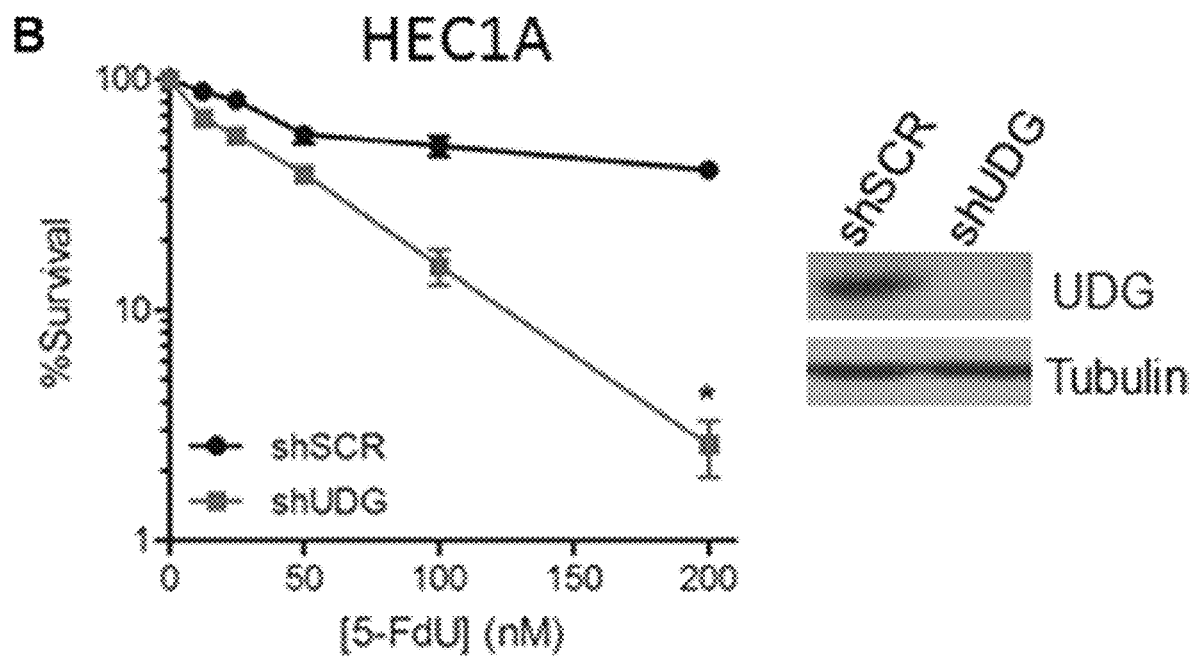
Figure 2C:
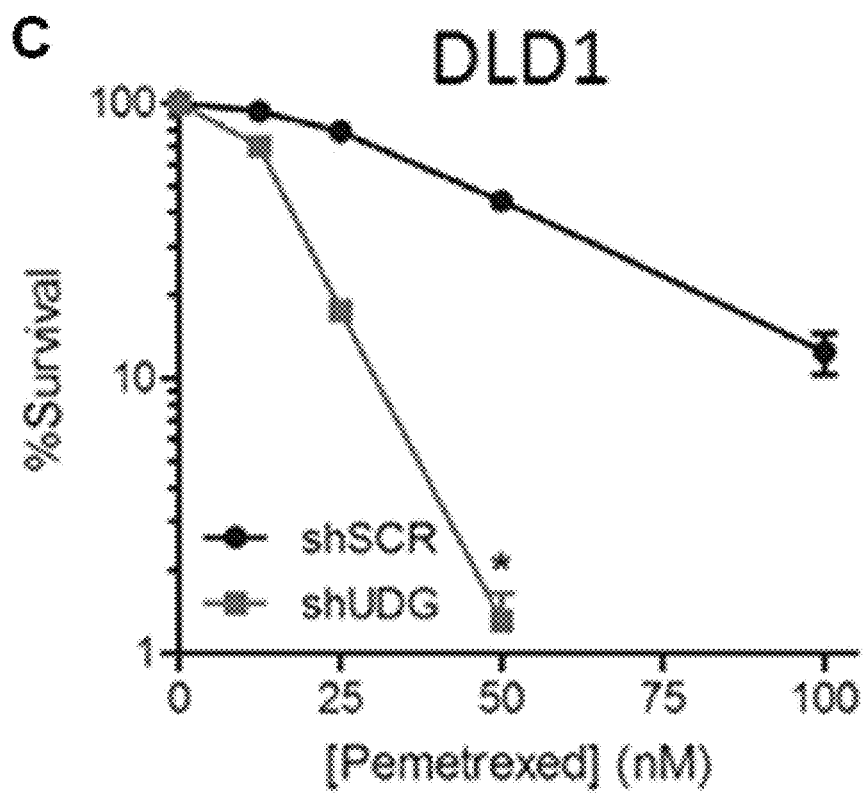
Figure 2D:
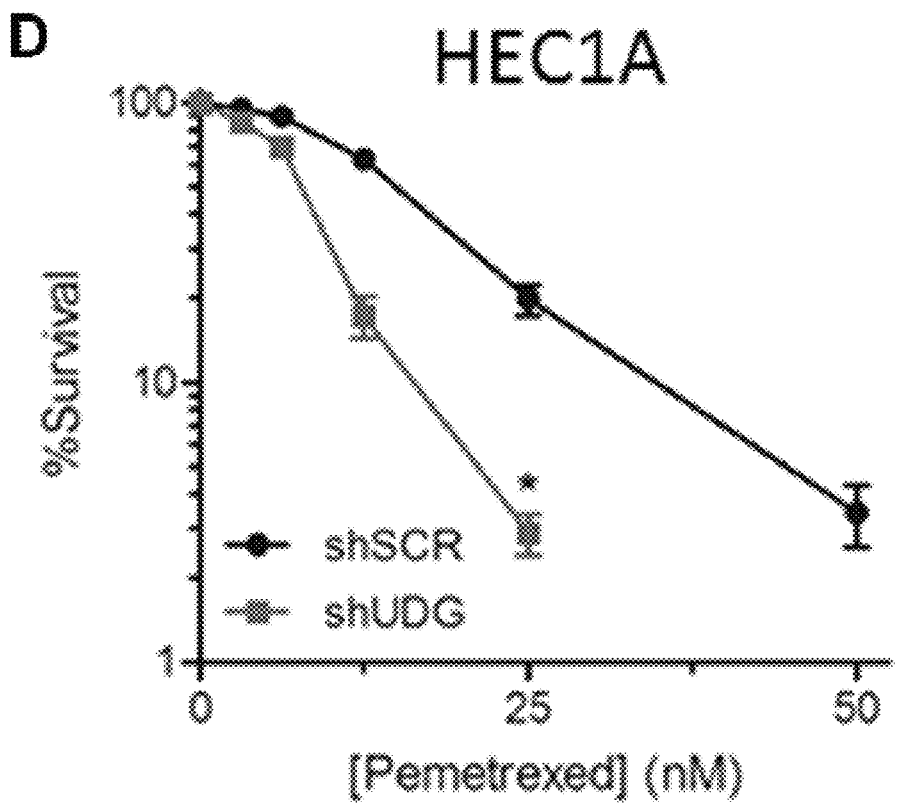
Figure 2E:
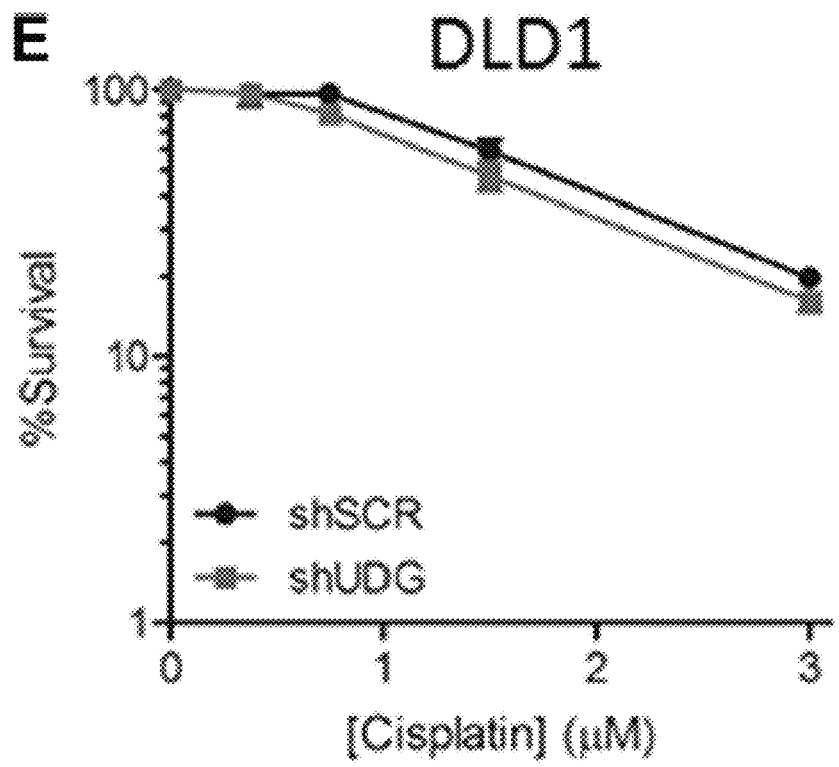
Figure 2F:
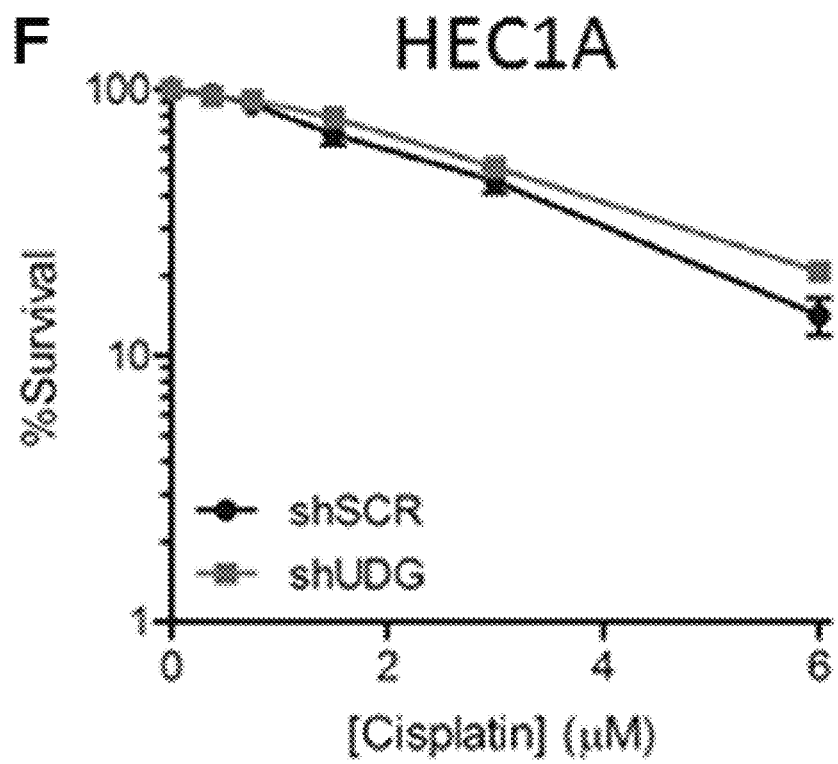
Figure 2G:
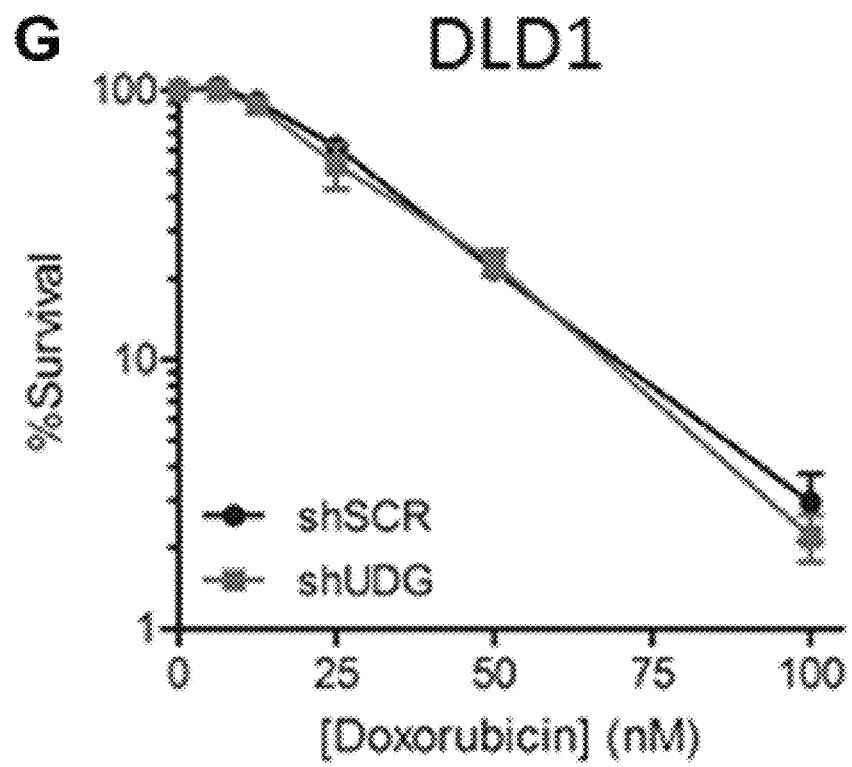
Figure 2H:
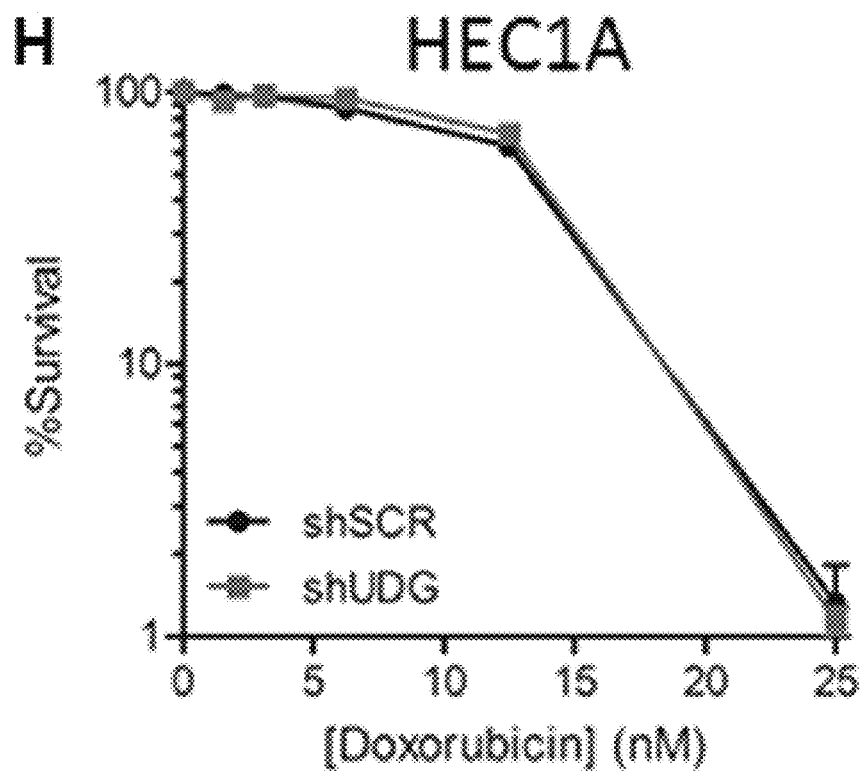
Figure 2I:
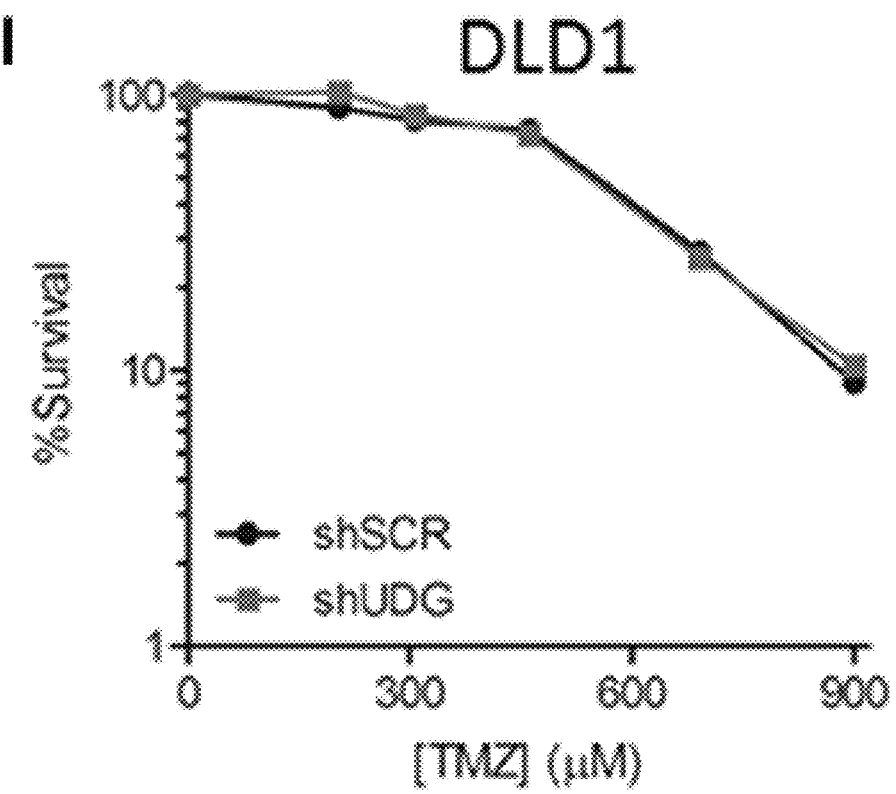
Figure 2J:
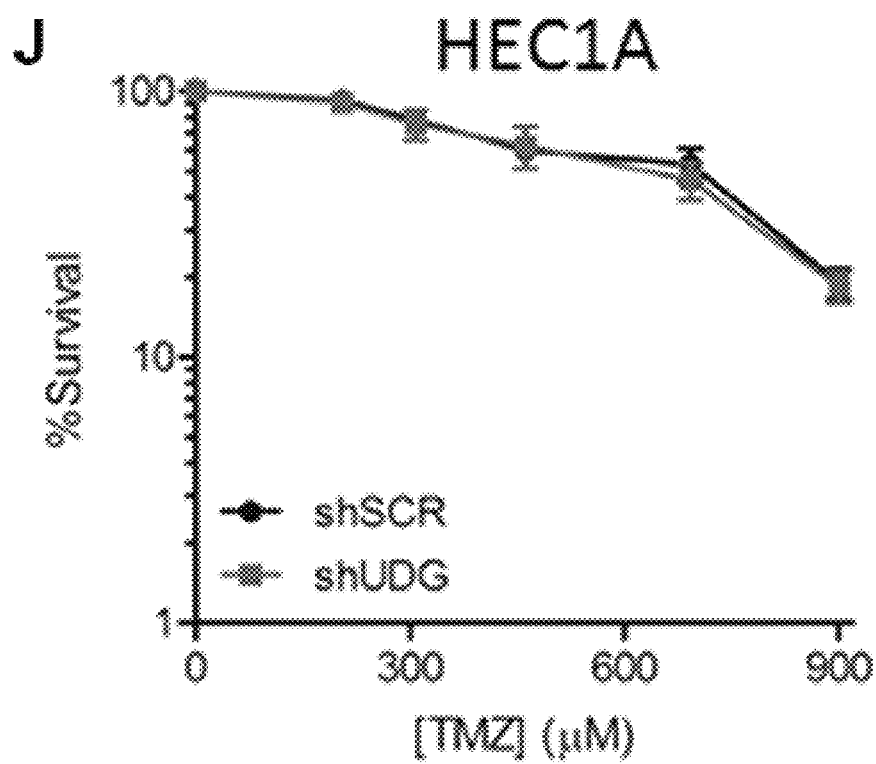

To address the role of UDG in determining the cytotoxicity of 5-FdU, we measured the cell survival of DLD1 colon cancer cells and HEC1A endometrial cancer cells in response to 5-FdU by colony survival assays. The results showed that 5-FdU caused a moderate loss of cell viability in shSCR-transfected cells at high concentrations (FIG. 2A, 2B). Notably, loss of UDG highly sensitized cancer cells to 5-FdU treatment (FIG. 2A, 2B). This sensitization was also observed in UDG depleted DLD1 and HEC1A cancer cells treated with pemetrexed (FIG. 2C, 2D), an antifolate that can also block TS and introduce uracil incorporation into DNA. In contrast, UDG depleted DLD1 and HEC1A cells displayed no further sensitivity to cisplatin (FIG. 2E, 2F), a crosslinking agent, doxorubicin (FIG. 2G, 2H), a DNA intercalating agent, or temozolomide (FIG. 2I, 2J), an alkylating agent, indicating that UDG is not involved in removing crosslinked, intercalated, or methylated nucleotides from DNA. Collectively, these data demonstrate that loss of UDG increases the sensitivity of cancer cells to agents that induce uracil or 5-FU incorporation into DNA, suggesting that UDG plays an important role in determining the cell killing effect of these drugs.

Figure 3A:
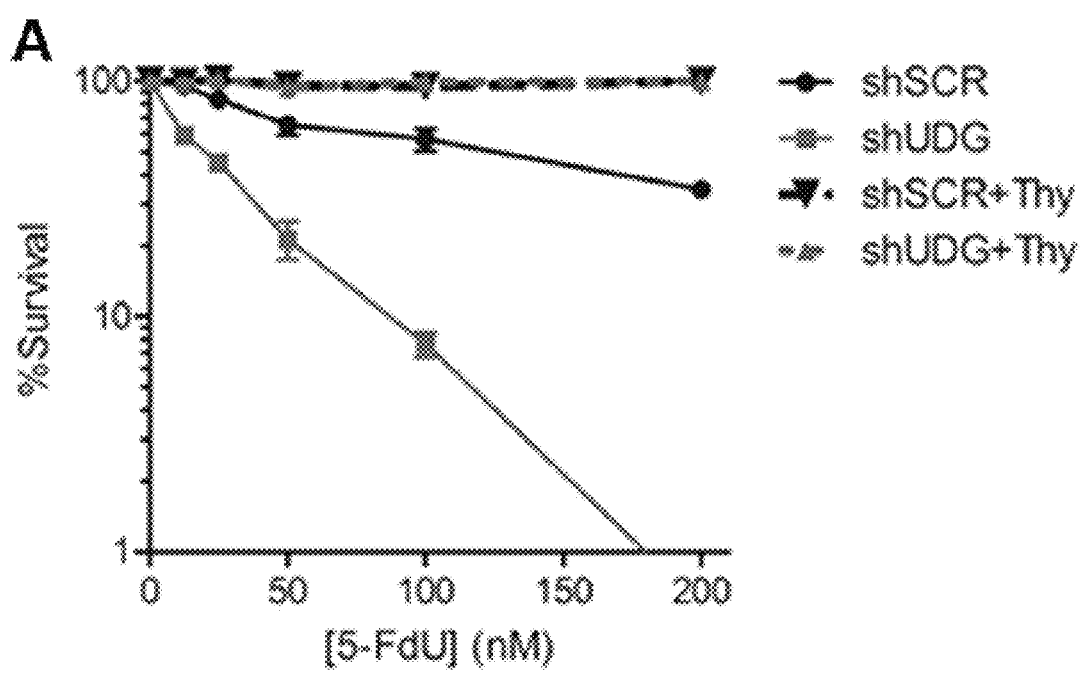
FIGS. 3(A-C) illustrate that thymidine treatment after 5-FdU exposure cannot fully rescue increased cytotoxicity in UDG depleted cells. (A) Colony survival assay in DLD1 shSCR and shUDG cells treated with 0 to 200 nM 5-FdU alone, or supplemented with 20 μM thymidine simultaneously during 5-FdU treatment (+Thy). (B) Colony survival assay in DLD1 shSCR and shUDG cells treated with 0 to 200 nM 5-FdU alone, or supplemented with 20 μM thymidine 24 h after 5-FdU treatment ((+Thy (24 h post)). Data represent mean and error from at least 3 independent experiments. (*P<0.05) (C) DLD1 shSCR and shUDG cells were treated with 100 nM 5-FdU for 24 h, then washed twice with PBS, and incubated in drug-free media supplemented with 20 μM thymidine (Thy) for 6, 12, or 24 h. Genomic DNA was extracted and treated in vitro with purified UDG. AP sites detection was performed by incubation of DNA with a cyanine-based AP site probe. Data represent mean and SD of relative fluorescence intensity normalized to the shSCR DNA without 5-FdU treatment from three independent experiments.
Figure 3B:
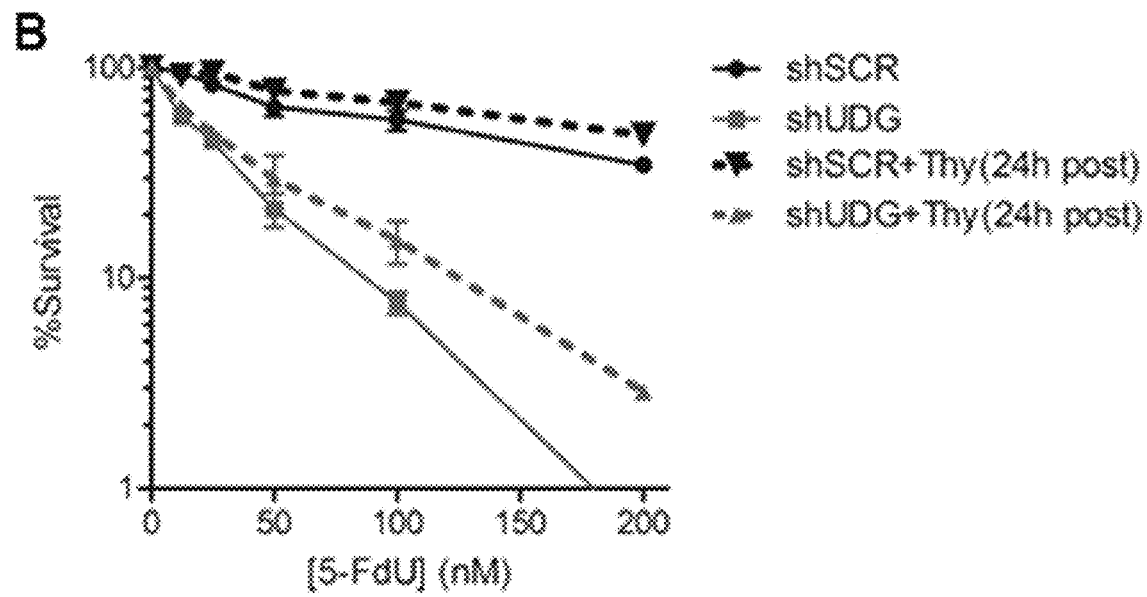
Figure 3C:
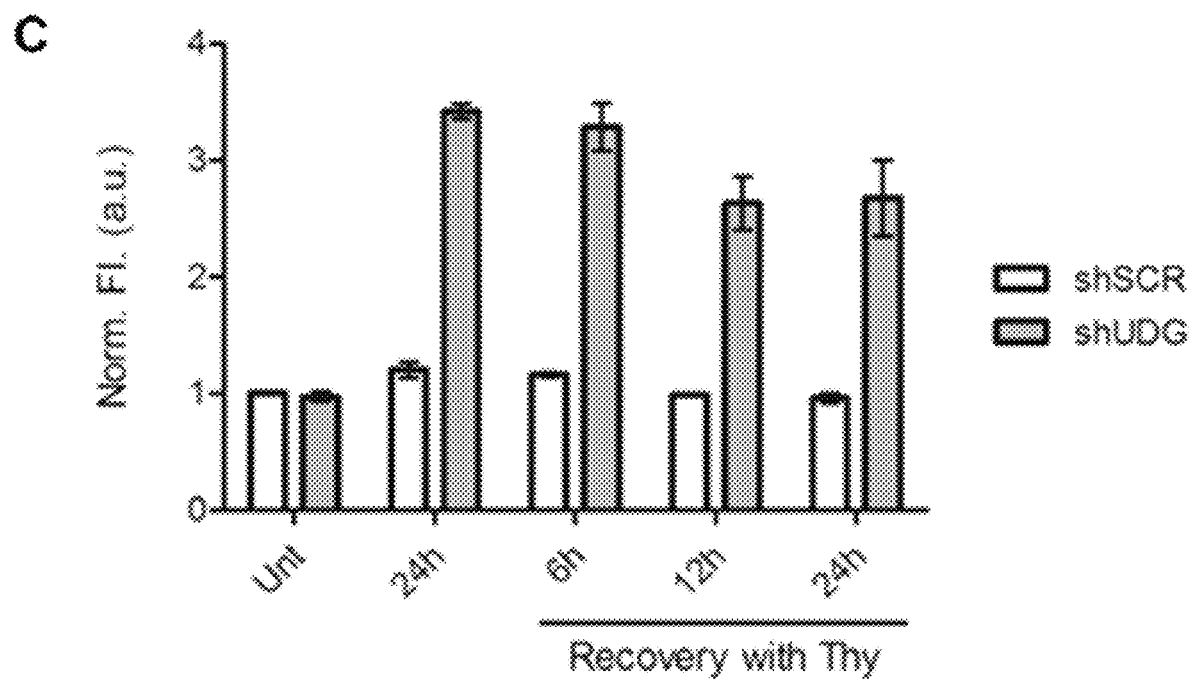
Figure 7:
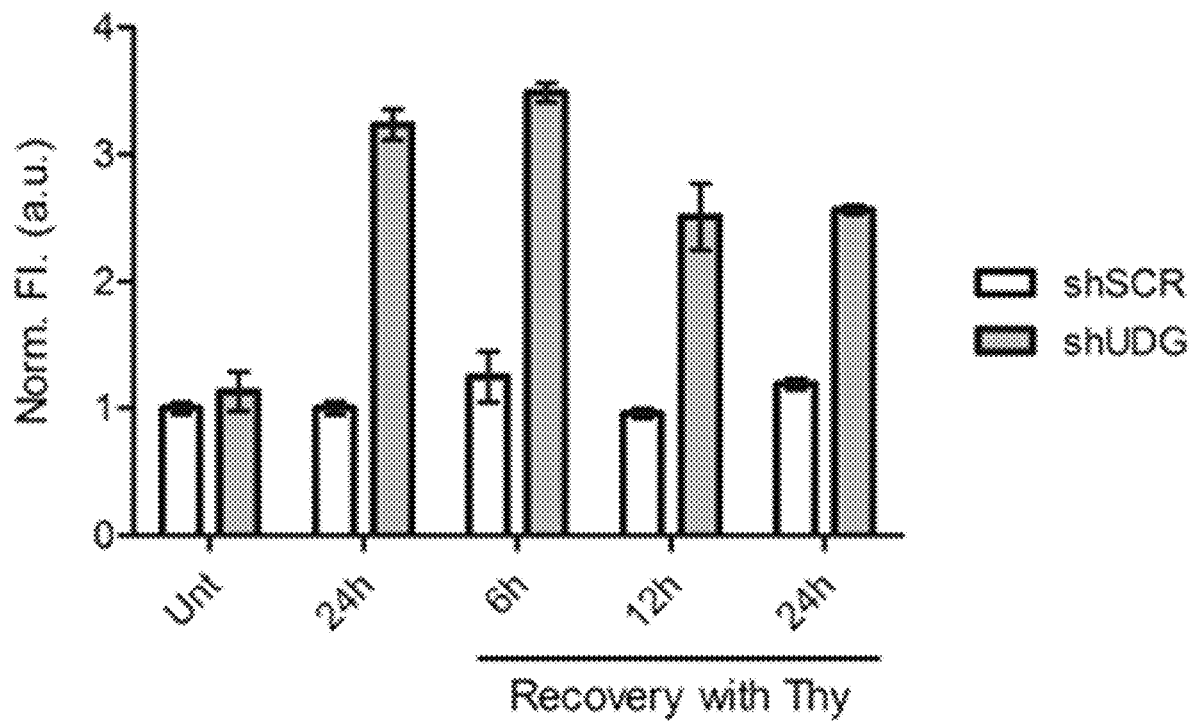
FIG. 7 is a graphical illustration showing that retention of uracil and 5-FU in HEC1A UDG depleted cells during thymidine recovery following 5-FdU exposure. HEC1A shSCR and shUDG cells were treated with 100 nM 5-FdU for 24 h, then washed twice with PBS, and incubated in drug-free media supplemented with 20 μM thymidine (Thy) for 6, 12, or 24 h. Genomic DNA was extracted and treated in vitro with purified UDG. AP sites detection was performed by incubation of DNA with a cyanine-based AP site probe. Data represent mean and SD of relative fluorescence intensity normalized to the shSCR DNA without 5-FdU treatment from three replicates.

Thymidine Treatment after 5-FdU Exposure Cannot Fully Rescue the Enhanced Cytotoxicity in UDG Depleted Cells Due to the Retention of Genomic Uracil and 5-FU Thymidine deficiency has been generally considered as the main cytotoxic mechanism of TS inhibitors. However, our data suggest that it is the incorporation and the lack of removal of genomic uracil and 5-FU lesions that caused the enhanced cytotoxicity of UDG depleted cells to 5-FdU. The replenishment of thymidine should bypass the thymidine deficiency induced by 5-FdU and also reduce the incorporation of either uracil or 5-FU into DNA, a downstream effect of a shortage of thymidine pool. To test this hypothesis, we first examined the effect of simultaneous treatment of thymidine and 5-FdU (shSCR+Thy, shUDG+Thy), which was intended to completely block the thymidineless effect from the beginning. Under these conditions, there was almost no killing in either shSCR-transfected or shUDG-transfected cells (FIG. 3A). However, when thymidine was replenished 24 h after 5-FdU treatment (shSCR+Thy (24 h post), shUDG+Thy (24 h post)), it barely inhibited cell death of UDG depleted cells caused by 5-FdU (FIG. 3B), indicating that the enhanced killing effect by UDG depletion is due to the incorporation of uracil and 5-FU into DNA instead of the lack of thymidine. To further prove that uracil and 5-FU lesions are indeed retained in DLD1 UDG depleted cells even during recovery in the presence of thymidine, we performed the AP site detection assay in cells treated with thymidine after 24 h of 5-FdU exposure. The results showed that UDG depleted cells accumulated about three times higher the level of uracil and 5-FU than shSCR-transfected cells following 24 h of 5-FdU treatment (FIG. 3C). After 24 h of 5-FdU exposure, cells were washed and placed in drug-free medium supplemented with thymidine. Notably, we observed that the uracil and 5-FU levels in UDG depleted cells remained persistent during 6, 12, and 24 h of thymidine recovery (FIG. 3C). Furthermore, the retention of uracil and 5-FU during thymidine recovery following 5-FdU treatment was also detected in HEC1A UDG depleted cells (FIG. 7). Taken together, these data suggest that the enhanced cytotoxicity in UDG depleted cells is attributed to the retention of uracil and 5-FU in DNA.

UDG Depletion Leads to Cell Cycle Arrest at Late G1 and Early S Phase by 5-FdU

Figure 4A:
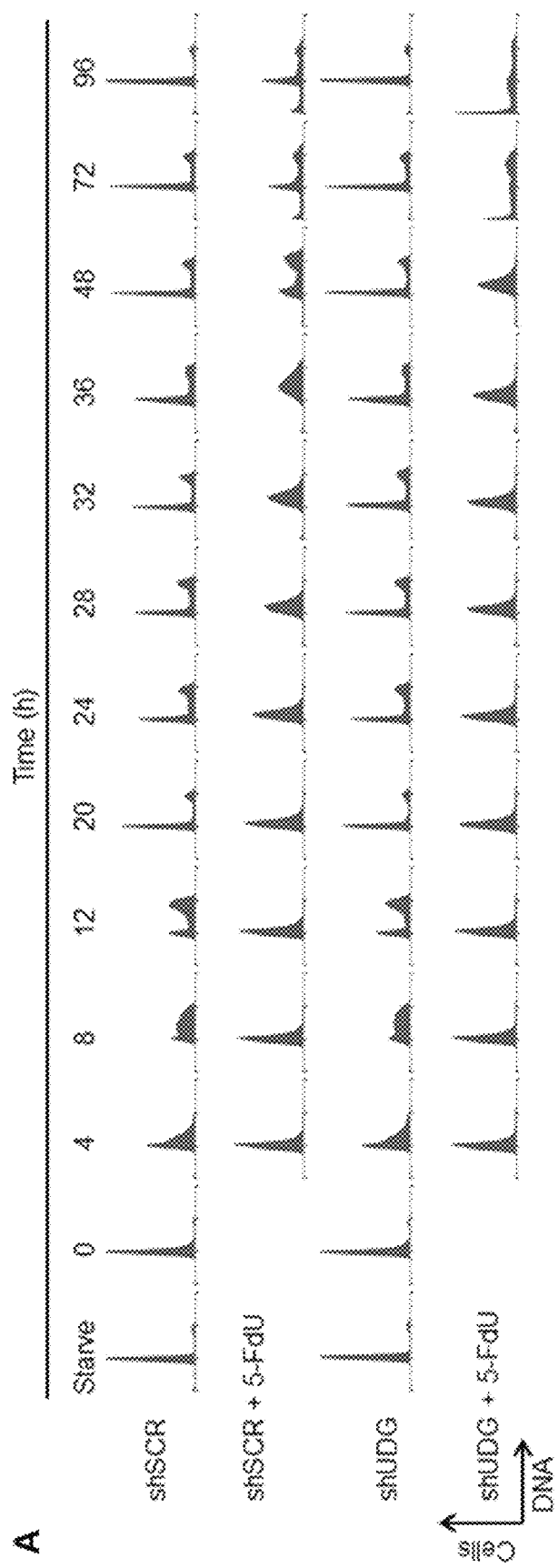
FIGS. 4(A-E) illustrate that loss of UDG induces cell cycle arrest at late G1 and early S phase by 5-FdU exposure. (A) DLD1 shSCR and shUDG cells were synchronized at G0/G1 phase by serum starvation for two days indicated as Starve. Cell cycle and growth were resumed by releasing cells into medium containing 10% dialyzed FBS for 16 h. Cells were then exposed to 100 nM 5-FdU for indicated times (0-96 h). Cell cycle of untreated and treated cells was analyzed by PI mediated flow cytometry. (B) Quantification of each phases of the cell cycle for shSCR and shUDG cells from A. (C) Unsynchronized DLD1 shSCR and shUDG cells were untreated (Unt) or treated with 100 nM 5-FdU for 24 h and pulsed with BrdU for 45 minutes. Cells were collected, fixed and stained with anti-BrdU antibody and PI dye. Cell cycle profiles were analyzed by flow cytometry. eS=early S-phase; mS=mid-S-phase; lS=late S/G2-phase. Quantification of each phases of the cell cycle for DLD1 (D) shSCR and (E) shUDG cells from C. Data for a representative experiment that has been performed three times is shown.
Figure 4B:
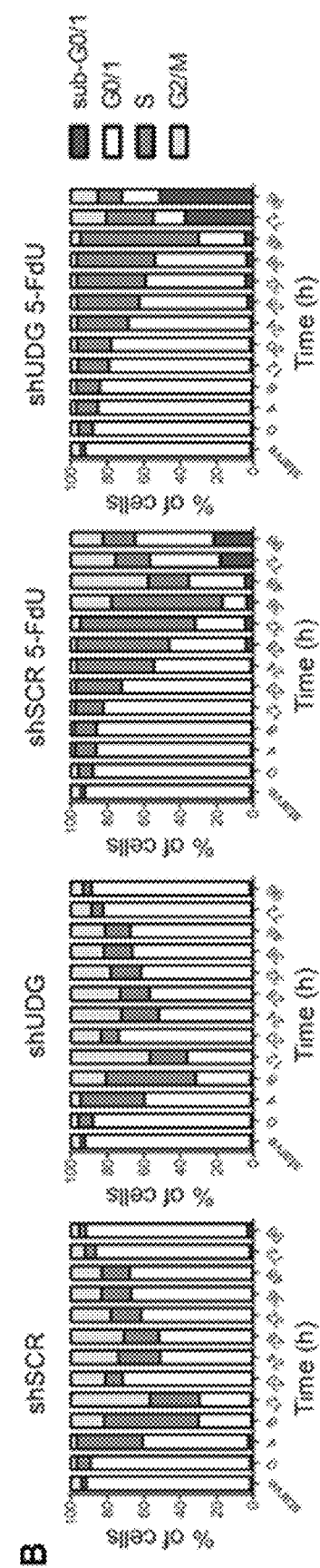

Studies have shown that TS inhibition leads to S phase arrest by blocking DNA replication as a result of dTTP deficiency. To elucidate the molecular mechanisms by which UDG regulates cellular sensitivity to 5-FdU, we monitored cell cycle progression by propidium iodide (PI) staining. DLD1 cells were synchronized at G0/G1 phase through serum starvation, resumed growth by placing in medium containing 10% dialyzed FBS for 16 h which did not result in progression through cell cycle, and then exposed to 5-FdU for an additional 0 to 96 h. In the absence of 5-FdU, both shSCR-transfected and shUDG-transfected cells progressed similarly through S and G2/M phases by 8 and 12 h, respectively (FIG. 4A, 4B), indicating that UDG depletion did not affect normal cell cycle progression. As expected, 5-FdU slowed the progression of shSCR-transfected cells through S phase by 36 h, and cells entered the next cell cycle by 48 h with a relatively small portion of cells at sub-G1 phase (FIG. 4A, 4B). However, 5-FdU treatment triggered a strong cell cycle arrest of UDG depleted cells at late G1 and early S phase which lasted for 48 h and later displayed a chaotic cell cycle distribution pattern at 72 h and 96 h with substantially increased sub-G1 population (FIG. 4A, 4B).

Figure 4C:
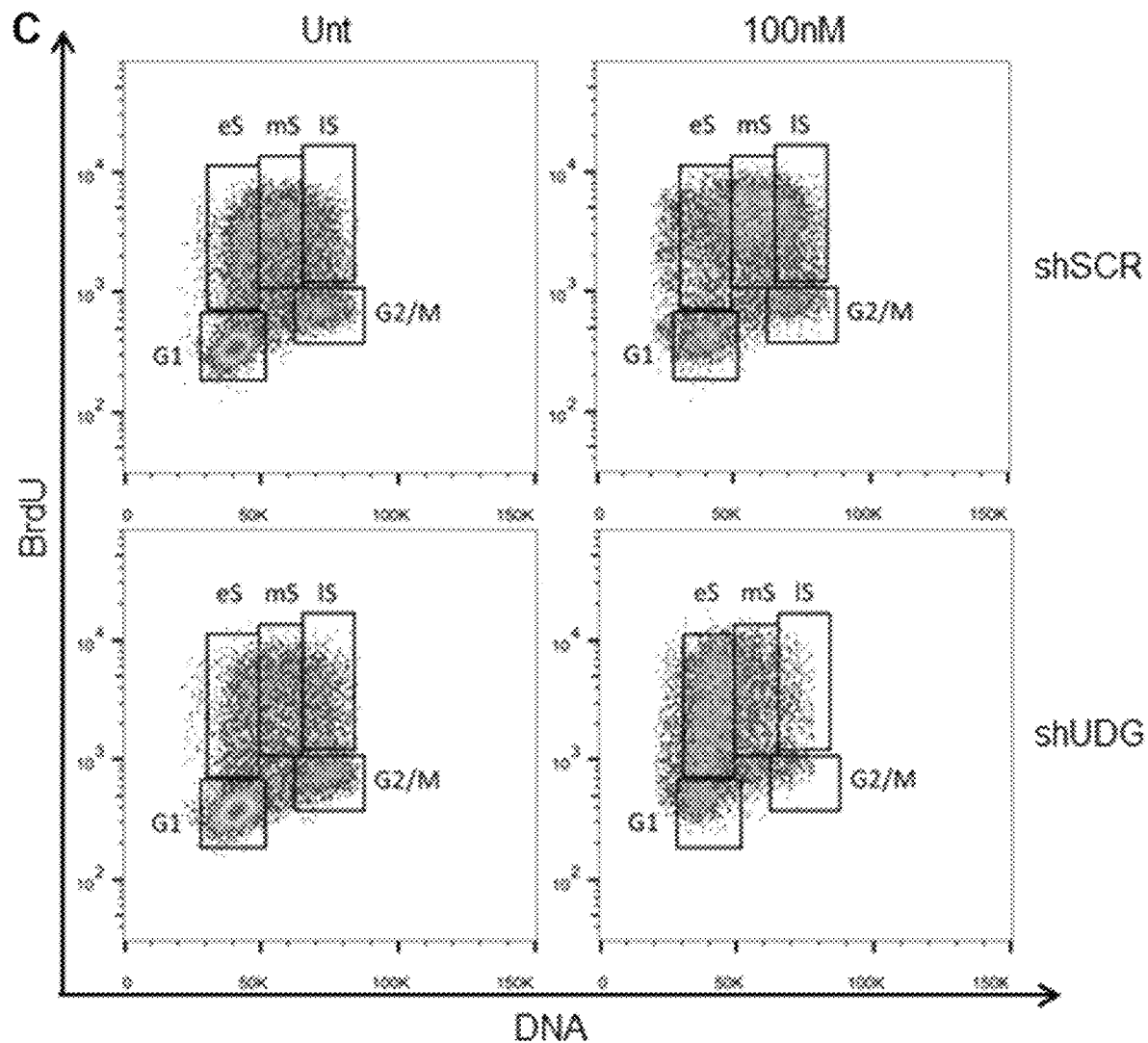
Figure 4D:
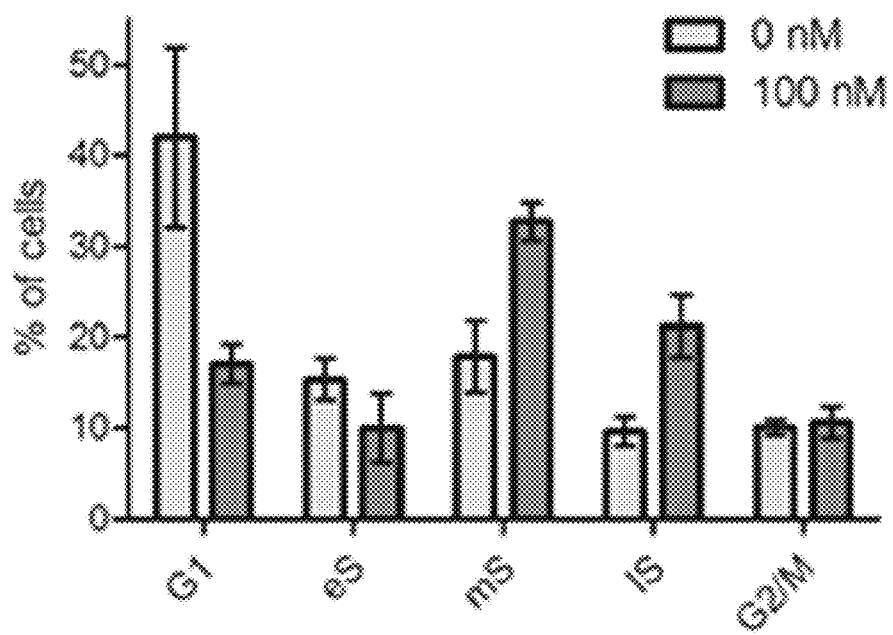
Figure 4E:
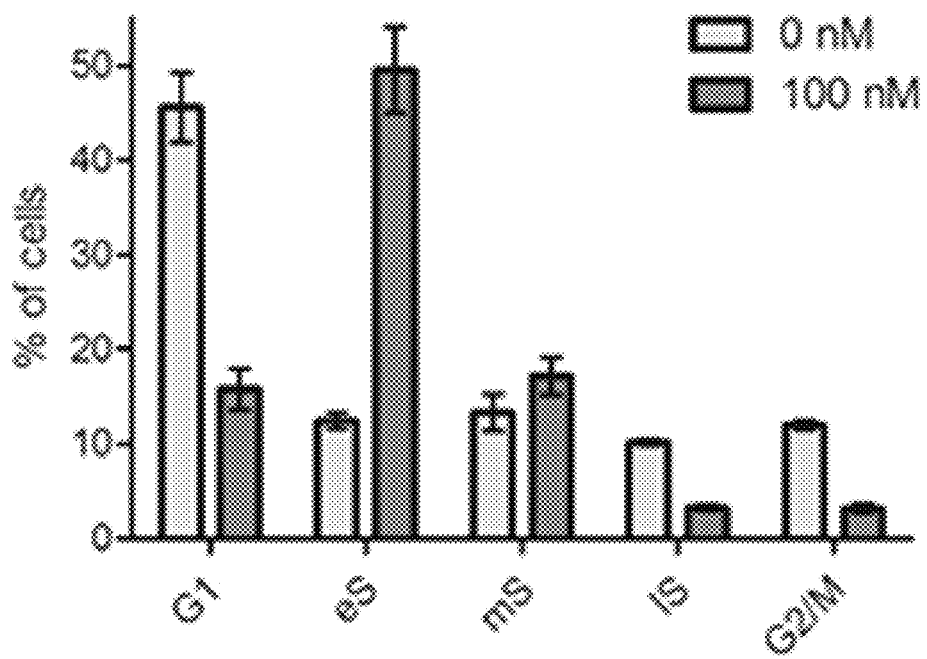
Figure 8A:
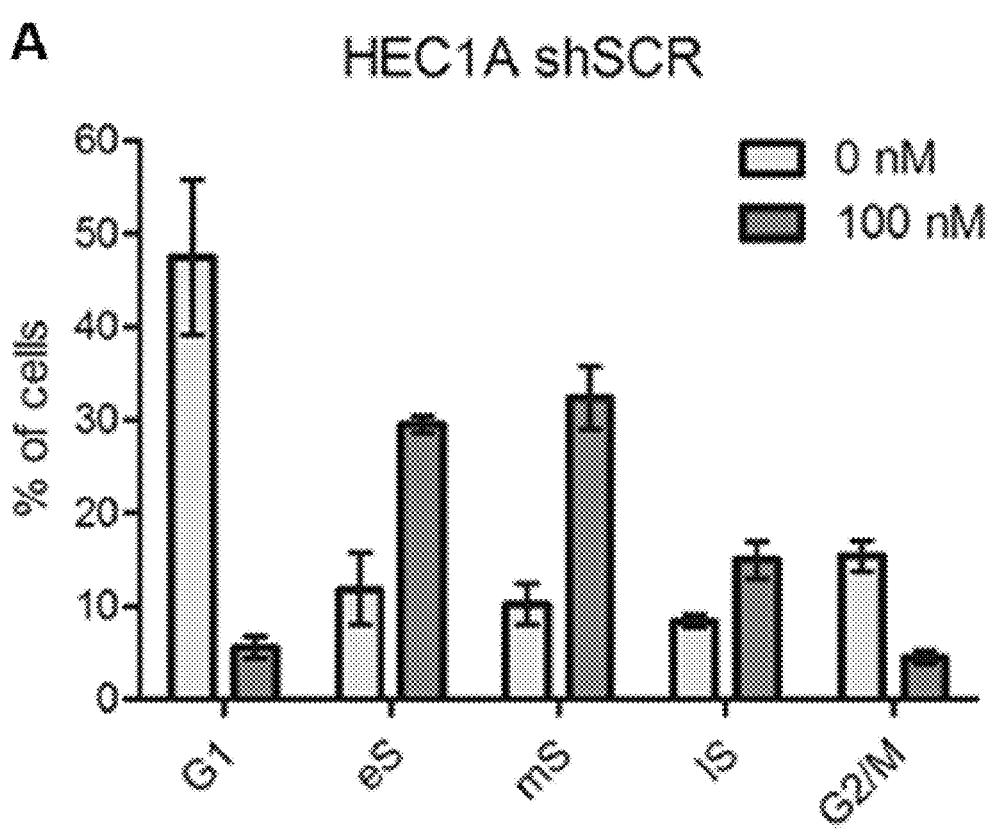
FIGS. 8(A-B) is a graphical illustration showing that loss of UDG induces HEC1A cell cycle arrest at late G1 and early S phase following 5-FdU exposure. Quantification of each phases of the cell cycle for unsynchronized HEC1A (A) shSCR and (B) shUDG cells untreated (Unt) or treated with 100 nM 5-FdU for 24 h. After treatment, cells were pulsed with BrdU for 45 minutes, fixed, and stained with anti-BrdU antibody and PI dye. Cell cycle profiles were analyzed by flow cytometry. eS=early S-phase; mS=mid-S-phase; 1S=late S/G2-phase. Data represent mean and SD from 3 independent experiments.
Figure 8B:
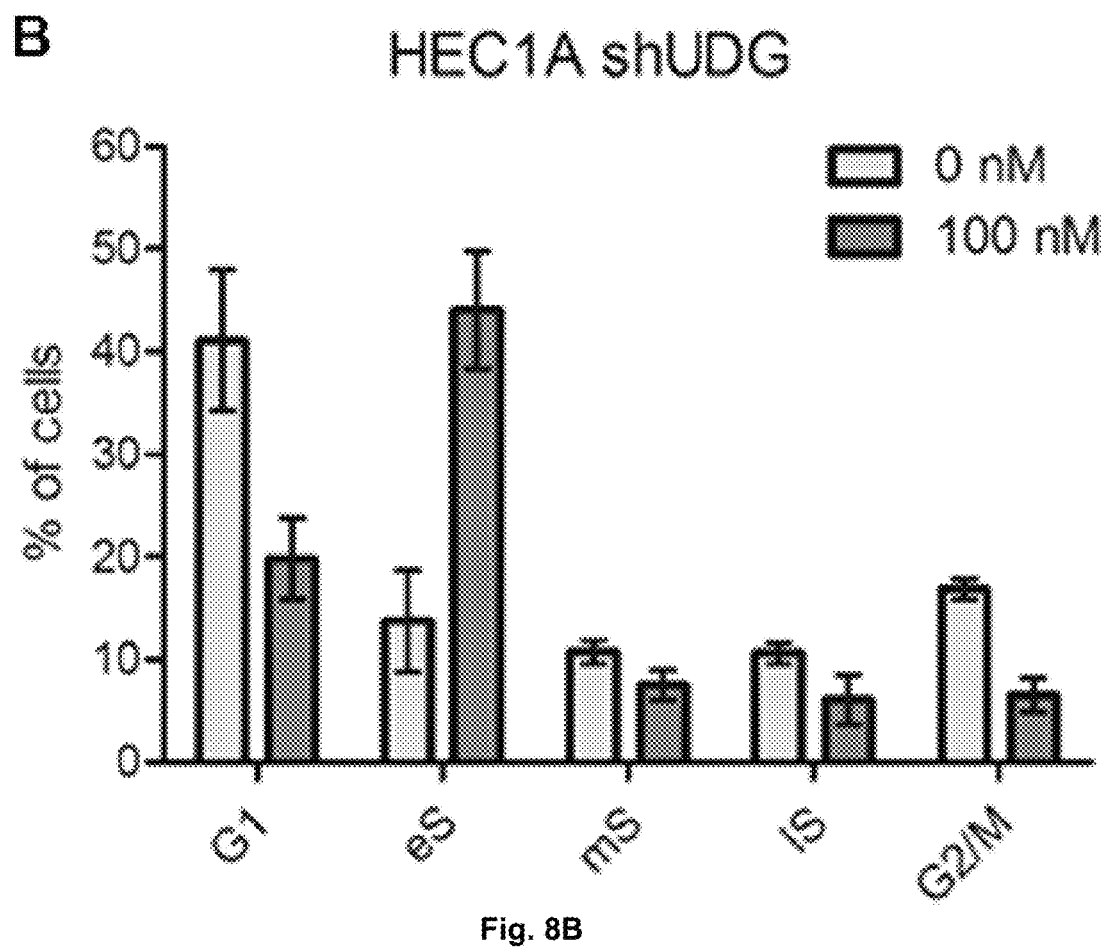

To confirm the cell cycle arrest results, we monitored the S phase population of unsynchronized cells by BrdU and PI co-staining in DLD1 cancer cells. Consistently, we observed S phase arrest especially at middle and late S phase in shSCR-transfected cells as a result of TS inhibition after 24 h of 5-FdU exposure (FIG. 4C, 4D). In contrast, DLD1 shUDG-transfected cells were arrested at late G1 and early S phase following 24 h of 5-FdU exposure (FIG. 4C, 4E). In addition, the G1/S phase arrest was also confirmed in HEC1A UDG depleted cells (FIG. 8). Together, these findings implicate that loss of UDG affects cell cycle progression at early S phase in response to continuous 5-FdU exposure, likely due to the accumulation of uracil and 5-FU in genomic DNA that blocks DNA replication.

Loss of UDG Inhibits DNA Replication Progression in Response to 5-FdU Treatment

Figure 5A:
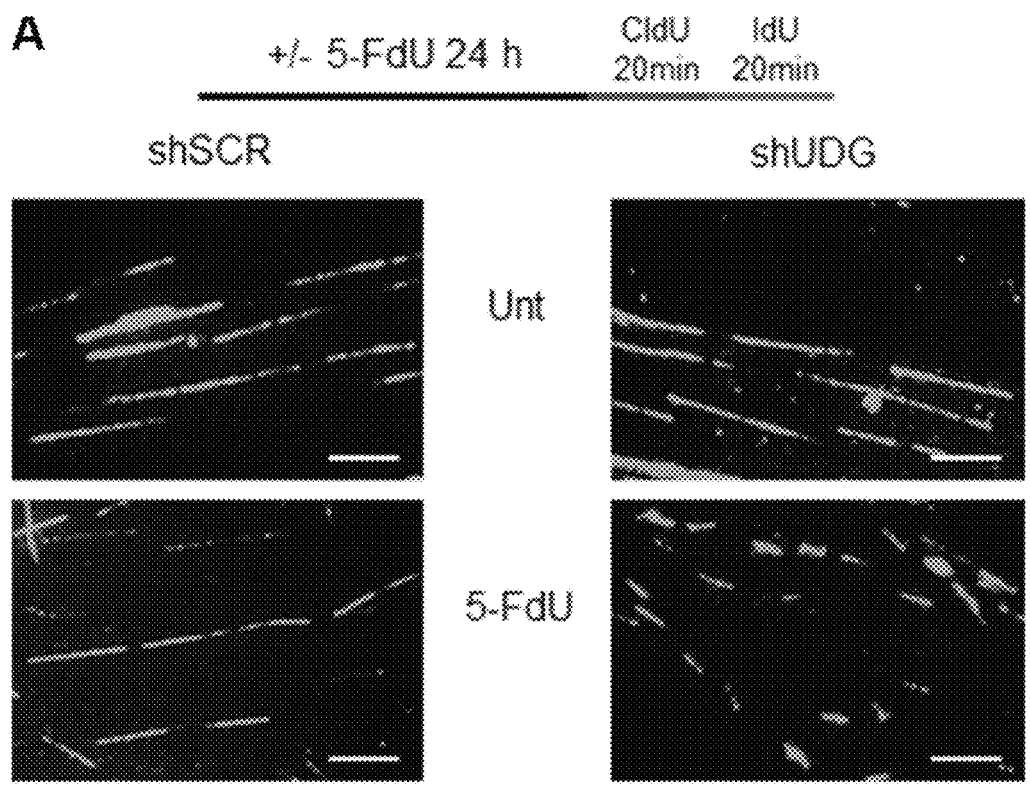
FIGS. 5(A-B) illustrate that UDG depletion inhibits replication fork progression following 5-FdU treatment. (A) DLD1 shSCR and shUDG cells were untreated (Unt) or treated with 100 nM 5-FdU for 24 h, washed, pulsed with CldU and IdU sequentially for 20 minutes. Cells were lysed and DNA fragments were spread on the slide. The fixed samples were stained with anti-CldU and anti-IdU antibodies. DNA fibers were visualized on fluorescence microscope (100× oil lens). (Scale bar: 5 μm) (B) Quantification of the DNA fiber length. The statistical analysis of DNA fiber length across the populations analyzed (n>200 fibers per population) is shown as a scatter plot with medians and the interquartile ranges. To monitor the replication progression speed, we only counted the IdU track as it represents ongoing replication length.
Figure 5B:
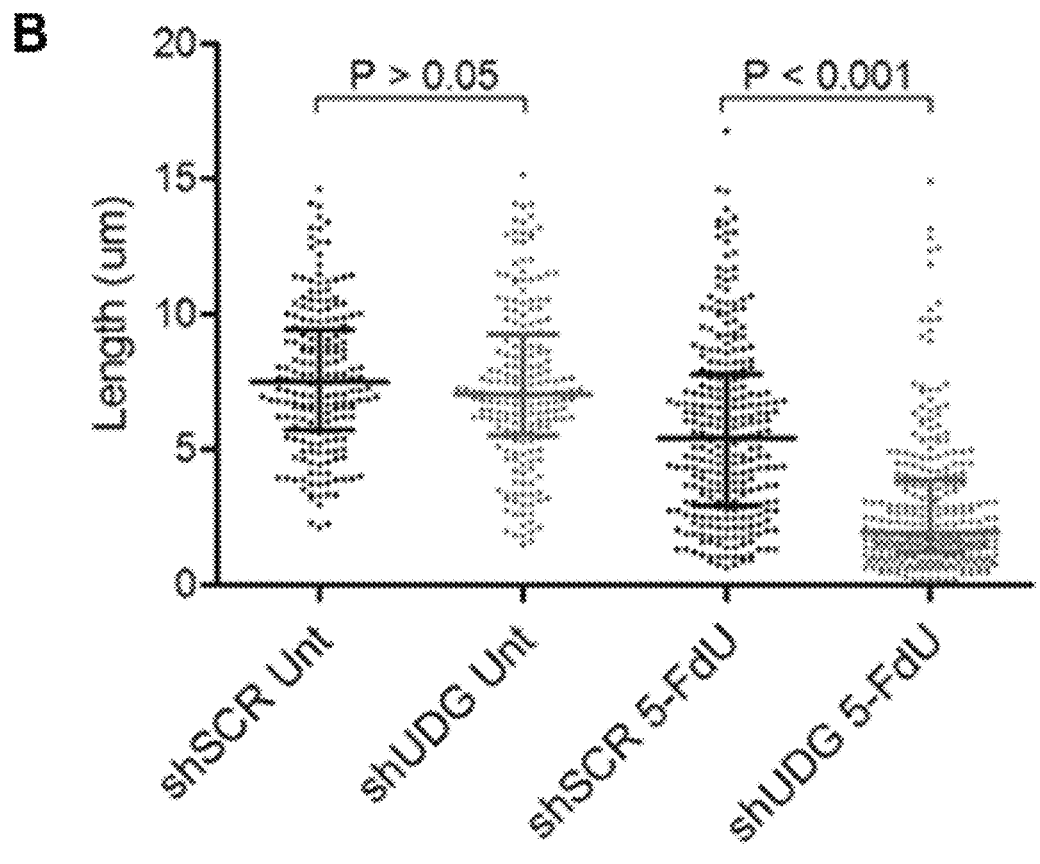

To directly investigate the mechanism by which 5-FdU arrests UDG depleted cells at G1/S phase, we monitored replication fork progression by DNA fiber analysis. Following 24 h 5-FdU treatment, DLD1 cells were sequentially pulsed with halogenated nucleotides chlorodeoxyuridine (CldU) and iododeoxyuridine (IdU) for 20 minutes (FIG. 5A). DNA fibers stained with both CldU (red, not shown) and IdU (green) were included in the following analysis. To assess the impact on DNA replication progression, we measured the track length of IdU as it represents the ongoing replication fork. In the absence of 5-FdU, the mean fiber length for both shSCR- and shUDG-transfected cells was around 7.5 μm (FIG. 5B). Following 24 h 5-FdU exposure, the mean fiber length of nascent DNA strands reduced by 23% to 5.7 μm in shSCR-transfected cells, consistent with the temporal S phase arrest results (FIG. 4). Strikingly, UDG depleted cells displayed significantly shorter fiber track with the mean value at 2.8 μm, representing a 63% reduction (FIG. 5B), consistent with the prolonged G1/S arrest. These results illustrate that loss of UDG inhibits DNA replication in response to 5-FdU by severely reducing the elongation of nascent DNA strands.

Figure 6A:
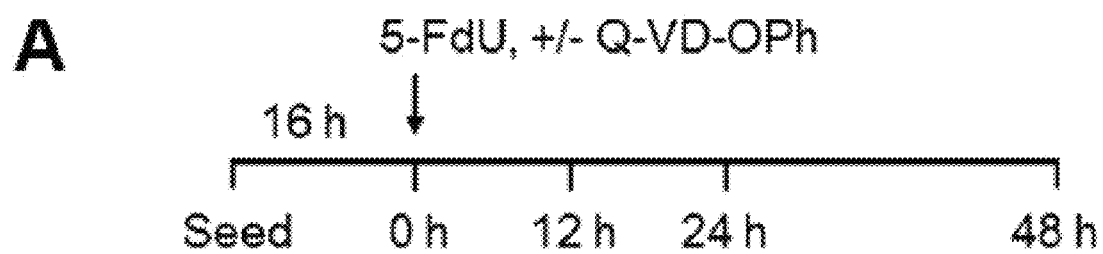
FIGS. 6(A-E) illustrate that DNA damage accumulates in UDG depleted cells in a caspase independent manner. (A) Schematic diagram of the treatment of DLD1 cells with 5-FdU in the presence or absence (+/−) of 10 μM caspase inhibitor Q-VD-OPh at indicated time points. (B) DLD1 shSCR and shUDG cells were treated with 50 nM 5-FdU for 12, 24, and 48 h with (+) and without (−) 10 μM Q-VD-OPh. Cells were fixed and stained with anti-γH2AX antibodies. γH2AX foci was visualized on a fluorescence microscope. (C) Quantification of the number of γH2AX foci per cell for 0, 12, 24, and 48 h of 5-FdU treatment in the presence (+) or absence (−) of Q-VD-OPh. The statistical analysis of γH2AX foci per cell across the populations analyzed (n>100 cells per population) is shown as a scatter plot with medians and the interquartile ranges. (D) Quantification of the percentage of cells with >10 γH2AX foci per cell for 0, 12, 24, and 48 h of 5-FdU treatment. Statistical analysis was performed as in C. (E) In parallel samples from B, the expression level of cleaved PARP was analyzed for cells untreated (Unt) or treated with 50 nM 5-FdU for 12, 24, and 48 h in the presence (+) or absence (−) of 10 μM caspase inhibitor Q-VD-OPh.
Figure 6B:
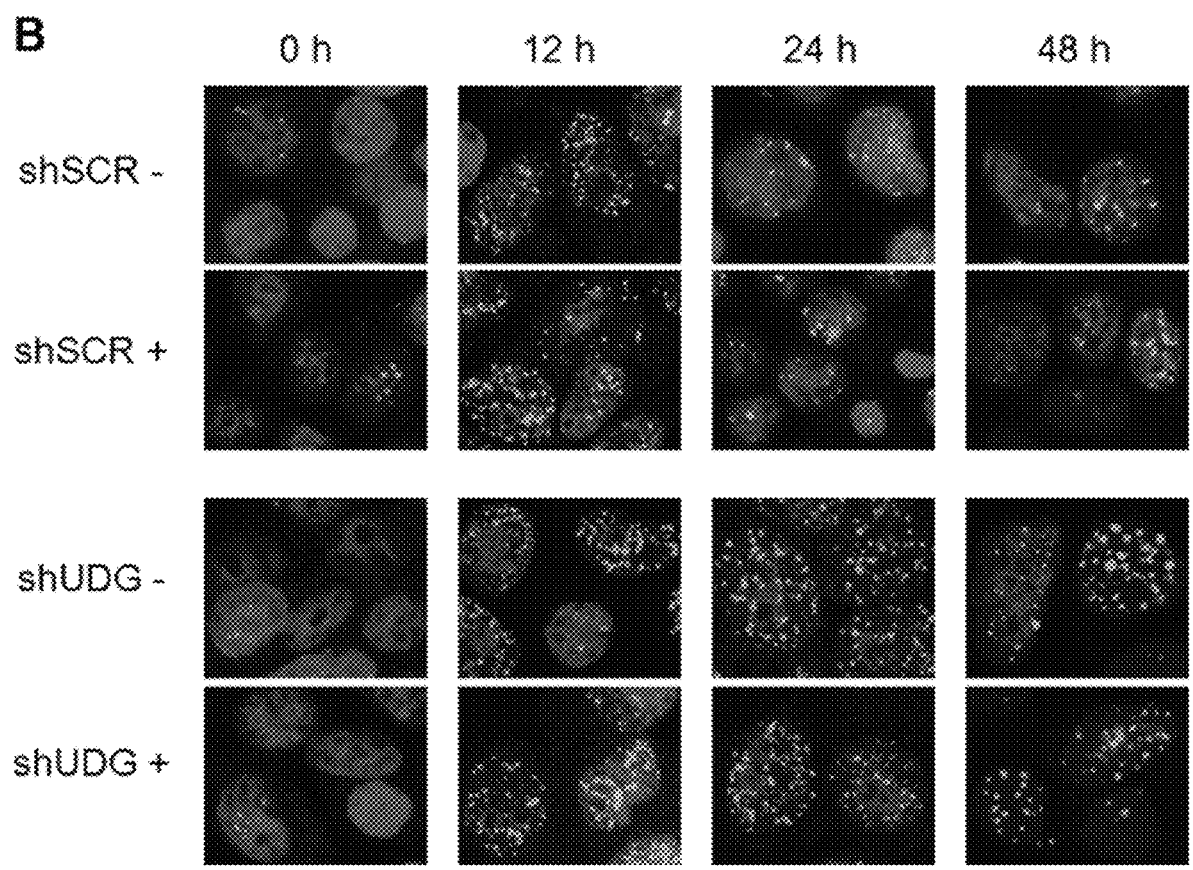
Figure 6C:
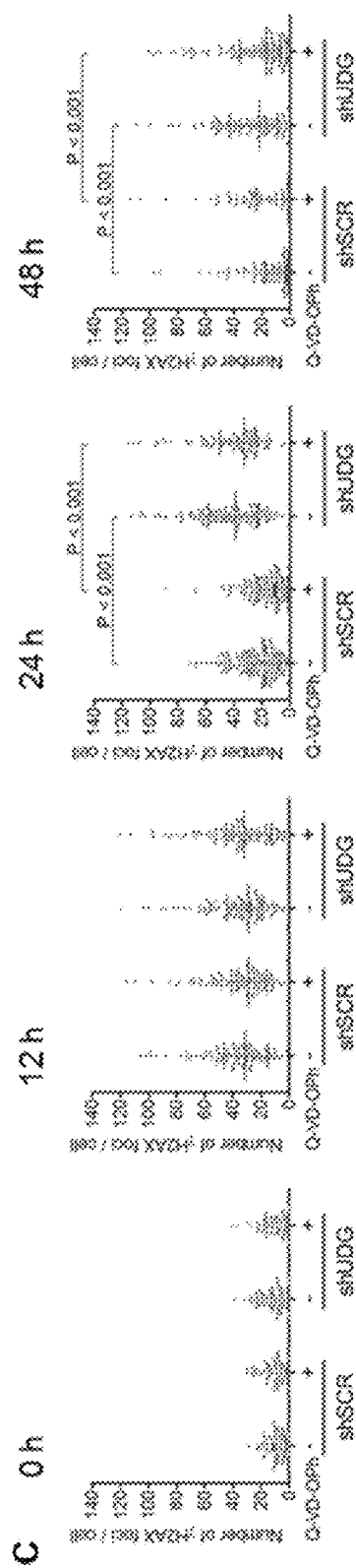
Figure 6D:
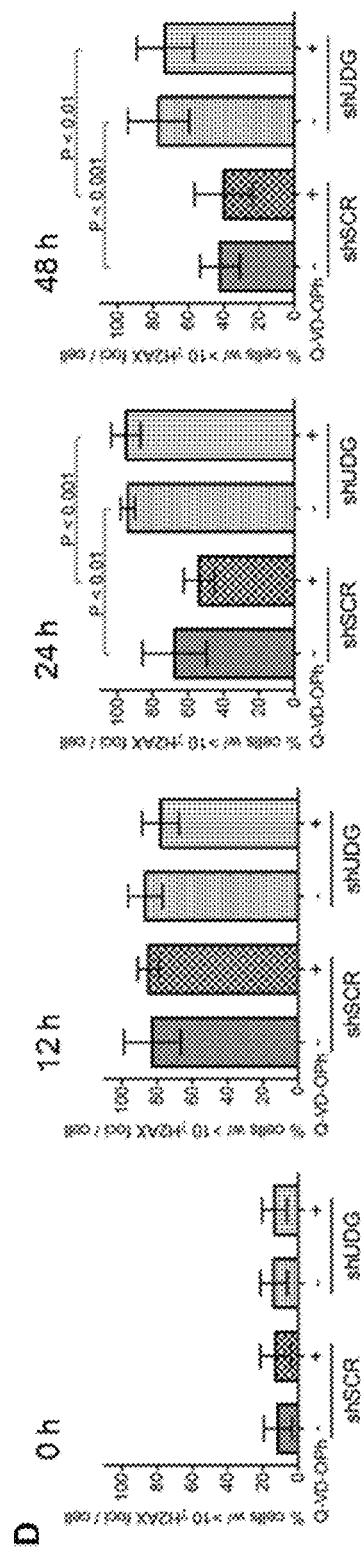

DNA Damage Persists in UDG Depleted Cells and is not Due to Apoptosis by 5-FdU Treatment The dramatic increase in sub-G1 population in UDG depleted cells by 5-FdU indicates that these cells are undergoing apoptotic cell death. However, what caused the cell death remains unclear. Prolonged replication fork stalling due to dNTP imbalance can lead to fork collapse and the generation of DNA double strand breaks (DSBs), a highly mutagenic and toxic form of DNA damage. To understand if UDG depleted cells accumulate DNA damage by 5-FdU treatment, we performed immunostaining to assess the generation of DSBs using specific antibodies to detect foci formation of the phosphorylated histone variant H2AX (γH2AX), a marker of DSBs (FIG. 6A). In DLD1 shSCR-transfected cells, 5-FdU caused the maximal increase in the level of DSBs and the percentage of cells with over 10 foci by 12 h of treatment, which then gradually declined despite the presence of 5-FdU (FIG. 6B-6D), indicating cells expressing UDG are able to repair DNA damage even in the presence of 5-FdU. On the other hand, both the foci number and the percentage of cells with over 10 foci remained persistent during 5-FdU exposure in DLD1 UDG depleted cells (FIG. 6B-6D), suggesting sustained DNA damage in the absence of UDG. Consistently, in HEC1A shSCR-transfected cells, the maximal level of DSBs and the percentage of cells with over 10 foci were detected at 48 h of 5-FdU treatment, which then reduced at 72 h and 96 h of treatment (FIG. 9A-9D). However, in HEC1A UDG depleted cells, the foci number and the percentage of cells with over 10 foci remained high during 5-FdU exposure (FIG. 9A-9D).

Figure 6E:
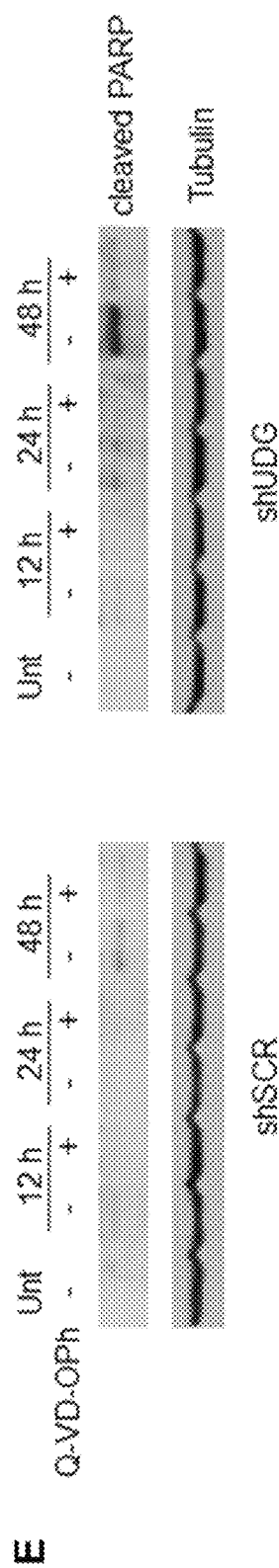
Figure 9A:
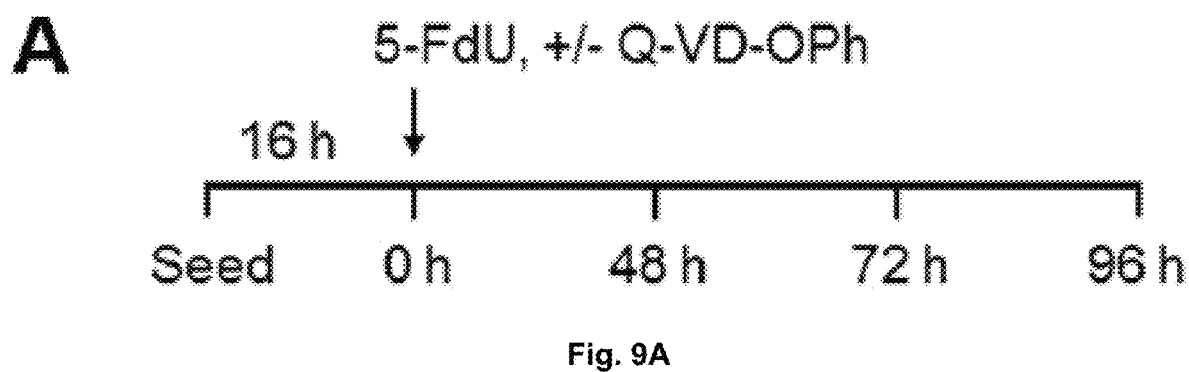
FIG. 9(A-E) illustrate that DNA damage accumulates in HEC1A UDG depleted cells in a caspase independent manner. (A) Schematic diagram of the treatment of HEC1A cells with 5-FdU in the presence or absence (+/−) of 10 μM caspase inhibitor Q-VD-OPh at indicated time points. (B) HEC1A shSCR and shUDG cells were treated with 50 nM 5-FdU for 48, 72, and 96 h with (+) and without (−) 10 μM Q-VD-OPh. Cells were fixed and stained with anti-γH2AX antibodies. γH2AX foci was visualized on a fluorescence microscope. (C) Quantification of the number of γH2AX foci per cell for 0, 48, 72, and 96 h of 5-FdU treatment in the presence (+) or absence (−) of Q-VD-OPh. The statistical analysis of γH2AX foci per cell across the populations analyzed (n>100 cells per population) is shown as a scatter plot with medians and the interquartile ranges. (D) Quantification of the percentage of cells with >10 γH2AX foci per cell for 0, 48, 72, and 96 h of 5-FdU treatment. Statistical analysis was performed as in C. (E) In parallel samples from B, the expression level of cleaved PARP was analyzed for cells untreated (Unt) or treated with 50 nM 5-FdU for 48, 72, and 96 h in the presence (+) or absence (−) of 10 μM caspase inhibitor Q-VD-OPh.
Figure 9B:
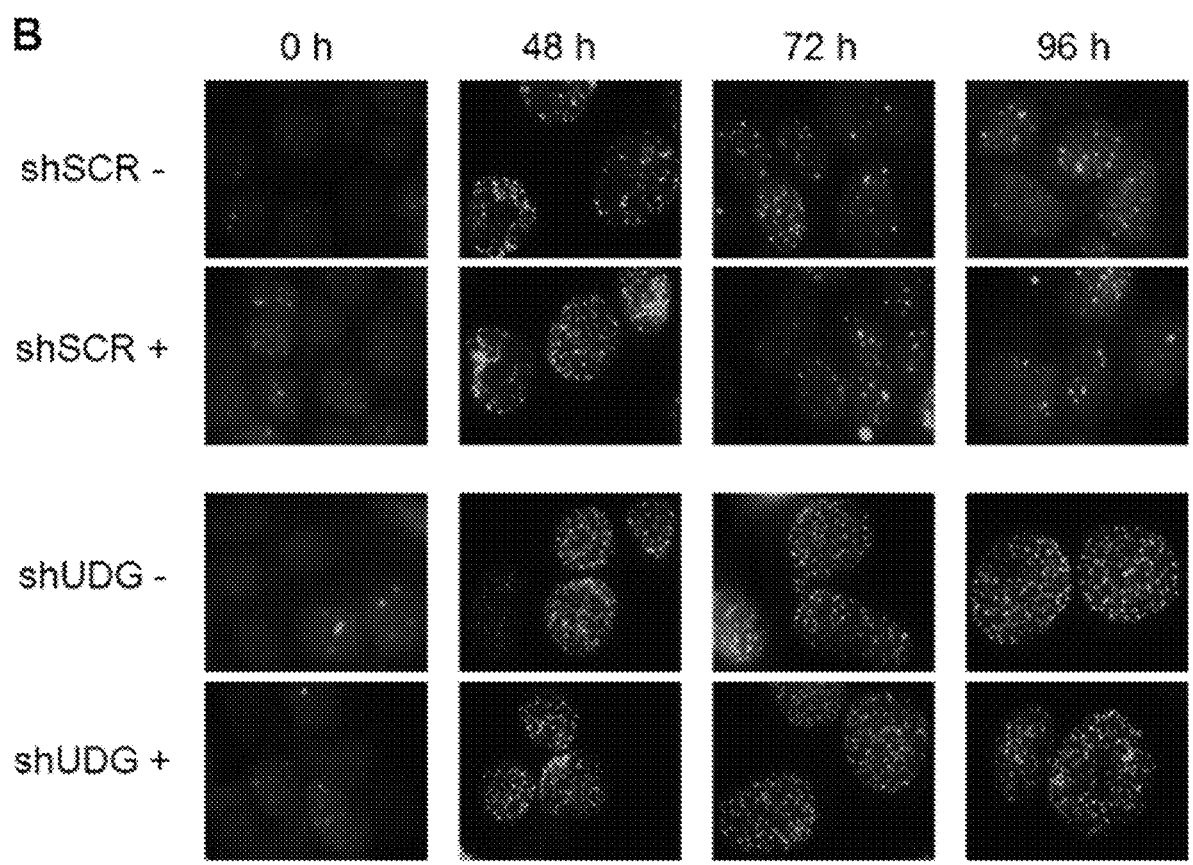
Figure 9C:
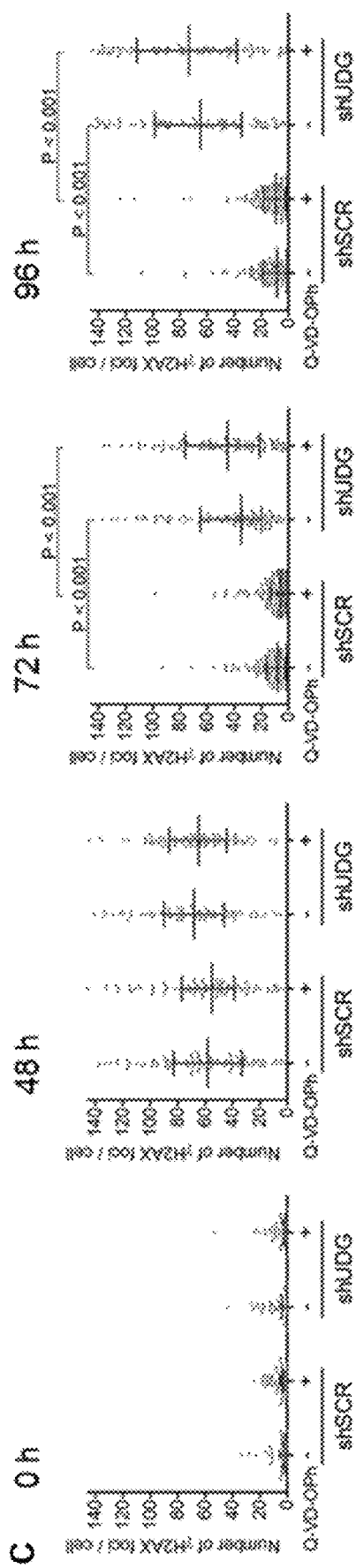
Figure 9D:
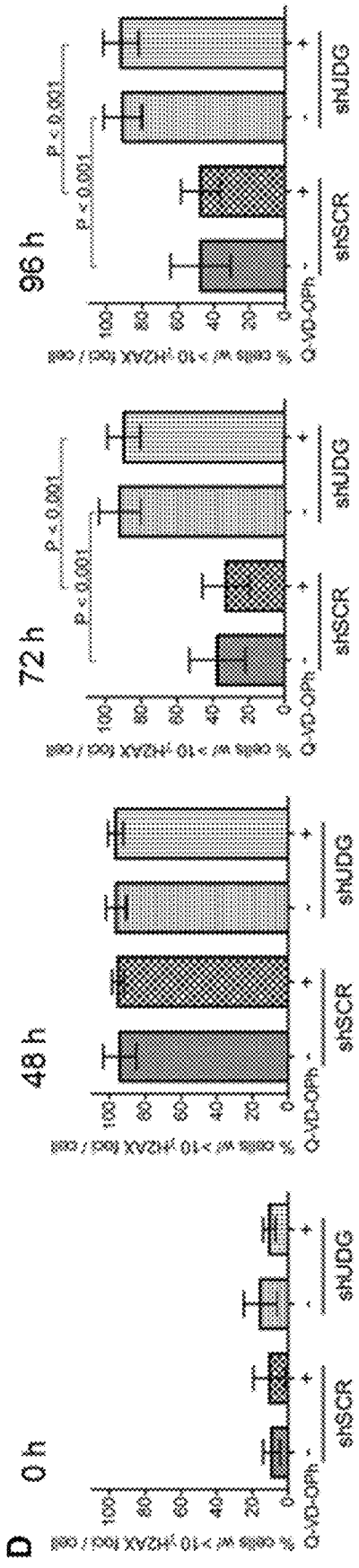
Figure 9E:
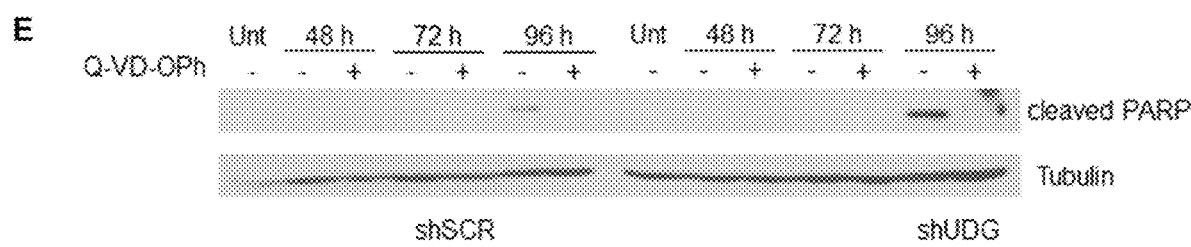

Caspase activation during apoptosis also leads to DNA fragmentation and damage. Therefore, to prove that the formation of DNA damage is the cause, but not the consequence of cell death induced by 5-FdU, we monitored γH2AX foci in both DLD1 and HEC1A cells in the presence or absence of a broad-spectrum caspase inhibitor Q-VD-OPh. If DNA damage were the consequence of caspase activation, then we would expect that the caspase inhibitor should abolish γH2AX foci formation. However, we observed that the number of γH2AX foci and the percentage of γH2AX positive cells were essentially the same between Q-VD-OPh treated and non-treated shSCR-transfected or shUDG-transfected cells (FIG. 6B-6D, and FIG. 9B-9D). These data strongly suggest that the increased DNA damage induced by 5-FdU is not the result of caspase activation. To prove that the caspase inhibitor indeed blocked the apoptotic signaling, we examined the expression of cleaved PARP, a marker of apoptosis, in parallel samples. We found that cleaved PARP by 5-FdU treatment was almost completely blocked by the Q-VD-OPh treatment in both shSCR-transfected and shUDG-transfected cells (FIG. 6E, and FIG. 9E). In addition, the appearance of cleaved PARP in DLD1 and HEC1A cells was not evident until after 24 h and 96h of 5-FdU treatment, respectively (FIG. 6E, and FIG. 9E), whereas DSBs formation was readily detected at 12 h and 48 h of treatment (FIG. 6B-6D, and FIG. 9B-9D). Collectively, these results demonstrate that the formation of DSBs precedes the apoptosis signaling caused by 5-FdU in UDG depleted cells, suggesting that DNA damage is the cause of cell death.

Together these findings demonstrate that loss of UDG in cancer cells enhances the killing effect of 5-FdU, a TS inhibitor through the incorporation of the abnormal bases uracil and 5-FU into DNA.

Example 2

Loss of Uracil DNA Glycosylase (UDG) Overcomes Fluorodeoxyuridine Resistance in p53-Mutant and p53-Deficient Colon Cancer Cells.

Introduction

Fluoropyrimidine (5FU and 5FdU) has been widely used in the treatment of a variety of solid tumors, most notably for colorectal cancer. However nearly one-half of the patients treated with fluoropyrimidine as a first-line therapy failed to respond positively. Fluoropyrimidine can be converted into fluorodeoxyuridine monophosphate (FdUMP) and fluorodeoxyuridine triphosphate (FdUTP): FdUMP exerts its anticancer effects through inhibition of thymidylate synthase (TS), causing nucleotide pool imbalance and uracil incorporation into DNA; and FdUTP can also be directly incorporated into DNA. Because both uracil- and 5FU-DNA are primary removed via Uracil DNA Glycosylase (UDG) initiated base excision repair (BER) pathway, and inhibition of DNA damage repair in cancer cells can improve cytotoxicity in combination with DNA-damaging agents.

Results

Here, we deplete expression of UDG by shRNA to evaluate the 5FdU sensitivity in a panel of cancer cell lines. Our results showed that loss of UDG in DLD1 colon cancer cells retained substantial amounts of both uracil and 5FU incorporation into DNA following 5FdU treatment evaluated by mass spectrometry analysis and AP sites detection assay using a novel fluorescent probe. Further cell cycle and BrdU/PI staining studies have indicated that loss of UDG in DLD1 cancer cells arrested cells at late G1 and early S phase at 24 hours 5FdU exposure. Importantly, UDG KD strikingly retarded replication progression rate after release of the cells in 5FdU free medium examined by DNA fiber assay. Lastly, we tested the 5FdU cytotoxicity in HCT116 (p53 wt), HCT116 (p53 KO), RKO (p53 wt), DLD1 (p53 mut) and HEC1A (p53 mut) cancer cell lines (FIG. 10). Notably, p53 mutant and deficient cancer cells were relatively more resistant to 5FdU than p53 WT cells and loss of UDG overcame this resistance in p53-mutant and p53-KO cancer cells. Unexpectedly, UDG depletion sensitizes p53 mutant and deficient but not p53 WT cancer cells in response to both short-term and long-term 5-FdU exposure (synthetic lethality). These studies confirm that uracil and 5FU incorporation due to loss of UDG accelerate stall or collapse of replication fork and potentiate cytotoxicity of 5FdU in p53-mutant and p53-deficient cancer cells.

Tailoring chemotherapy based on histological subtype and biomarker expression is a favorable strategy for aggressive, treatment-refractory malignancies such as p53 related cancer characterized by high UDG levels. Our observations that UNG expression is elevated in experimental models of TS resistant p53 related cancer prompt us to propose UDG as a novel predictive marker for antimetabolites in human p53 related cancer. Moreover, because UDG depletion restores TS inhibitor sensitivity in resistant cells, UDG-directed BER may be a novel therapeutic target, distinct from the folate metabolism pathway, for overcoming antimetabolite resistance in human p53 related cancer.

Example 3

Loss of Uracil DNA Glycosylase Selectively Re-Sensitizes p53 Mutant and Deficient Cells to 5-FdU Thymidylate synthase (TS) inhibitors including fluoropyrimidines [e.g., 5-Fluorouracil (5-FU) and 5-Fluorodeoxyuridine (5-FdU, floxuridine)] and antifolates (e.g., pemetrexed) are widely used against solid tumors. Previously, we reported that shRNA-mediated knockdown (KD) of uracil DNA glycosylase (UDG) sensitized cancer cells to 5-FdU. Since p53 has also been shown as a critical determinant of the sensitivity to TS inhibitors, we further interrogated 5-FdU cytotoxicity after UDG depletion with regard to p53 status. By analyzing a panel of human cancer cells with known p53 status, it was determined that p53 mutated or deficient cells are highly resistant to 5-FdU. UDG depletion re-sensitizes 5-FdU in p53 mutant and deficient cells, whereas p53 wild-type cells are not affected under similar conditions. Utilizing paired HCT116 p53 wild-type (WT) and p53 knockout (KO) cells, it was shown that loss of p53 improves cell survival after 5-FdU, and UDG depletion only significantly sensitizes p53 KO cells. This sensitization can also be recapitulated by UDG depletion in cells with p53 KD by shRNAs. Additionally, sensitization is also observed with pemetrexed in p53 KO cells, but not with 5-FU, most likely due to RNA incorporation. Importantly, in p53 WT cells, the apoptosis pathway induced by 5-FdU is activated independent of UDG status. However, in p53 KO cells, apoptosis is compromised in UDG expressing cells, but dramatically elevated in UDG depleted cells. Collectively, these results provide evidence that loss of UDG catalyzes significant cell death signals only in cancer cells mutant or deficient in p53.

Materials and Methods
Cell Lines and Drugs

HCT116 p53 KO cells were obtained from the Department of Genetics, Case Western Reserve University, Cleveland, Ohio Other cancer cell lines were purchased from American Type Culture Collection. Details of the cell lines used in this study are listed in Table 1. All cells were maintained in DMEM (Corning 15-017-CV) supplemented with 10% dialyzed fetal bovine serum, 2 mM L-glutamine, 1% MEM NEAA, 100 U/mL penicillin and 100 μg/mL streptomycin. Cells were incubated at 37° C. in a humidified atmosphere of 95% air and 5% $CO_2$. 5-FdU and 5-FU were purchased from Sigma-Aldrich, dissolved respectively in Milli-Q water and DMSO, and stored as a 10 mM stock at −80° C. Pemetrexed was purchased from LC laboratories, and prepared fresh for each experiment by dissolving in Milli-Q water.

TABLE 1

Cell lines and strins used in this work

| Cell Line | Origin | p53 status |
|---|---|---|
| A375 | Melanoma | wt |
| LoVo | Colon Cancer | wt |
| RKO | Colon Cancer | wt |
| HCT116 | Colon Cancer | wt |
| A2780 | Ovarian Cancer | wt |
| H460 | Large cell lung cancer | wt |
| H1299 | Non-small cell lung cancer | Null |
| DLD1 | Colon cancer | S241F |
| HEC1A | Endometrial cancer | R248Q |
| HCT116 p53KO | Colon cancer | KO |

Lentiviral shRNA Knockdown p53 or UDG knockdown was achieved via shRNA transduction. Lentiviral vectors LV-THM-shp53 (which also expresses a GFP reporter) or LV-Bleo-shp53 to perform p53 KD in WT HCT116 cells were obtained from Case Western Reserve University, Cleveland, Ohio Lentiviral vector targeting GFP (sh-GFP) was used as control. UDG shRNA vectors (shUDG: NM_003362.2-656s21c1, shUDG-2: NM_003362.2-758s21c1, and shUDG-3: NM_003362.2-893s21c1) were purchased from Sigma, and a scramble targeting shRNA vector (Sigma) was used as paired control. The lentiviral production and infection were performed as previously described. Cells stably infected with LV-THM-p53 were isolated by cell sorting on the basis of their GFP expression.

Clonogenic Survival Assay

Cancer cells (200-300 cells/well) were seeded in 6-well culture dishes and allowed to adhere overnight. For 5-FdU, cells were treated for 24 h, then gently washed with PBS, and incubated with fresh media for at least 10 days to allow individual colonies to form. For 5-FU or pemetrexed, cells were treated continuously for at least 10 days to form colonies. After 10-18 days, the plates were stained with methylene blue. Colonies containing ≥50 cells were counted. The percentage of survival was determined relative to untreated control averaged over 3 independent experiments.

Western Blots and qPCR

Western blots were performed as previously described Yan et al., Clinical Cancer Research. 2007; 13(5):1532-9. Twenty microgram of protein was loaded on SDS-polyacrylamide gel. The following antibodies were used to detect proteins on the membrane: α-Tubulin (Calbiochem); GAPDH (Santa Cruz Biotechnology); UDG (FL-313) (Santa Cruz Biotechnology); cleaved PARP (Asp214)(19F4) (Cell Signaling); cleaved caspase 3 (Cell Signaling); p53 (FL-393) (Santa Cruz Biotechnology); and p21 (Santa Cruz Biotechnology). For quantitative RT-PCR, total RNA from cells was extracted by using RNeasy Plus Mini Kit (Qiagen). cDNA synthesis was performed by using SuperScript III First Strand Kit (Life Technologies). Q-PCR was achieved with validated TaqMAN MGB FAM™ dye labeled probes (Applied Biosystems) for nuclear UDG on an ABI 7500 Fast Real-time PCR System (Applied Biosystems). β-Actin was used as an endogenous control, and relative gene expression was calculated as $2^{-\Delta\Delta ct}$.

Flow Cytometric Assay of Apoptosis

Cells were seeded in 6-well tissue culture plates ($1.5\times10^5$ cells/well) and allowed to attach overnight. Cells were then treated with 25 nM 5-FdU for 24 h, washed twice with PBS, replenished with drug-free medium at 48, 72, and 96 h. After recovery, the cells floating in the medium were collected. The adherent cells were trypsinized, pelleted, washed in ice-cold PBS, and resuspended in 1× Binding Buffer according to the manufacturer's instructions (FITC Annexin V Apoptosis Detection Kit, BD Pharmingen). Cells were then stained with FITC Annexin V and PI for 15 minutes at room temperature in the dark. Annexin V-FITC detects translocation of phosphatidylinositol from the inner to the out cell membrane during early apoptosis, and PI can enter the cells in late apoptosis or necrosis. Untreated cells were used as control for the double staining. The cells were analyzed immediately after staining using a Attune NXT instrument and FlowJo software. For each measurement, at least 20,000 cells were counted.

Statistical Analysis

Statistical significance between two treatment groups was analyzed using unpaired 2-tailed student's t-test. Significance was assigned for a P-value <0.05. Standard software GraphPad Prism (San Diego, Calif., USA) and Excel 2013 (Microsoft Corp., Redmond, Wash.) were used for all statistical analysis.

Figure 17:
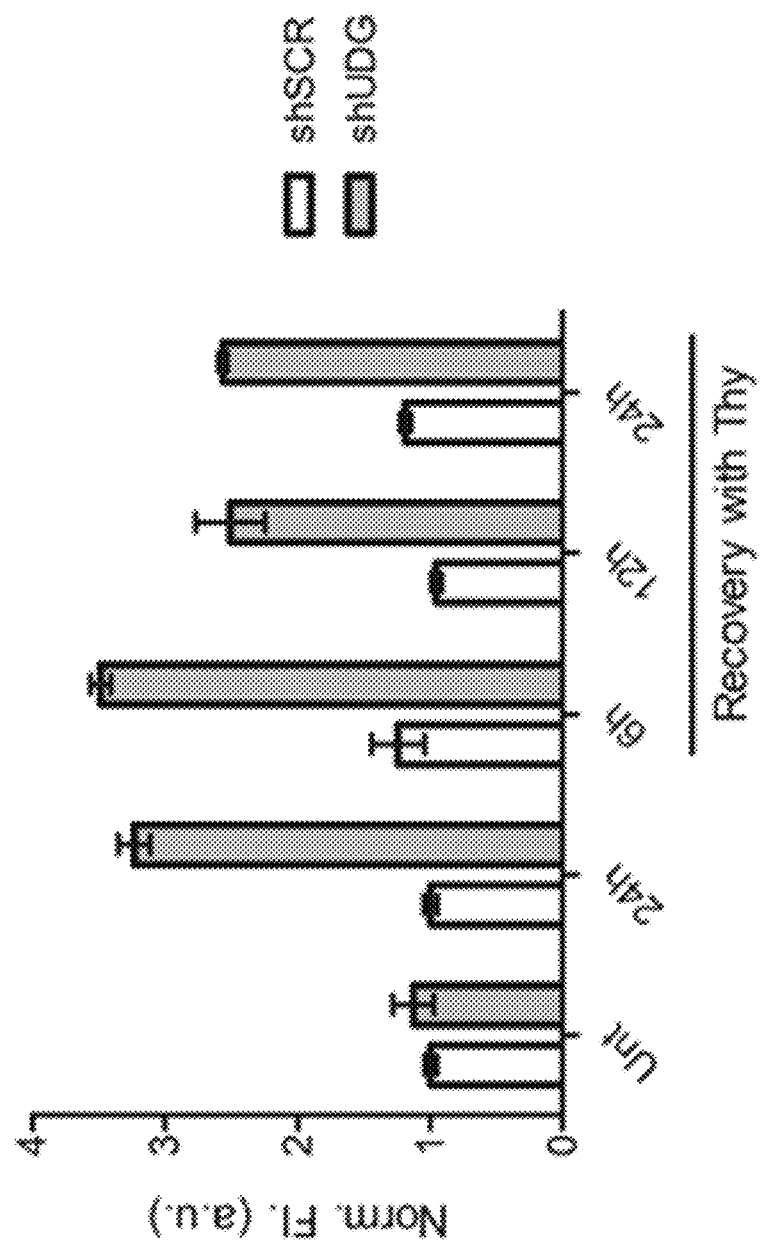
FIG. 17 illustrates the effect of irradiation on p21 induction in various cancer cells with different p53 status. Western blots analysis of p53 and p21 expression in cells treated with (+IR) or without (−IR) gamma-irradiation for 8Gy. Cells were collected 24 hours after irradiation. Tubulin was used as loading control.

Results
p53 Mutation or Deficiency Affords 5-FdU Resistance Among Different Types of Cancer Cells Given that p53 mutations or deficiencies are frequently observed in cancers, and studies have demonstrated that mutations of p53 reduce 5-FU cytotoxicity. To understand whether these mutations also alter the response to 5-FdU, a panel of human cancer cell lines from colon, lung, ovarian, skin, and endometrium with intrinsically differing p53 status were utilized in this study. The p53 status of each cell line is listed in Table 1. To determine p53 protein functionality in p53 WT and p53 mutant (Mut) or deficient cancer cell lines, we assessed p53 levels and expression of p21, a widely accepted initiator of p53 activated signaling, 24 hours after administration of 8Gy gamma-irradiation. All the p53 WT cancer cell lines used in this work induced p21 expression after irradiation, indicating functional p53 in these cell lines (FIG. 17). In order to establish the relationship between p53 status and 5-FdU sensitivity, we evaluated the cytotoxicity of 5-FdU in these cell lines by clonogenic survival assay. As shown in FIG. 15A, the cell lines tested displayed a spectrum of 5-FdU sensitivities with IC50 values ranging from 1.32±0.33 to 269.55±0.73 nM for A2780 and H1299 lines, respectively. Importantly, we observed that, in general, cell lines with p53 mutation or deficiency (FIG. 15A, solid lines) were significantly more resistant to 5-FdU than p53 WT cells (FIG. 15A, dashed lines), with the exception of A375 which has wild-type p53 but an IC50 of 110.81±1.80 nM. In addition, except for A375, the IC50 values for the p53 WT cancer lines clustered together at a lower dose range (<10 nM), whereas p53 mutant or deficient lines clustered at a higher range (>100 nM) (FIG. 15B). These observations are consistent with the hypothesis that p53 mutation or deficiency is associated with resistance to 5-FdU.

Figure 16A:
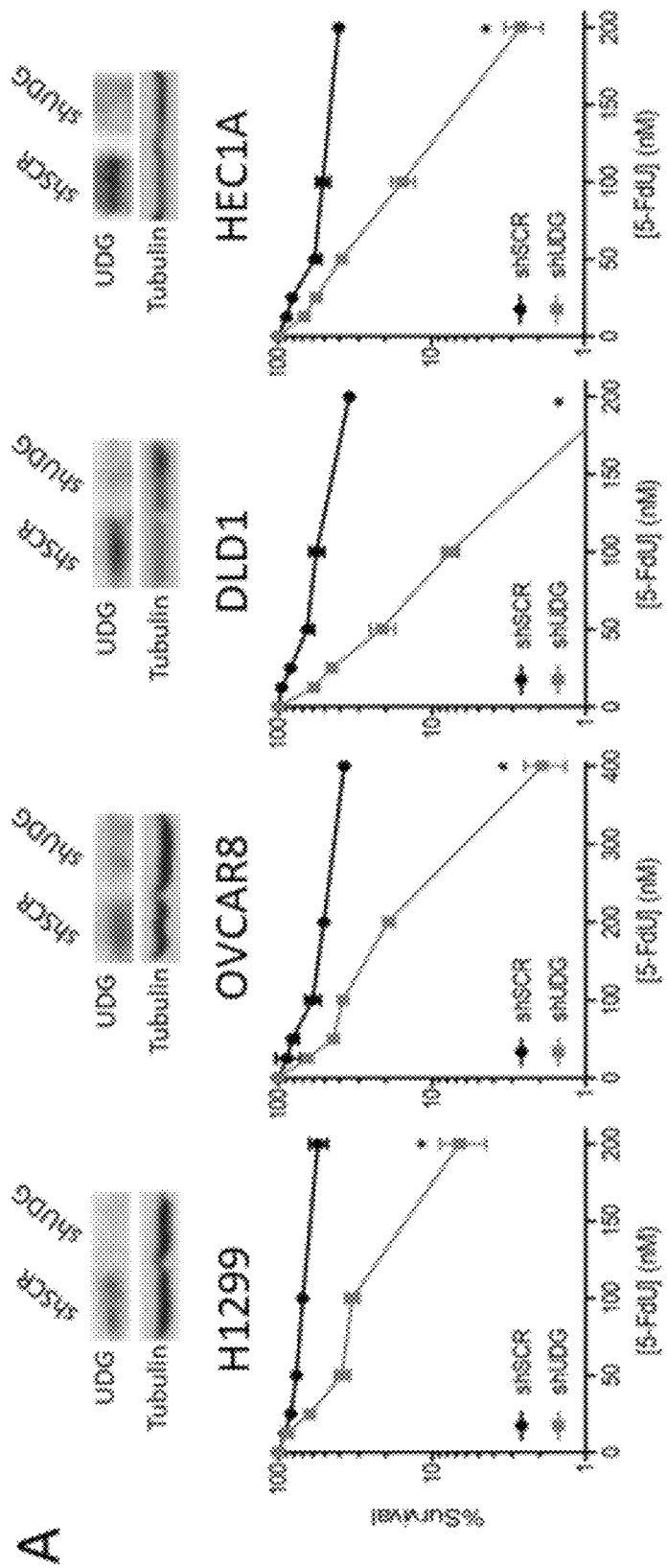
FIGS. 16(A-B) illustrate that UDG depletion selectively sensitizes cells with p53 mutation or deficiency to 5-FdU. Stable cancer cell lines infected with non-targeted scramble control shRNA (shSCR) or UDG-directed shRNA (shUDG) were analyzed by Western blot to examine UDG levels (insert). Clonogenic survival assays of UDG expressing (shSCR) and UDG depleted (shUDG) cancer cells with (A) mutant or deficient p53, or (B) wild-type p53 that are treated with increasing doses of 5-FdU. The results represent three independent experiments that were done in duplicate. (*, P<0.01).
Figure 16B:
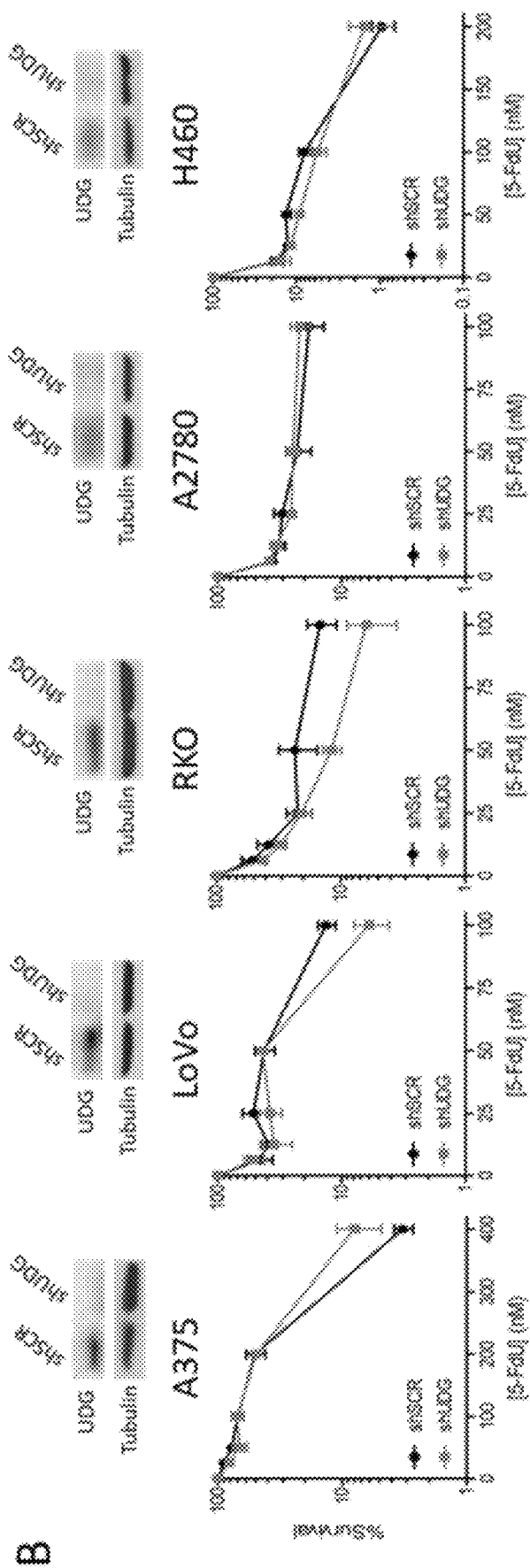

UDG Depletion Sensitizes Cancer Cells with p53 Mutation or Deficiency to 5-FdU Exposure Previously, the discordant findings on sensitization to 5-FdU following UDG depletion were reported using cell models with differing p53 status. To understand whether the divergent responses could be attributed to p53 status, we explored whether UDG depletion could sensitize p53 mutant or deficient cancer cells to 5-FdU differentially. For these experiments, we used shRNA to deplete UDG in various cancer cells lines with differing p53 status, as listed in Table 1. UDG stable knockdown was evaluated by western blot (FIGS. 16A and B). Based on a clonogenic survival assay, we observed that UDG depletion selectively sensitized cells with p53 mutation or deficiency to 5-FdU exposure (FIG. 16A). However, in p53 WT cell lines, UDG depletion did not alter the cytotoxicity of 5-FdU (FIG. 16B). Collectively, these results demonstrate that UDG depletion re-sensitizes p53 mutant or deficient cancer cells, providing a novel therapeutic target for patients with p53 mutant tumors.

5-FdU Resistance in p53 Knockout (KO) or Knockdown (KD) Cells is Reversed by UDG Depletion Since many studies have identified gain of various functions for specific p53 mutated proteins, we next asked whether loss of wild-type p53 protein expression can alter the response to 5-FdU. To address this, we utilized paired HCT116 colon cancer cell lines with or without genetic TP53 deletion and tested their sensitivity to 5-FdU, and the loss of p53 expression was evaluated by western blot (FIG. 11A). Using a clonogenic survival assay, we demonstrated that p53 KO cells were more resistant to 5-FdU than p53 WT cells (FIG. 11B). Knockdown of p53 by shRNA recapitulates the resistance observed in p53 KO cells (FIG. 11B), indicating that p53 status is a key mediator of the response of HCT116 cells to 5-FdU.

To understand whether loss of p53 protein will affect the response to 5-FdU after UDG depletion, we knocked down UDG by shRNA in both HCT116 p53 WT and p53 KO cells. UDG knockdown levels were shown to be greater than 90% as evaluated by Q-PCR and western blot (FIG. 11 C, D). In agreement with our data using p53 mutant cells, UDG depletion greatly enhanced cytotoxicity of 5-FdU in p53 KO cells but did not significantly affect p53 WT cells (FIG. 11E, F), indicating that p53 is involved in regulating the response to 5-FdU following UDG depletion. To exclude the off-target effect of a single shRNA, we also utilized two other shRNAs that target UDG in HCT116 p53 WT and p53 KO cells and observed similar effect. In addition, depletion of UDG also potentiated 5-FdU cytotoxicity in two HCT116 cancer cells with different shRNAs targeted to p53 (FIG. 12A-E). Collectively, these results confirm that loss of p53 protein renders cells resistant to 5-FdU, and UDG depletion selectively re-sensitizes p53 KO and KD cells to 5-FdU.

UDG Depletion Selectively Sensitizes p53 KO Cancer Cells to Pemetrexed and 5-FU

Although all TS inhibitors have the ability to block TS, disrupting DNA replication and leading to uracil incorporation into DNA, differences among distinct TS inhibitors have been reported in terms of their other metabolism mediated cytotoxic pathways. For example, pemetrexed polyglutamate derivatives also demonstrate inhibitory activity for other folate-dependent enzymes such as glycinamide ribonucleotide, but to a lesser extent. Moreover, unlike 5-FdU, which mainly exerts its cytotoxicity due to effects at the DNA level, studies have revealed that the cytotoxicity of 5-FU is primarily RNA-mediated, as 5-FU is metabolized to fluorouridine triphosphate (FUTP) which affects multiple RNA processes following its incorporation into RNAs. In order to address the question of whether p53 status is responsible for differences in sensitivity to other TS inhibitors, including pemetrexed and 5-FU, in UDG depleted cells, we evaluated cell viability following drug exposure in UDG depleted p53 WT and p53 KO cancer cells. Similar to our observations with 5-FdU, no significant survival differences were found between UDG expressing and UDG depleted cells in the presence of p53 (FIG. 13 A, B). However, in the absence of p53, UDG depletion sensitized cells to pemetrexed (FIG. 13 C), while loss of UDG only moderately sensitized cells to 5-FU at high concentrations (FIG. 13D), reaffirming that the primary cytotoxic effect of 5-FU depends on RNA incoporation. Together, these results indicate that UDG depletion also sensitizes cells without p53 to other TS inhibitors, mainly through generation of DNA damage.

5-FdU Activates Cell Death in p53 KO Cancer Cells with Depleted UDG

Figure 14A:
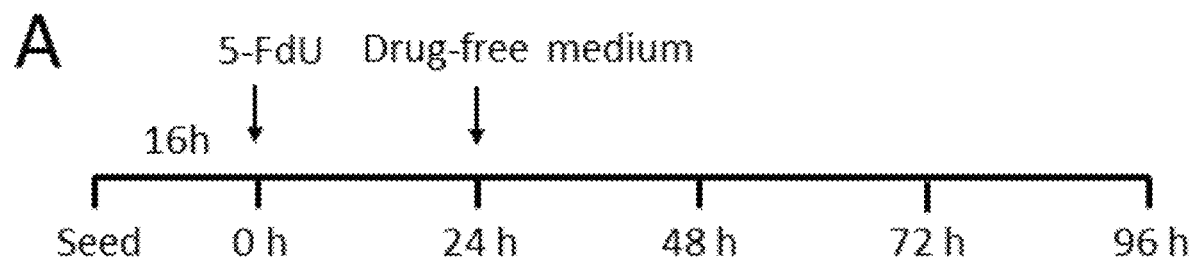
FIGS. 14(A-E) illustrate that UDG depletion induces cell death caused by 5-FdU in p53 KO cancer cells. (A) Schematic diagram of the treatment for HCT116 p53WT (shSCR and shUDG) and p53KO (shSCR and shUDG) cells with 25 nM 5-FdU for 24 h, washed, replenished with drug-free medium at indicated time points. (B) Untreated (Unt) or treated cells were subjected to FITC Annexin V and propodium iodide (PI) staining and analyzed by flow cytometry. Representative flow plots of three independent experiments are shown. (C) Cell death is expressed as 100%-viable cells (Annexin V negative and PI negative). Values indicate mean values ±SD. All experiments were performed independently for three times. (*P<0.01). Protein expression involved in regulation of apoptotic cell death in response to 5-FdU were detected in HCT116 (D) p53 WT (shSCR and shUDG) and (E) p53 KO (shSCR and shUDG) cells. (*, non-specific bands).
Figure 14C:
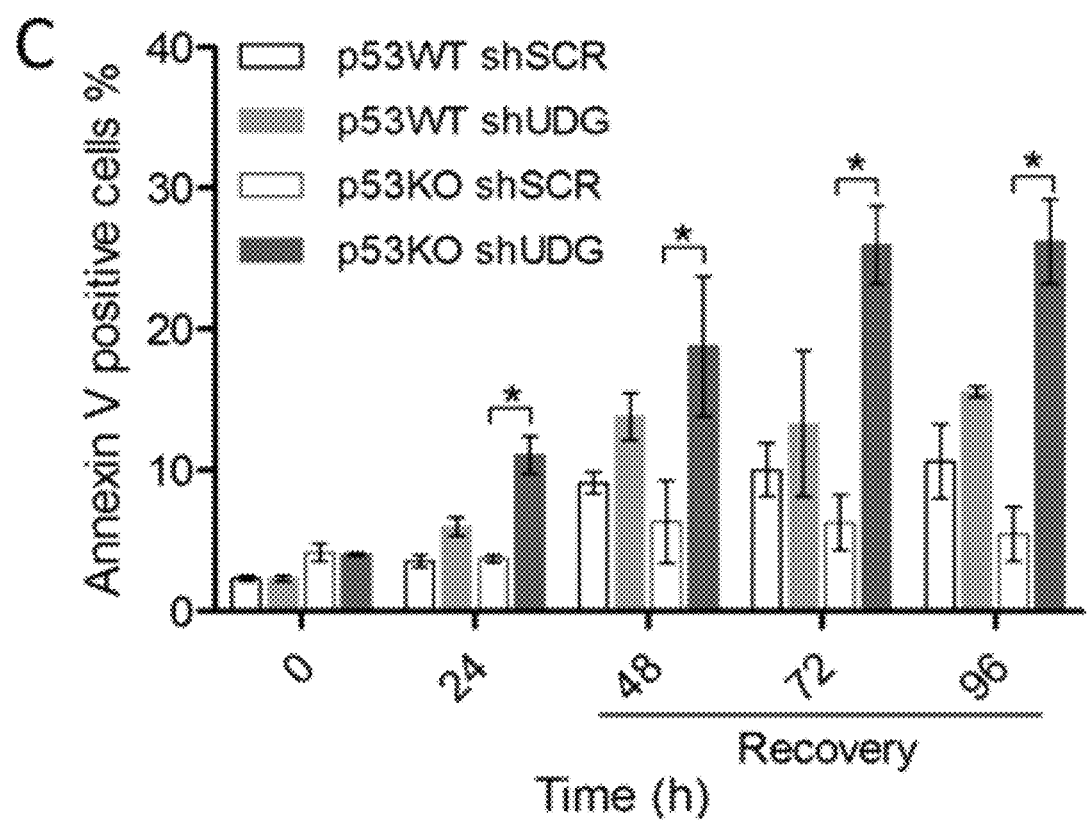
Figure 14B:
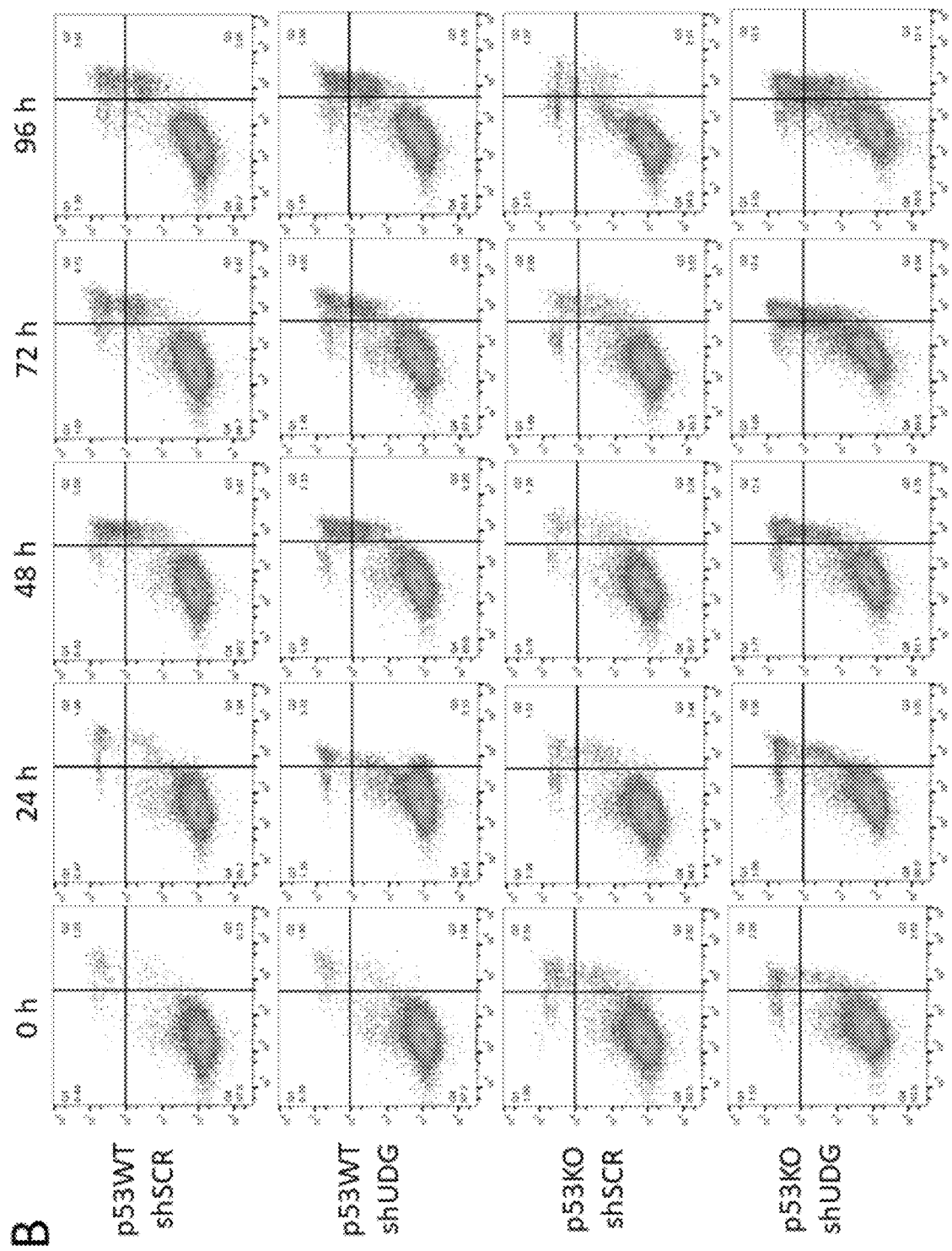

To understand whether 5-FdU resistance observed in p53 KO cells is due to a failure to activate cell death pathways, we monitored cell death progression by Annexin V and propidium iodide (PI) staining. Cells were exposed to 5-FdU for 24 h, washed with PBS, and then allowed to recover in drug free medium for a total of 48, 72, and 96 h (FIG. 14A). In cells with wild-type p53, 5-FdU caused significant cell death (Annexin V and PI positive) at 48 h which was retained at 72 h and 96 h in both UDG expressing and UDG depleted cells (FIG. 14 B, C). However, in the absence of p53, cell death caused by 5-FdU was significantly lower in UDG expressing cells, while in UDG depleted cells, cell death was detected at 24 h and significantly elevated at 48 to 96 h (FIG. 14 B, C). These data suggest that 5-FdU induced cell death is dependent upon p53, supporting the observation that drug resistance can be observed as a result of abrogation of the p53 mediated cell death pathway. Importantly, UDG depletion significantly potentiates death of cells lacking wild type p53 activity through a p53 independent pathway.

To further elucidate whether the cell death caused by 5-FdU is due to apoptosis, we examined expression of proteins involved in the activation of the apoptotic pathway. In wild-type p53 cells, we observed that p53 expression was induced at 24 h and the induction remained for 96 hours in both shSCR and shUDG cells following 5-FdU exposure (FIG. 14 D). The expression of cleaved PARP, a hallmark of apoptotic cell death, was induced at 48 h and persisted through 72 h and 96 h in p53 WT cells regardless of whether UDG was present or not (FIG. 14 D). In addition, cleaved caspase 3 was also detected in both UDG expressing or depleted p53 WT cells (FIG. 14 D). In the absence of p53, induction of cleaved PARP or activated caspase 3 was not detected in cells expressing UDG after 5-FdU exposure (FIG. 14 E), while both were robustly induced from 48 h to 96 h in cells depleted of UDG (FIG. 14 E). Taken together, our results suggest that 5-FdU induced apoptosis is mediated through p53, and the lack of apoptosis activation due to loss of p53 is responsible for the enhanced cell survival observed in p53 KO cells. However, in p53 KO cell with coincident UDG depletion, 5-FdU selectively activates a p53-independent apoptotic pathway through a mechanism which needs further investigation.

In this example, we utilized multiple cancer cells bearing differing p53 status with or without UDG expression. We observed that loss of UDG selectively re-sensitized cancer cells with p53 mutation or deficiency to 5-FdU, but did not alter the response of p53 wild-type cells. These results demonstrate that UDG, through its function of removing uracil or 5-FU, plays a major role in the effect of 5-FdU on the response of cells lacking wild type p53 activity. Our findings resolve the unexplained discrepancy observed in a number of prior studies regarding the role of UDG in sensitivity to TS inhibitors. Prior studies revealed that either loss of UDG enhanced the cytotoxicity of 5-FdU or pemetrexed in cancer cells, or overexpression or inhibition of UDG had no effect on the sensitivity of human or mouse cells to TS inhibition. The difference, therefore, is dependent on p53 status.

Our results demonstrated that inhibition of UDG selectively sensitized p53 mutant and deficient cancer cells to 5-FdU, but did not alter the response in p53 WT cells. Importantly, we have observed that apoptosis following 5-FdU is efficiently induced in the presence of p53 but highly compromised in cells lacking p53, indicating that the activation of the 5-FdU induced cell death pathway is dependent on p53. Further studies with different p53 WT cell lines also revealed cells highly sensitive to 5-FdU with IC50 values lower than 10 nM. One exception we observed was in the A375 melanoma cells line, which has a wild type TP53 gene. A375 was relatively insensitive to 5-FdU and had an IC50 of 110.81±1.80 nM. Clearly, more knowledge is needed regarding the p53 mediated cell death pathway and how 5-FdU, with or without UDG, causes damage and triggers cell death. In response to 5-FdU, cells lacking wild-type p53, combined with UDG depletion, activate cell death in a p53 independent manner, which reverses chemoresistance and selectively re-sensitizes these cancer cells to 5-FdU.

Other embodiments of the invention will be apparent to those skilled in the art from a consideration of the specification or practice of the invention disclosed herein. It is intended that the specification and examples be considered as exemplary only, with the true scope of the invention being indicated by the following claims. All patents, publication, and referenced cited are incorporated by reference in their entirety.

Having described the invention, the following is claimed:

1. A method of treating cancer in a subject, comprising:
   determining the p53 status and the level of UDG in cancer cells of the subject; and
   administering an antimetabolite agent in combination with an AP endonuclease inhibitor or UDG inhibitor if the determined level of UDG expression in the cancer cells is increased relative to the control level and the cancer cells are p53 mutant or deficient cancer cells, wherein the antimetabolite promotes introduction of uracil or a UDG substrate into the cancer cell DNA.

2. The method of claim 1, wherein the cancer is selected from the group consisting of hepatocellular carcinoma, osteogenic sarcoma, colorectal cancer, uterine cancer, lung cancer, glioblastoma, esophageal carcinoma, bladder cancer, squamous cell carcinoma, leukemia and lymphoma.

3. The method of claim 2, wherein the cancer is human lung, colorectal, or uterine cancer.

4. The method of claim 2, wherein the human lung cancer is non-small cell lung cancer.

5. The method of claim 1, wherein the antimetabolite agent comprises at least one of a thymidylate synthase inhibitor, antifolate agent, or a pyrimidine analogue.

6. The method of claim 5, wherein the antimetabolite agent is a thymidylate synthase inhibitor.

7. The method of claim 6, wherein the thymidylate synthase inhibitor is floxuridine (5FdU).

8. The method of claim 5, wherein the antimetabolite agent is an antifolate agent.

9. The method of claim 8, wherein the antifolate agent is selected from the group consisting of pemetrexed and methotrexate.

10. The method of claim 1, wherein the AP endonuclease inhibitor is selected from group consisting of methoxyamine, O-benzylhydroxylamine; ethyl aminooxyacetate; aminooxyacetic acid; ethyl aminooxyacetate; H₂NOCHMeCO₂H; carboxymethoxyamine; aminooxyacetic acid; HN=C(NH₂)SCH₂CH₂ONH₂; H₂NO(CH₂)₃SC(NH₂)=NH; MeOC(O)CH(NH₂)CH₂ONH₂; H₂NOCH₂CH(NH₂)CO₂H; canaline; H₂NO(CH₂)₄ONH₂; O-(p-nitrobenzyl)hydroxylamine; 2-amino-4-(aminooxymethyl)thiazole; 4-(aminooxymethyl)thiazole; O,O'-(o-phenylenedimethylene)dihydroxylamine; 2,4-dinitrophenoxyamine; O,O'-(m-phenylenedimethylene)dihydroxylamine; O,O'-(p-phenylenedimethylene)dihydroxylamine; H₂C=CHCH₂ONH₂; H₂NO(CH₂)₄ONH₂; H₃C—(CH₂)₁₅—O—NH₂, 2,2'-(1,2-ethanediyl)bis(3-aminooxy)butenedioic acid dimethyl diethyl ester;

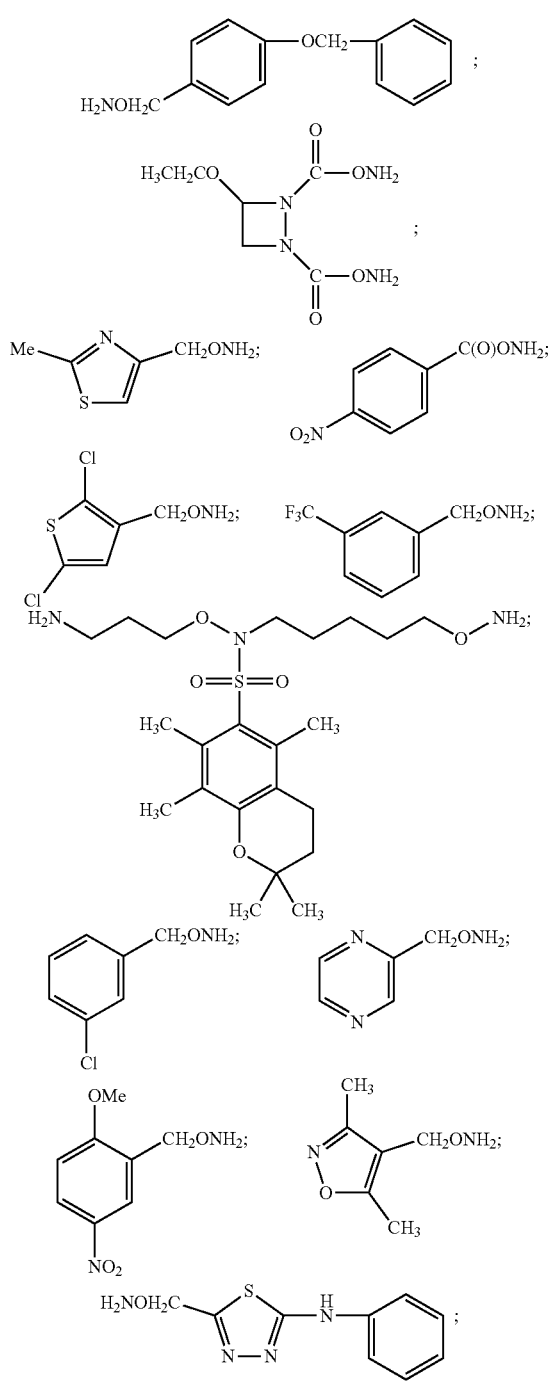

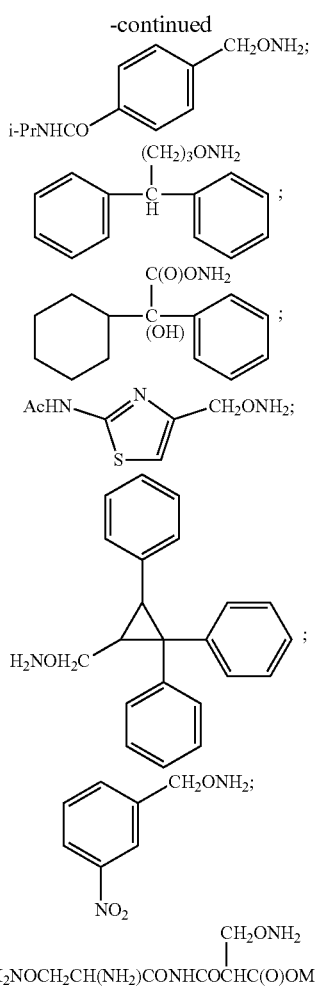

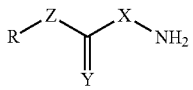

H₂NOCH₂CH(NH₂)CONHCOCHC(O)OMe;

a compound having a structure of Formula I:

$$R\overset{Z}{\diagdown}\underset{Y}{\overset{X}{\diagup}}NH_2 \quad \text{Formula I}$$

wherein X is O or NH,
Y is O, S, or NH,
Z is absent or represents O, S, or NH, and
R represents a hydrogen or a hydrocarbon moiety,
and pharmaceutically acceptable salts thereof.

11. The method of claim 10, wherein the AP endonuclease inhibitor is methoxyamine.

12. The method of claim 1, wherein the UDG inhibitor is a RNAi construct that inhibits or reduces expression of the UDG expression in the cancer cells of the subject.

13. The method of claim 12, the RNAi construct comprising a shRNA.

14. The method of claim 1, wherein the antimetabolite is 5-FdU or pemetrexed and the AP endonuclease inhibitor is methoxyamine.

15. The method of claim 1, wherein the AP endonuclease inhibitor or UDG inhibitor is administered at an amount effective to potentiate the cytotoxicity of the antimetabolite agent administered to the cancer cells.

16. The method of claim 1, wherein the AP endonuclease inhibitor or UDG inhibitor is administered at an amount sufficient to sensitize the cancer cells to the antimetabolite agent without causing undue sensitization of normal cells.

17. A method of treating a p53 mutant cancer in a subject comprising:
  determining the level of UDG expression in the subjects cancer cells; and
  administering an antifolate agent that induces or promotes incorporation of a uracil or a UDG substrate into DNA of cancer cells to the subject in combination with a UDG inhibitor if the determined level of UDG expression is increased compared to a control level.

18. The method of claim 17, wherein the p53 mutant cancer is a p53 related cancer selected from the group consisting of hepatocellular carcinoma, osteogenic sarcoma, colorectal cancer, uterine cancer, lung cancer, glioblastoma, esophageal carcinoma, bladder cancer, squamous cell carcinoma, leukemia and lymphoma.

19. The method of claim 16, wherein the p53 mutant cancer is p53 related lung, colorectal, or uterine cancer.

20. The method of claim 19, wherein the p53 related lung cancer is non-small cell lung cancer.

21. The method of claim 17, wherein the antifolate agent is selected from the group consisting of pemetrexed and methotrexate.

22. The method of claim 17, wherein the AP endonuclease inhibitor is selected from group consisting of methoxyamine, O-benzylohydroxylamine; ethyl aminooxyacetate; aminooxyacetic acid; ethyl aminooxyacetate; $H_2NOCHMeCO_2H$; carboxymethoxyamine; aminooxyacetic acid; $HN=C(NH_2)SCH_2CH_2ONH_2$; $H_2NO(CH_2)_3SC(NH_2)=NH$; $MeOC(O)CH(NH_2)CH_2ONH_2$; $H_2NOCH_2CH(NH_2)CO_2H$; canaline; $H_2NO(CH_2)_4ONH_2$; O-(p-nitrobenzyl)hydroxylamine; 2-amino-4-(aminooxymethyl)thiazole; 4-(aminooxymethyl)thiazole; O,O'-(o-phenylenedimethylene)dihydroxylamine; 2,4-dinitrophenoxyamine; O,O'-(m-phenylenedimethylene)dihydroxylamine; O,O'-(p-phenylenedimethylene)dihydroxylamine; $H_2C=CHCH_2ONH_2$; $H_2NO(CH_2)_4ONH_2$; $H_3C—(CH_2)_{15}-O—NH_2$, 2,2'-(1,2-ethanediyl)bis(3-aminooxy)butenedioic acid dimethyl diethyl ester;

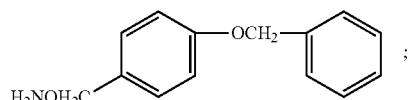

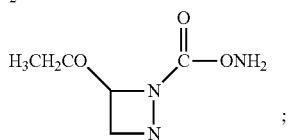

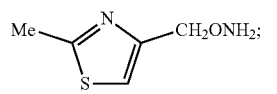

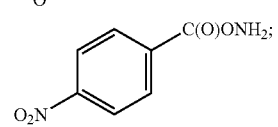

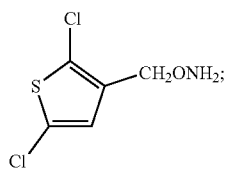

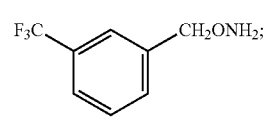

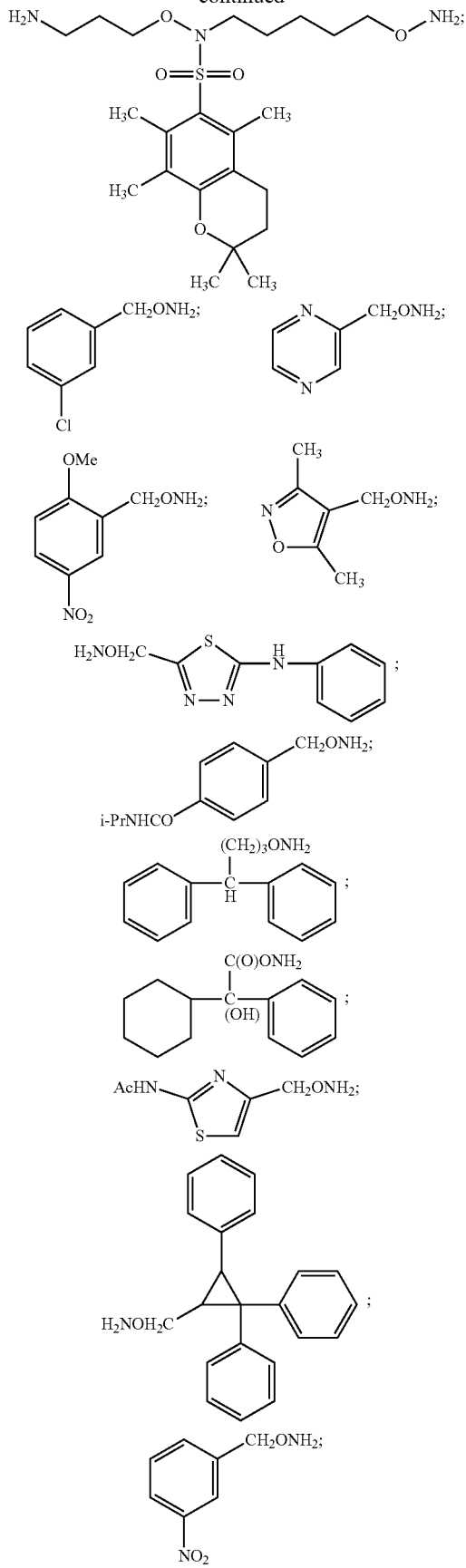

-continued

H$_2$NOCH$_2$CH(NH$_2$)CONHCOCHC(O)OMe;
with CH$_2$ONH$_2$ substituent a compound having a structure of Formula I:

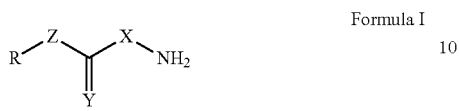

Formula I wherein X is O or NH,
Y is O, S, or NH,
Z is absent or represents O, S, or NH, and
R represents a hydrogen or a hydrocarbon moiety,
and pharmaceutically acceptable salts thereof.

23. The method of claim 17, wherein the UDG inhibitor is a RNAi construct that inhibits or reduces expression of the UDG expression in a cell.

24. The method of claim 23, the RNAi construct comprising a shRNA.

25. The method of claim 17, wherein the UDG inhibitor is administered at an amount effective to potentiate the cytotoxicity of the antifolate agent administered to the cancer cells.

26. The method of claim 17, wherein the UDG inhibitor is administered at an amount sufficient to sensitize the cancer cells to the antifolate agent without causing undue sensitization of normal cells.

* * * * *